US006703237B2

(12) United States Patent
Samulski et al.

(10) Patent No.: US 6,703,237 B2
(45) Date of Patent: Mar. 9, 2004

(54) METHODS AND FORMULATIONS FOR MEDIATING ADENO-ASSOCIATED VIRUS (AAV) ATTACHMENT AND INFECTION AND METHODS FOR PURIFYING AAV

(75) Inventors: Richard Jude Samulski, Chapel Hill, NC (US); Candace Summerford, Chapel Hill, NC (US)

(73) Assignee: University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 10/102,314

(22) Filed: Mar. 20, 2002

(65) Prior Publication Data

US 2002/0136710 A1 Sep. 26, 2002

Related U.S. Application Data

(62) Division of application No. 09/228,203, filed on Jan. 11, 1999, now Pat. No. 6,410,300.
(60) Provisional application No. 60/071,210, filed on Jan. 12, 1998.

(51) Int. Cl.$^7$ .............................................. C12N 15/864

(52) U.S. Cl. ...................... 435/320.1; 435/455; 435/456

(58) Field of Search ............................. 435/320.1, 455, 435/456; 424/93.2

(56) References Cited

U.S. PATENT DOCUMENTS

| | | | | |
|---|---|---|---|---|
| 6,143,548 A | 11/2000 | O'Riordan et al. | ......... | 435/239 |
| 6,146,874 A | 11/2000 | Zolotukhin et al. | ....... | 435/235.1 |
| 6,194,192 B1 | 2/2001 | Ueno et al. | ................. | 435/239 |

FOREIGN PATENT DOCUMENTS

| | | |
|---|---|---|
| WO | WO 97/08298 | 3/1997 |
| WO | WO 97/32010 | 4/1997 |

OTHER PUBLICATIONS

Rosenberg et al., "Gene therapist, heal thyself," Science 287: 1751, Mar. 2000.*
Chiorini et al., "Cloning of adeno–associated virus type 4 (AAV3) and generation of recombinant AAV4 particles," J. Virol. 71 (9): 6823–6833, Sep. 1997.*
Handa et al., "Adeno–associated virus (AAV)–3–based vectors transduce haematopoietic cells not susceptible to transduction with AAV–2–based vectors," J. Gen. Virol. 81: 2077–2084, 2000.*
Hauck et al., "Characterization of tissue tropism determinants of adeno–associated virus type 1," J. Virol. 77(4): 2768–2774, Feb. 2003.*
Chiorini et al., "Cloning and characterization of adeno–associated virus type 5," J. Virol. 73 (2): 1309–1319, Feb. 1999.*
Halbert et al., "Adeno–associated virus type 6 (AAV6) vectors mediate efficient transduction of airway epithelial cells in mouse lungs compared to that of AAV2 vectors," J. Virol. 75 (14): 6615–6624, Jul. 2001.*
Kaludov et al., "Scalable purification of adeno–associated virus type 2, 4, or 5 using ion–exchange chromatography," Hum. Gene Ther. 13 (10): 1235–1243, Jul. 2002 (Abstract only).*
Verma et al., "Gene therapy—promises, problems and prospects," Nature 389: 239–242, Sep. 1997.*
Orkin et al., "Report and recommendations of the panel to assess the NIH investment in research on gene therapy," issued by the US Natl. Inst. of Health, Dec. 7, 1995.*
Bella et al.; *The Structure of the Two Amino–Terminal Domains of Human ICAM–1 Suggests How it Functions as a Rhinovirus Receptor and as an LFA–1 Integrin Ligand*, Proc. Natl. Acad. Sci. USA, 95:4140–4145 (Apr. 1998).
Carter; *The Promise of Adeno–Associated Virus Vectors*, Nature Biotechnology 141725–1726 (Dec. 1996).
Chen et al.; *Dengue Virus Infectivity Depends on Envelope Protein Binding to Target Cell Heparan Sulfate*, Nature Medicine 3:866–871 (Aug. 1997).
Chung et al.; *A27L Protein Mediates Vaccinia Virus Interaction with Cell Surface Heparan Sulfate*, Journal of Virology, 72:1577–1585 (Feb. 1998).
Clark et al., *Efficient and Rapid Purification of Recombinant Adeno–Associated Virus by Perfusion Chromatography*, American Society of Gene Therapy, May 28–31, 1998, Abstract # 701.
Clark et al., *Human Gene Therapy* 6: 1329 (1995).
Compton et al.; *Initiation of Human Cytomegalovirus Infection Requires Initial Interaction with Cell Surface Heparan Sulfate*, Virology 193:834–841 (1993).
Coulson et al.; *Rotavirus Contains Integrin Ligand Sequences and a Disintegrin–like Domain that are Implicated in Virus Entry into Cells*, Proc. Natl. Acad. Sci. USA, 94:5389–5394 (May 1997).

(List continued on next page.)

Primary Examiner—Scott D. Priebe
(74) Attorney, Agent, or Firm—Myers Bigel Sibley & Sajovec, P.A.

(57) ABSTRACT

Primary receptors and co-receptors for adeno-associated virus (AAV) attachment to and infection of target cells are described. Such receptors can be used to facilitate AAV attachment to and infection of cells, e.g., for gene therapy. Methods for purification and/or concentration of AAV are also described. Methods of facilitating or enhancing AAV infection of a cell are also provided. Also described are methods of inhibiting or preventing infection of AAV into a cell. Cell samples may be screened for permissiveness for AAV attachment and infection by detecting the presence or abundance of cellular receptors that mediate attachment and/or infection of AAV into the cell. Formulations and kits for mediating AAV attachment to, and infection of, cells are also provided herein.

30 Claims, 17 Drawing Sheets

OTHER PUBLICATIONS

Dyer, et al. *Dextran Sulfate Can Act as an Artificial Receptor to Mediate a Type–Specific Herpes Simplex Virus Infection via Glycoprotein B*, Journal of Virology, 71:191–198 (Jan. 1997).

Evander et al.; *Identification of the $\alpha_6$ Integrin as a Candidate Receptor for Papillomaviruses*, Journal of Virology, 71:2449–2456 (Mar. 1997).

Feyzi et al.; *Structural Requirement of Heparan Sulfate for Interaction with Herpes Simplex Virus Type 1 Virions and Isolated Glycoprotein C*, Journal of Biological Chemistry, 272:24850–24857 (1997).

Gavrilovskaya et al.; *$\beta_3$ Integrins Mediate the Cellular Entry of Hantaviruses that Cause Respiratory Failure*, Proc. Natl. Acad. Sci. USA, 95:7074–7079 (Jun. 1998).

Goldman et al.; *Expression of $\alpha_v\beta_5$ Integrin is Necessary for Efficient Adenovirus–Mediated Gene Transfer in the Human Airway*, Journal of Virology, 69:5951–5958 (Oct. 1995).

Grimm et al.; *Novel Tools for Production and Purification of Recombinant Adenoassociated Virus Vectors*, Human Gene Therapy 9:2745–2760 (Dec. 10, 1998).

Herold et al.; *Glycoprotein C–Independent Binding of Herpes Simplex Virus to Cells Requires Cell Surface Heparan Sulphate and Glycoprotein B*, Journal of General Virology, 75:1211–1222 (1994).

Herold et al.; *Identification of Structural Features of Heparin Required for Inhibition of Herpes Simplex Virus Type 1 Binding*, Virology 206:1408–1116 (1995).

Huang et al.; *Adenovirus Interaction with Distinct Integrins Mediates Separate Events in Cell Entry and Gene Delivery to Hematopoietic Cells*, Journal of Virology 70:4502–4508 (Jul. 1996).

Kari et al.; *A Human Cytomegalovirus Glycoprotein Complex Designated gC–11 is a Major Heparin–Binding Component of the Envelope*, Journal of Virology 66:1761–1764 (Mar. 1992).

King et al.; *Echovirus 1 Interaction with the Isolated VLA–2 I Domain*, Journal of Virology 69:3237–3239 (May 1995).

Li et al.; *Adenovirus Endocytosis via $\alpha_v$ Integrins Requires Phosphoinositide–3–OH Kinase*, Journal of Virology 72:2055–2061 (Mar. 1998).

Lycke et al.; *Binding of Herpex Simplex Virus to Cellular Heparan Sulphate, an Initial Step in the Adsorption Process*, Journal of General Virology 72:1131–1137 (1991).

Mathias et al.; *Multiple Adenovirus Serotypes Use $\alpha v$ Integrins for Infection*, Journal of Virology 68:6811–6814 (Oct. 1994).

Nadkarni et al.; *Directional Immobilization of Heparin onto the Nonporous Surface of Polystyrene Microplates*, BioTechniques 23:382–385 (Sep. 1997).

Neff et al.; *Foot–and–Mouth Disease Virus Virulent for Cattle Utilizes the Integrin $\alpha_v\beta_3$ as Its Receptor*, Journal of Virology 72:3587–3594 (May 1998).

Neyts et al.; *Sulfated Polymers Inhibit the Interaction of Human Cytomegalovirus with Cell Surface Heparan Sulfate*, Virology 189:48–58 (1992).

Roivainen et al.; *Entry of Coxsackievirus A9 into Host Cells: Specific Interactions with $\alpha_v\beta_3$ Integrin, the Vitronectin Receptor*, Virology 203:357–365 (1994).

Secchiero et al.; *Role of the Extracellular Domain of Human Herpesvirus 7 Glycoprotein B in Virus Binding to Cell Surface Heparan Sulfate Proteoglycans*, Journal of Virology 71:4571–5680 (Jun. 1997).

Shieh et al.; *Cell Surface Receptors for Herpes Simplex Virus are Heparan Sulfate Proteoglycans*, The Journal for Cell Biology, 116:1273–1280 (1992).

Summerford et al.; *A Role for Integrin $\alpha V\beta 5$ in AAV Infection*, VIIth International Parvovirus Workshop and $1^{st}$ Euroconference on Health Benefits and Risks from Parvovirus Infection, Heidelberg, Germany, Sep. 3–7, 1997.

Summerford et al.; *Membrane–Associated Heparan Sulfate Proteoglycan is a Receptor for Adeno–Associated Virus Type 2 Virions*, Journal of Virology 72:1438–1445 (Feb. 1998).

Summerford et al.; *AdenoAssociated Viral Vectors for Gene Therapy*, Biogenic Amines 14:451–475 (1998).

Summerford et al.; *$\alpha V\beta 5$ Integrin: a Co–Receptor for Adeno–Associated Virus Type 2 Infection*, Nature Medicine 5:78–82 (Jan. 1999).

Tamayose et al., Human Gene Therapy 7: 507 (1996).

Trybala et al.; *Mode of Interaction Between Pseudorabies Virus and Heparan Sulfate/Heparin*, Virology 218:35–42 (1996).

Trybala et al.; *Interaction Between Pseudorabies Virus and Heparin/Heparan Sulfate*, The Journal of Biological Chemistry 973:5047–5052 (1998).

Wickham et al.; *Adenovirous targeted to heparan–containing receptors increases its gene delivery efficiency to multiple cell types*, Nature Biotechnology 14: 1570–1573 (Nov. 1996).

Wickham et al.; *Integrins $\alpha V\beta 3$ and $\alpha V\beta 5$ Promote Adenovirus Internalization but Not Virus Attachment*, Cell 73:309–319 (Apr. 23, 1993).

Wickham et al.; *Integrin $\alpha V\beta 5$ Selectively Promotes Adenovirus Mediated Cell Membrane Permeabilization*, The Journal of Cell Biology 127:257–264 (Oct. 1994).

Williams et al.; *Specificity and Affinity of Binding of Herpes Simplex Virus Type 2 Glycoprotein B to Glycosaminoglycans*, Journal of Virology 71:1375–1380 (Feb. 1997).

* cited by examiner

DONOR 2 (−)

DONOR 1 (+)
LABELED VIRUS
HS

METHODS AND FORMULATIONS FOR MEDIATING ADENO-ASSOCIATED VIRUS (AAV) ATTACHMENT AND INFECTION AND METHODS FOR PURIFYING AAV

RELATED APPLICATION INFORMATION

This application is a divisional of U.S. patent application Ser. No. 09/228,203 filed Jan. 11, 1999 now U.S. Pat. No. 6,410,300, which claims the benefit of U.S. Provisional Application No. 60/071,210 filed Jan. 12, 1998, the disclosures of which are incorporated by reference herein in their entireties.

STATEMENT OF FEDERAL SUPPORT

This invention was made, in part, with government support under grant number HL51818 from the National Institutes of Health. The government has certain rights to this invention.

FIELD OF THE INVENTION

This invention relates to methods and formulations for mediating virus attachment and infection, and more particularly relates to methods and formulations for mediating adeno-associated virus attachment and infection.

BACKGROUND OF THE INVENTION

Adeno-associated virus (AAV) is a human parvovirus that infects a broad range of cell types including human, non-human primate, canine, murine, and avian. A member of the Parvoviridae family, AAV is a small non-enveloped single-stranded DNA virus of 20–25 nm which has an unique requirement for a helper virus (e.g., adenovirus or herpes simplex virus) to complete its lytic cycle (R. W. Atchison et al., (1965) *Science* 149:754; M. D. Hoggan et al, ((1966) *Proc. Natl. Acad. Sci. USA* 55:1457; J. L. Melnick et al., (1965) *J. Bacteriol.* 90:271). In the absence of helper virus, AAV still infects the target cell, but integrates into the host genome and establishes latency. Unique among eukaryotic DNA viruses, the AAV genome can integrate site specifically into human chromosome 19 (R. M. Kotin et al., (1990) *Proc. Natl. Acad. Sci. USA* 87:2211; R. J. Samulski et al., (1991) *EMBO J.* 10:3941; R. J. Samulski, (1993) *Curr. Opin. Genet. Dev.* 3:74; C. Giraud et al., (1994) *Proc. Natl. Acad. Sci. USA* 91:10039; C. Giraud et al., (1995) *J. Virol.* 69:6917). This property has drawn considerable attention to the potential use of AAV as a gene therapy vector, although little is known about the initial events of AAV infection (R. J. Samulski, (1995) Adeno-associated virus-based vectors for human gene therapy, p. 232–271. In K. M. Hui (ed.), Gene therapy: from laboratory to the clinic. World Scientific Publishing Co., Singapore, Singapore; C. McKeon et al., (1996) *Hum. Gene Ther.* 7:1615; D. M. McCarty et al, (1997) Adeno-associated viral vectors, p. 62–78. In M. Strauss and J. Barranger (ed.), Concepts in gene therapy. Walter de Gruyter, Bellin. N.Y.; R. J. Samulski, (1997) Development of adeno-associated virus as a vector for in vivo gene therapy, p. 197–203. In L. M. Houdebine (ed.), Transgenic animals: generation and use. Harwood Academic Publishers, Chur, Switzerland). In particular, the recombinant AAV or rAAV vector system is well characterized and is the subject of increasing development as a vector for gene delivery (see, C. McKeon et al. (1996) *Hum. Gen. Ther.* 7:1615). In general, AAV vectors are generated by deleting rep and cap genes and replacing them with genes intended for delivery into the cell. Additionally, producer cells that contain rep and cap may be used to package the gene therapy vectors into the AAV capsid particle (B. J. Carter, (1996) *Nature Biotechnology* 14:1725).

Despite this growing interest in AAV, the events that govern the initial AAV infection remain poorly understood. The primary event of any viral infection is attachment of virus to the host cell. A wide variety of cell surface molecules are now known to serve as viral attachment receptors. However, the mechanism by which AAV attaches to its host cell has heretofore not been delineated. AAV has a very broad host range and infects a wide variety of cell types, suggesting that the virus uses a ubiquitous receptor to mediate infection. Identification of the initial virus-host cell interactions necessary for efficient AAV infection is not only important for the general understanding of parvovirus infection, but also for the effective use of AAV as a gene therapy vector.

Although the initial events in the life cycle of AAV are not well understood, previous studies suggest that AAV infects cells through interaction with a specific host cellular receptor (H. Mizukami et al., (1996) *Virology* 217:124; S. Ponnazhagan et al., (1996) *J. Gen. Virol.* 77:1111). AAV appears to exhibit saturation binding to HeLa cells. In addition, cellular attachment of AAV is sensitive to trypsin treatment, suggesting a protein component is responsible for binding. Id The lack of knowledge concerning the receptor of AAV has introduced significant obstacles to the development of reliable techniques for both isolating and using AAV as a means for gene therapy. For example, purification of AAV is generally conducted using techniques that ultimately involve the use of a CsCl gradient. There are certain disadvantages in using these techniques, primarily because CsCl is toxic and thus requires special handling. It would be highly desirable to develop a milder and less dangerous means of isolating AAV viral particles.

An additional obstacle to the use of AAV as a reliable gene therapy vector has been the difficulty in infecting certain types of cells with the vector. Experiments in cultured cells have shown that AAV vectors are efficient for delivery of genes to both dividing and non-dividing cells. However, these experiments have also shown that the efficiency and both expression and metabolic activation may vary with the cell type and the physiological state of the cell (C. McKeon et al., (1996) *Hum. Gen. Ther.* 7:1615). In particular, progenitor or stem cells (e.g., bone marrow $CD34^+$ cells) have been found to be difficult to infect with the AAV vector. Additionally, in some cell types, persistence and expression of a heterologous gene carried by the vector are not well maintained. Finally, even when it is known that certain cell types are generally permissive to infection by AAV, is appears that there is diversity among individual cell donors as to whether or not any particular donor's cells will permit infection by the AAV vector. It would be highly desirable to have means for the effective infection of stem cells and rare cell types, as well as the means for introducing the AAV vector into cells that may not naturally express the AAV receptor, or may not naturally produce the molecular substituents necessary for the attachment and internalization of the virus.

Accordingly, there is a need in the art for improved methods and reagents for purifying AAV and rAAV vectors. In addition, there is a need in the art for methods of modifying the wild-type tropism of AAV vectors for use in gene therapy and for screening cells for permissiveness to transduction by AAV vectors.

SUMMARY OF THE INVENTION

The methods, AAV vectors, and formulations of the present invention are based on the surprising discovery that has identified cell surface heparin and heparan sulfate (HS) proteoglycan as the primary cellular receptors for AAV. It has also been discovered that AAV interacts specifically with cell surface heparin and heparan sulfate glycosaminoglycans (GAG), and not other glycosaminoglycans. Further, it has now been determined that the presence of HS GAG on the cell surface directly correlates with the efficiency by which AAV can infect cells.

Moreover, a role has been established for $\alpha_v\beta_5$ integrin in AAV infection. AAV virions physically interact with the $\beta_5$ subunit of $\alpha_v\beta_5$ integrin. Using genetically defined cell lines that either lack or express $\alpha_v\beta_5$, it has been demonstrated that cell surface expression of this integrin promotes AAV infection. The present investigations suggest that $\alpha_v\beta_5$ integrin acts to facilitate the internalization of AAV bound to cell surface heparin and HS proteoglycans into the cell. This is the first report of the involvement of an integrin in a parvovirus infection.

These discoveries have led to the development of methods and formulations that mediate the infection of a broad range of cell types with AAV, including cells that are typically non-permissive for infection by AAV. Additionally, these discoveries have led to the development of methods of purifying AAV using receptor-like molecules that bind to AAV, and methods of screening cell samples for their permissiveness to infection with AAV. Furthermore, these discoveries have elucidated new strategies for modifying the natural tropism of AAV, in particular, for use in gene therapy.

Accordingly, a first aspect of the present invention is a method of facilitating attachment of AAV to a cell, and infection of a cell by AAV, by contacting the cell with a soluble artificial receptor or soluble receptor-like molecule that mediates attachment and infection of AAV into the cell. This aspect of the invention is based on the observation that low concentrations of soluble heparin, HS and high molecular weight dextran sulfate enhance AAV infection. Heparin, HS, and other polyanionic molecules are known to attach to the cell surface. Therefore, exogenous heparin, HS, GAGs and other polyanionic molecules (preferably, heparin and HS) can mediate AAV attachment to and infection of cells that do not typically express heparin or HS on the cell surface (or that express these molecules at low concentrations).

The discovery that heparin and HS proteoglycans are the receptor for AAV has also led to the development of a further aspect of the present invention, which is a method of purifying and/or concentrating AAV. According to one embodiment, a receptor-like molecule is immobilized to a matrix to form a solid support that binds the AAV. Samples suspected of containing AAV are then contacted with the immobilized receptor-like molecules. The bound AAV is eluted (e.g., with a high salt wash) and collected. This method may be practiced in numerous alternative embodiments, for example, by affinity chromatography, by batch purification methods (e.g., with magnetized beads), or by immobilizing the receptor-like molecule to a polymeric surface such as a plate or a tube. As a further alternative, the matrix can be a material such as fiberglass, cellulose acetate, nitrocellulose, or nylon. Such matrices can be advantageously employed to bind AAV, e.g., for titering or purification for analytical purposes.

The receptor of AAV having been determined relates to the a further aspect of the present invention, which is a method of facilitating or enhancing attachment of AAV to a cell, thus increasing the efficiency of AAV infection into a cell. In one particular embodiment of this method, the AAV capsid is mutated using techniques known to those skilled in the art, such that the mutant AAV exhibits enhanced attachment to cellular receptors and thus may increase infectivity of the AAV into the cell. More particularly, at least one of the AAV binding sites for heparin/HS is mutated, such that binding is enhanced. According to another embodiment, binding of AAV to a cell is facilitated or enhanced by upregulating the expression of receptors (e.g., heparin or HS) on the surface of the cell. Exemplary compounds that upregulate cell surface expression of heparin and HS are transforming growth factored, sodium butyrate, and fibroblast growth factor.

A further aspect of the present invention is a method of inhibiting or preventing binding of AAV to a cell. In one embodiment of this method, the AAV is mutated using techniques known to one skilled in the art, such that binding of AAV is prevented or inhibited. In particular, at least one of the AAV binding sites for heparin and/or HS is mutated (e.g, by deletion or by replacing basic amino acids with neutral amino acids) such that binding of AAV to cell surface receptors is prevented or inhibited. In another embodiment of this method, a cell that naturally expresses the AAV receptor is treated with an enzyme or reagent that removes or alters the natural AAV receptor, such that AAV binding to the cell is prevented or reduced or the AAV receptor can no longer mediate infection of the cell by AAV. In yet another embodiment of this method, AAV virus is treated with molecules (e.g., heparin, HS, high molecular weight dextran sulfate, antibodies) that have been determined to block the interaction between AAV and the AAV receptor at concentrations effective to inhibit or prevent binding of AAV to the cell, compared to that which would occur in the absence of such treatment.

A further aspect of the present invention is a method of screening a cell for permissiveness to AAV infection by detecting the presence or absence, or alternatively, the abundance, of the AAV receptor on the cell surface. In this method, a cell or sample of cells is contacted with, for example, an antibody to the AAV receptor. Binding of the receptor to the antibody is then detected and visualized by techniques that are readily available to one skilled in the art. This method finds particular use in screening potential donors for cells that may be used in gene therapy, in screening recipients for permissiveness to gene therapy using an AAV vector, and in screening cells for potential use as producer cells for the AAV vector.

A further aspect of the present invention are formulations containing AAV vectors. In one embodiment, the present invention provides formulations useful in the mediation of cell attachment to, or infection by, AAV. The formulation contains an AAV vector along with a soluble receptor-like molecule or artificial receptor of the present invention, preferably in a physiologically or pharmaceutically acceptable carrier. The AAV vector in such a formulation may optionally contain mutations in the binding site for the receptor that enhance binding to the receptor. A second embodiment is a formulation useful in preventing or inhibiting binding of the AAV vector to a cell comprising an AAV vector along with a molecule that blocks binding of the vector to the natural receptor. This formulation will aid in specific targeting of AAV vectors. The AAV vector in such a formulation may optionally contain mutations in the binding site for the receptor that inhibit binding to the receptor. Formulations of the present invention may optionally contain certain additives such as stabilizers or protease inhibitors known to one skilled in the art. Furthermore, AAV vectors provided in formulations of the present invention may optionally comprise heterologous genes that are to be delivered into a target cell for the purpose of expressing the heterologous gene in the cell, e.g., for gene therapy.

A further aspect of the present invention is a kit for mediating AAV attachment to, and infection of, a cell. Such a kit will comprise an AAV vector along with at least one compound that mediates AAV attachment to and infection of a cell, preferably packaged together in a container with written instructions for using the kit.

A further aspect of the present invention is a kit for screening cell samples for permissiveness to AAV infection. Such a kit will comprise a first reagent that binds to the AAV receptor, such as an antibody to the receptor, along with a second reagent for detecting binding between the AAV receptor and the first reagent. The reagent that specifically binds to the AAV receptor and the detecting reagent are preferably packaged in a single container along with written instructions for using the components of the kit to determine if a cell sample is permissive for AAV attachment and infection.

A further aspect of the present invention is a method of enhancing the delivery and transduction of a heterologous gene into a cell, wherein the heterologous gene is delivered into a cell by an AAV vector. In such a method, the heterologous gene is carried by an AAV vector produced using methods known to those skilled in the art. In the present invention, the AAV vector is contacted with the target cell, wherein the target cell is exposed to a soluble receptor-like molecule or artificial receptor of the present invention. In an alternative embodiment, the AAV vector carrying the heterologous gene is contacted with the cell simultaneously with the soluble receptor like molecule.

The discovery that $\alpha_v\beta_5$ integrin serves as a co-receptor to facilitate infection by AAV is related to a further aspect of the invention, which is a method of facilitating or enhancing infection of AAV into a cell by treating the cell with a compound that induces or enhances the expression of integrin (preferably, $\alpha_v\beta_5$ integrin) on the surface of the cell. Illustrative compounds for upregulating cell surface integrin include cytokines (including interleukins, e.g., IL-1b), hematopoietic growth factors, (e.g., granulocyte-macrophage colony stimulating growth factor and macrophage colony stimulating growth factor), and phytohemagglutinin. As a further aspect, also provided are methods of screening a cell or cell sample for permissiveness to infection by AAV by detecting the presence or absence (or alternatively, the abundance) of integrin (preferably, $\alpha_v\beta_5$ integrin) expression on the surface of the cell(s). Also provided, as a further aspect, is a kit for determining if a cell is permissive for infection by AAV, where the kit provides reagents for detecting the presence or absence (or alternatively, abundance) of integrin (preferably, $\alpha_v\beta_5$ integrin) on the cell surface.

These and other aspects of the present invention will be set forth in more detail in the description of the invention below.

BRIEF DESCRIPTION OF THE DRAWINGS

As shown in FIG. 4A, fluourescently labeled AAV-2 was bound to wild type CHO cells (Panel I) and the pgsA-745 mutant that lacks proteoglycans (Panel II) as described in methods. Images were captured using confocal microscopy. FIG. 4B illustrates binding of $^3$H-AAV to parental and mutant CHO cells. Binding assays were performed at 4° C. in Eppendorff tubes. $3\times10^5$ cells were incubated with $4\times10^{11}$ particles of $^3$H-AAV for 90 minutes in HBS binding buffer. After thorough washing, cells were pelleted, solubilized and radioactivity quantitated as described in methods. Non-specific binding was determined by parallel binding studies done in the presence of 100 fold excess unlabeled virus. Data represent the mean specific binding and standard deviation obtained from experiments performed in triplicate.

FIG. 5A graphically illustrates AAV infection of wild type and mutant CHO cells deficient in proteoglycan synthesis. rAAV-LacZ virus was incubated with cells at an MOI of 10 for 1 hour at 37° C. Cells were harvested 44 hours post-infection and assayed for β-galactosidase activity. Data represent the mean and standard deviation of triplicate experiments. FIG. 5B illustrates UV treatment of wild type and mutant CHO cells and its effect on rAAV transduction. Cells were treated with 45 Joules/m$^2$ UV in a UV stratalinker (Stratagene) prior to infection with rAAV-LacZ as described above. β-galactosidase activity was measured as described for non-UV treated cells.

FIG. 9A, illustrates human bone marrow CD34$^+$ cells positive for both AAV virus binding (top graph) and heparan sulfate (bottom graph). Fluorescently-tabeled AAV or anti-heparan sulfate antibody (FITC) were incubated with cells for one hour at 4° C. Cells were washed three times and fixed in a 1% paraformaldehyde solution prior to FACS scan. The results are overlaid onto control samples with unlabelled virus or non-specific FITC-conjugated antibody. As is seen in FIG. 9A, cells that are positive for the AAV receptor cell surface heparan sulfate exhibit a shift in relative fluorescent value to the right (bottom graph), as compared to non-specific FITC conjugated antibody. Similarly, virus bound to the cell surface exhibit a spectroscopic shift to the right when compared to unlabelled virus. FIG. 9B illustrates a FACS analysis screen for cells that are negative for both cell surface heparan sulfate (i.e., antibody specific for heparan sulfate does not bind to the cell) and for AAV virus binding. When the control data are overlaid onto the experimental data, no fluorescent shift is observed.

DETAILED DESCRIPTION OF THE INVENTION

Figure 1A:
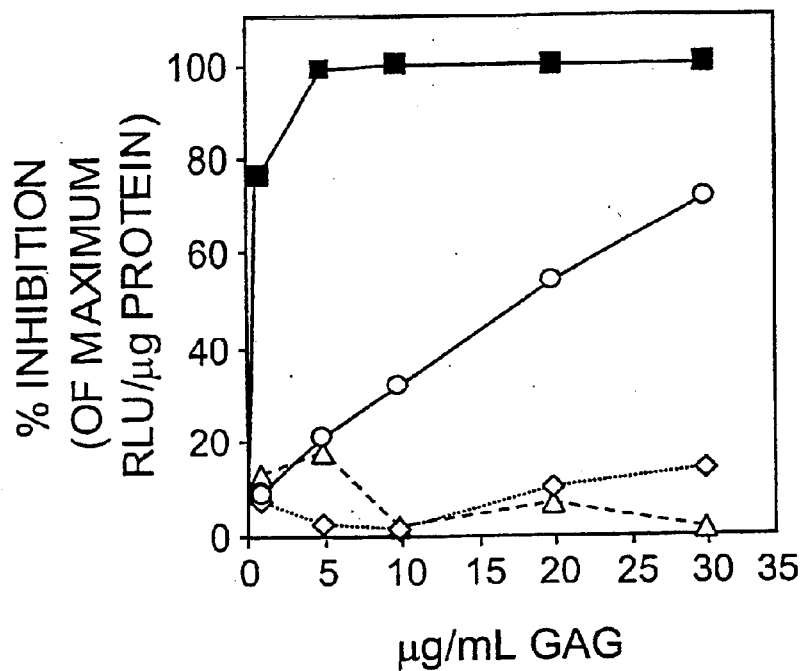
FIGS. 1A and 1B illustrate the inhibition of AAV infection by various glycosaminoglycans. In the data shown in FIG. 1A, rAAV was incubated with the indicated concentrations of heparin (solid squares), chondroitin sulfate B (dermatan sulfate) (open circles), chondroitin sulfate A (open diamonds) or chondroitin sulfate C (open triangles) for 1 hour at 37° C. prior to a 1-hour adsorption period of the virus/GAG mixture to HeLa cells for infection. β-galactosidase activity was assayed 44 hours post-infection using a Galacto-Light Plus kit (Tropix Inc.), and measured in a luminometer. Each point denotes the average % decrease in Relative Light Units (RLU) per ug of protein relative to the maximum RLU/μg protein obtained in experiments without GAG. In the data shown in FIG. 1B, HeLa cells were preincubated with increasing concentrations of heparin at 37° C. for 1 hour. After thorough washing, cells were infected with rAAV as described above. Data points represent the average % maximum RLU/ug protein obtained without heparin preincubation.

The present invention is based on the discovery that heparan sulfate proteoglycan (HSPG) functions as a cellular receptor for AAV. The broad range of cell types that are infected by AAV is likely attributable, at least in part, to the almost ubiquitous distribution of HSPG on cellular surfaces. While not wishing to be held to any particular theory of the invention, it appears that it is the HS moiety of cell-surface proteoglycans, rather than the protein core, that functions as a receptor. This binding mechanism is supported by the observation that (1) AAV will bind to a heparin column, (2) low-concentrations of soluble heparin will mediate AAV attachment and infection into cells that do not express HS proteoglycan on the cell surface, and which are normally non-permissive for AAV infection, and (3) high concentrations of soluble heparin will inhibit AAV binding, and subsequent infection, to cells that are normally permissive for AAV infection. Heparin and heparin proteoglycan also function as a receptor for AAV. Those skilled in the art, however, will understand that the distribution of heparin proteoglycan in vivo is currently believed to be limited to mast cells.

As used herein, a "cellular receptor for AAV" or "AAV receptor" is a molecule, typically on the cell surface, that binds AAV and/or mediates internalization of the bound AAV into the cell. Preferably, the receptor contains heparin or HS moieties, but may also contain other GAGs or post-translational modifications. Generally, the receptor is heparin or HS proteoglycan.

Heparin and HS (as well as proteoglycans containing these moieties), like other glycosaminoglycans (GAGs) are highly heterogeneous molecules. The repeating disaccharide unit of heparin/HS is comprised of alternating glucosamine and hexuronic acid monosaccharides. The hexuronic acid of heparin/HS can be either glucuronic acid or iduronic acid (glucuronic acid that has undergone $C_5$ epimerization of the carboxyl group). Heparin only differs from HS in that it contains relatively more iduronic acid, N-, and O-sulfation (for a review, see generally, R. L. Jackson et al., (1991) *Physiological Reviews* 71:481).

With the exception of hyaluronan, all GAGs are sulfated and covalently linked to a protein core to form proteoglycans. The core proteins can range in size from 10 kDa to as large as 600 kDa and may be modified by a single GAG moiety or a mixture of GAGs. Proteoglycans can be found in the extracellular matrix as well as associated with plasma membranes either as membrane spanning or glycosyl phosphotidylinositol anchored proteins.

Heterogeneity in GAG moieties can result from variations in chain length, different carbohydrate backbone sequences, and the pattern and degree of sulfation. It is currently of interest in the proteoglycan field whether specific GAG sequences mediate particular biological functions. With respect to the present invention, AAV exhibits a higher affinity for heparin than HS, and it appears that AAV preferentially binds to heparin/HS moieties containing a relatively higher degree of sulfation and/or a higher overall negative charge. AAV may bind preferentially to particular heparin/HS sequences or fractions. Such sequences or fractions can be isolated by standard methods in the art for use with the present invention. For example, in studies employing genetic mutants with defects in GAG synthesis, the present inventors have found that N-sulfated glucosamine appears to be an important determinant for AAV binding.

The present investigations have further identified $\alpha_v\beta_5$ integrin as a cellular co-receptor for AAV. It does not appear that $\alpha_v\beta_5$ integrin is a primary binding site for AAV, but rather facilitates internalization of bound AAV into the cell, for example, by targeting the bound AAV to coated pits.

Heparan sulfate proteoglycans are known to function as cellular receptors for several other animal viruses (Rostand et al., (1997) *Infect. Immun.* 65:1), including: herpes simplex virus (HSV) types 1 and 2 (Sheih et al., (1992) *J. Cell Biol.* 116:1273; WuDunn and Spear, (1989) *J. Virol.* 63:52), cytomegalovirus (Compton et al., (1993) *Virology* 193:834), dengue virus (Chen et al., (1997) *Nature Med* 3:866), and foot-and-mouth disease type O virus (Jackson et al., (1996) *J. Virol.* 70:5282). As far as the inventors are aware, there are no other reports of a virus that uses a two-step process for viral infection involving attachment to a primary HSPG receptor and subsequent mediation of virus entry by $=_v\beta_5$ integrins.

Interestingly, it has been posited that adenovirus (Ad) binds to host cells through the coxsackievirus adenovirus receptor (CAR), which complex is then internalized by interacting with $\alpha_v\beta_5$ integrin (J. M. Bergelson et al., (1997) *Science* 275:1320; T. J. Wicham et al., (19930 Cell 73:309). Likewise, HSV-1 has been demonstrated to bind to a HSPG receptor and then interact with a secondary HVEM (Herpes Virus Entry Mediator) receptor, which facilitates internalization of the bound virus (R. I. Montgomery et al., (1996) *Cell* 87:427; M. Sheih et al., (1992) *J. Cell Biol.* 116:1273). The shared features of the binding and internalization mechanisms of AAV with Ad and HSV may be of evolutionary significance as Ad and HSV are the most common helper viruses for producing a productive (i.e., lytic) AAV infection.

As used herein, the term "AAV" refers to adeno-associated virus in both the wild-type and the recombinant form (rAAV) and encompasses mutant forms of AAV. The term AAV further includes, but is not limited to, AAV type 1, AAV type 2, AAV type 3, AAV type 4, AAV type 5, AAV type 6, avian AAV, bovine AAV, canine AAV, equine AAV, and ovine AAV (see, e.g., BERNARD N. FIELDS et al., VIROLOGY, volume 2, chapter 69 (3d ed., Lippincott-Raven Publishers). In a preferred embodiment, the AAV used in the present invention is AAV Type 2. Alternatively, the methods of the present invention can be carried out with autonomous parvoviruses, including but not limited to: mouse minute virus, bovine parvovirus, canine parvovirus, chicken parvovirus, feline panleukopenia, feline parvovirus, goose parvovirus, and B19 virus. Other autonomous parvoviruses are known to those skilled in the art. See, e.g., BERNARD N. FIELDS et al., VIROLOGY, vol.2, chapter 69 (3d ed., Lippincott-Raven Publishers).

As used herein, "infection" of a cell by AAV means that the AAV enters the cell to establish a latent or active (ie., lytic) infection. See, e.g., BERNARD N. FIELDS et al., VIROLOGY, volume 2, chapter 69 (3d ed., Lippincott-Raven Publishers). In embodiments of the invention in which the AAV is administered to a subject, it is preferred that the AAV integrates into the genome and establishes a latent infection.

Except as otherwise indicated, standard methods may be used for the construction of rAAV vectors, mutant AAV, helper vectors, transiently and stably transfected packaging cells according to the present invention. Such techniques are known to those skilled in the art (see e.g., SAMBROOK et al., Molecular Cloning: a Laboratory Manual 2D ed. (Cold Spring Harbor, N.Y. 1989); F. M. AUSUBEL et al, Current Protocols in Molecular Biology (Green Publishing Associates, Inc. and John Wiley & Sons, Inc., New York).

I. Methods of Purifyinig and/or Concentrating Adeno-Associated Virus

The present invention provides a rapid, convenient and efficient method for purifying AAV, for example, from packaging cells. Moreover, the inventive methods are advantageous in that they provide a highly pure AAV preparation, relatively free of contaminating adenovirus, with a lower particle-to-infectivity ratio than is typically observed with conventional purification methods (e.g., separation over a CsCl gradient). These methods can also be used to concentrate AAV preparations (e.g., to produce a smaller sample volume or prior to drying down a sample of virus).

In particular, the instant invention provides a method of purifying AAV from a sample by contacting the sample containing the AAV to a solid support that includes a matrix to which an artificial receptor or receptor-like molecule that mediates AAV attachment is immobilized (e.g., attached, bound, adsorbed by covalent or non-covalent interactions). The sample can be any sample that contains, or is suspected of containing, AAV. The sample may be a crude sample (e.g., a lysed cell preparation), a partially-purified sample (e.g., the sample may be the result of ammonium sulfate precipitation, dialysis, density gradient purification, or any other purification method) or may be a relatively pure AAV preparation (ie., the method is practiced primarily for the purpose of concentrating or reducing the sample volume of the virus).

As used herein, a receptor-like molecule or artificial receptor that mediates attachment, mediates infection, or mediates internalization is a molecule that functions to permit AAV attachment to, infection of, or internalization into, a host cell, respectively. The contacting is carried out under conditions in which the AAV will bind to the immobilized artificial receptor or receptor-like molecule (e.g., low salt conditions). Typically, other components in the sample will be washed away from the AAV/receptor complex. The bound AAV is then eluted from the solid support and collected.

The terms "receptor-like molecule" and "artificial receptor" are used interchangeably herein to indicate molecules that function as receptors for AAV on the surface of the cell. Alternatively, a receptor-like molecule or artificial receptor is a molecule that can bind to AAV with high affinity (e.g., can compete with cellular receptors, such as heparin and HS proteoglycan, for binding to AAV). The receptor-like molecules and artificial receptors are polyanionic molecules, for example, cell-surface glycosaminoglycans (GAG) and proteoglycans (PG). In preferred embodiments, the receptor-like molecules are sulfated molecules. In more preferred embodiments, AAV receptor-like molecules and artificial receptors according to the present invention contain heparin, HS, dermatan sulfate (i.e., chondroitin sulfate B), or dextran sulfate (preferably high molecular weight dextran sulfate, e.g., average molecular weight greater than 5,000 Da, preferably greater than 15,000 Da) moieties. In more preferred embodiments, the receptor-like molecule will contain heparin or HS. The terms "receptor-like molecule" and "artificial receptor" also encompass particular heparin or HS sequences or fractions to which AAV preferentially binds, as described above. The receptor-like molecule may simply be sulfate groups (e.g., the virus will bind to a solid support of cellufine sulfate; C. M. Summerford et al., (1998) *J. Virology* 72:1438).

These receptor-like molecules may be isolated by methods known in the art or may be obtained commercially. Those skilled in the art will appreciate that in vivo, HS is almost ubiquitous on the cell-surface, whereas heparin is only known to be present on the surface of mast cells. As AAV exhibits very high affinity for both heparin and HS in vitro, however, both of these GAGs can be employed in carrying out the present invention.

In particular embodiments of the invention heparin, HS, dermatan sulfate, and/or dextran sulfate is immobilized to a matrix to create an affinity purification solid support. Alternatively, the GAG may be attached to a protein core, and the proteoglycan is immobilized to the matrix. It is more preferred, however, that the GAG moieties alone are employed to form the affinity support.

The immobilized AAV receptor-like molecule can be contacted with the sample containing AAV (or suspected of containing AAV) by any method known in the art. Preferably, the solid support is packed into a chromatography column, and the AAV is purified from the sample by affinity chromatography. Chromatography can be carried out using conventional columns or by HPLC (high performance liquid chromatography) or FPLC (fast protein liquid chromatography). Alternatively, the AAV in the sample may be contacted in solution with the solid support (e.g., in the form of beads, preferably magnetic beads) and purified by a batch method. Binding of AAV in solution to magnetic beads bearing AAV receptors is particularly useful for concentrating dilute AAV preparations.

All known methods for immobilization of molecules (e.g., by adsorption, by electrostatic interactions, by covalent bonds) and any suitable matrix available to those skilled in the art may be employed in carrying out the present invention (see, e.g., Methods in Molecular Biology, Protein Purification Protocols (Shawn Doonan ed., 1996)). Matrices for use according to the present invention encompass solid and semi-solid matrices. Exemplary matrices include beads formed from glass, silica, alumina, ground corn grits, cellulose, agarose, or CELITE™ (a commercially available form of diatomaceous earth). In particular embodiments, the beads are magnetized. Typically, the matrix is modified to bear reactive groups to facilitate the immobilization reaction. For example, primary amine groups can be attached to the matrix by using silanes for siliceous or alumnina-based supports. The attached primary amine groups are activated by glutaraldehyde or other activating agent prior to the addition of the ligand. Crosslinking of the covalently bound affinity ligand is optional.

Methods for forming heparinized matrices are known in the art and include both non-covalent and covalent coupling techniques. V. D. Nadkarni et al., (1997) *BioTechniques* 23:382; A. A. Farooqui et al., (1983) *Adv. Chromatogr.* 23:127; O. Larm, (1983) *Biomater. Med Devices Artif Organs* 11:161; R. J. Linhardt, Chemical and enzymatic methods for the depolymerization and modification of heparin, p. 385–401. In H. Ogura et al., (Eds.), Carbohydrates—Synthetic Methods and Applications in Medicinal Chemistry. Kodansha, Ltd., Tokyo; J. Liu et al., (1994) *J. Pharm. Sci.* 83:1034; V. D. Nadkarni et al., (1994) *Anal. Biochem.* 222:59–67). Heparin may be covalently coupled through aldehyde groups at the reducing end of heparin using reductive amination to amine-functionalized matrices or by reaction to matrices bearing hydrazido groups. Solid supports bearing receptor-like molecules according to the present invention may also be obtained commercially (e.g., Heparin-Agarose Type I; Sigma).

As a further alternative, an affinity support can be formed by immobilizing an antibody (e.g., monocolonal or polyclonal antibody or Fab fragment) to a matrix, where the antibody binds to a receptor-like molecule for AAV. In particular embodiments, the antibody is directed against the protein core or GAG moieties of a proteoglycan, more particularly, heparin, HS, dermatan sulfate, dextran sulfate and proteoglycans thereof. The receptor-like molecule is immobilized to the matrix through interaction with the antibody prior to contacting the solid support with AAV.

As yet a further alternative, the matrix may be a polymeric surface (e.g., a polystyrene, polypropylene, or polyethylene tube or plate) with the receptor-like molecule immobilized thereto. The matrix can also be a material such as fiberglass, cellulose acetate, nitrocellulose, or nylon. This embodiment most readily finds application in purifying and/or concentrating relatively small quantities of the virus for analytical and/or diagnostic purposes or for determining virus titers.

II. Methods of Facilitating or Enhancing AAV Infection Into Cells

The present invention also encompasses a method of facilitating or enhancing AAV infection into a host cell, in particular, cells that are not typically permissive for AAV infection including, but not limited to, bone marrow progenitor cells, airway epithelial cells, and megakaryocytes. By "permissive" for AAV infection, it is meant that the cell is susceptible to AAV infection. Alternatively stated, AAV naturally infects a cell that is permissive for AAV infection. Alternatively stated, this aspect of invention is advantageously employed with cells that express low or no cell-surface heparin or HS. The phrase "facilitating or enhancing infection of AAV" as used herein indicates that the level of AAV infection into the cell is increased above that which is observed in the absence of the inventive methods and reagents. For example, this aspect of the invention can be practiced with a cell that is typically non-permissive for AAV infection (e.g., bone marrow progenitor cells or airway epithelial cells) or it may be used to augment (e.g., by at least 25%, 50%, 75%, 100% or more) the normal level of infection seen in an AAV permissive cell.

Likewise, the present invention also provides a method of facilitating or enhancing attachment of AAV to a receptor or receptor-like molecule. The phrase "facilitating or enhancing attachment of AAV" as used herein indicates that the level of AAV attachment to the cell is increased above that which is observed in the absence of the inventive methods and reagents. This aspect of the invention can be advantageously practiced with a cell to which AAV typically does not bind in the absence of the inventive reagents and methods (e.g., bone marrow progenitor cells or airway epithelial cells), or it may be carried out to augment (e.g., by at least 25%, 50%, 75%, 100% or more) the level of AAV attachment to a cell that naturally binds AAV.

According to this embodiment, a cell is contacted with both a receptor-like molecule that mediates attachment and infection of AAV into the cell (as defined above) and with AAV. Optionally, and preferably, the cell is pre-incubated with the receptor-like molecule prior to contacting with AAV. Alternatively, the receptor-like molecule and the AAV can be combined together and then contacted with the target cell. Typically, this embodiment is carried out ex vivo with cells that have been removed from a subject and are then re-introduced back into the subject following treatment, but it may also be carried out on cells in vivo or in vitro.

While not wishing to be limited to any particular theory of the invention, it appears that the exogenous receptor-like molecule binds to cellular polyanion receptors and thereby tethers the AAV to the cell surface. The present observations in AAV are corroborated by studies in which HSV-1 infection into non-permissive sog9 cells (which cannot synthesize GAGs) is induced by incubating the cells with exogenous dextran sulfate (A. P. Dyer et al., (1997) *J. Virol.* 71:191).

There is no particular concentration of the receptor-like molecule or artificial receptor that is required to mediate AAV infection. Suitable concentrations can be readily determined by those skilled in the art and will vary with the receptor-like molecule and the host cell employed. In general, however, a biphasic response curve is expected, as combining high concentrations of the receptor-like molecule with AAV and cells will likely inhibit, rather than mediate, binding to the host cell (discussed in more detail below). In particular embodiments, nanogram quantities of heparin or HS per milliliter are added to host cells to mediate AAV infection (e.g., 0.1–100 ng/mL, 0.25–50 ng/mL, 0.5–25 ng/ml, or 1–10 ng/mL).

Alternatively, infection of AAV into a host cell may be facilitated or enhanced by exposing the host cell to a compound that induces or upregulates (i.e., enhances) the expression of cell surface AAV receptors, preferably, cell surface heparin, HS, and/or dermatan sulfate, more preferably cell surface heparin and HS, most preferably HS. Such compounds are known in the art and include but are not limited to, transforming growth factor A, acidic fibroblast growth factor, sodium butyrate, and fibroblast growth factor (i.e., basic FGF and acidic FGF). The host cell may or may not exhibit expression of the cell-surface receptor in the absence of the compound. By "induce" or "enhance" the expression of cell surface AAV receptors, it is intended that the presence of the AAV receptor on the cell surface is increased or upregulated by the compound.

III. Screening Methods

The discovery of a primary cellular receptor for AAV provides the basis for a method of screening cells for permissiveness to infection by AAV by detecting cellular expression of AAV receptors (e.g. by detecting RNA, DNA, protein, or enzymes involved in GAG synthesis). Preferably, this method is carried out by detecting the presence or abundance of the AAV receptor on the cell surface, in particular, the presence or abundance of heparin and/or HS. The method may be practiced to determine the presence or absence, or alternatively, the abundance of AAV receptors on the cell surface. The cell may be a cell in culture, a cell in a sample that has been removed from a subject, or a cell in a subject in vivo. Alternatively, the cell may be one that has been fixed and/or stained, as is known in the art. This aspect of the invention is advantageously applied to screen subjects and cells that are candidates for gene therapy for permissiveness to transduction by AAV vectors. For example, the present investigations have found that only a subset of the population has bone marrow CD34[+] stem cells that express cell surface HSPG and are infected by AAV. In one particular embodiment, the screening methods disclosed herein can be employed to identify those subjects that are candidates for gene therapy that express AAV receptors on their bone marrow stem cells.

IV. Methods of Inhibiting or Preventing Infection by AAV

The discovery of a primary cellular receptor for AAV has important implications for altering the natural tropism of the virus. The broad range of cells that are infected by AAV complicates the use of AAV vectors, in particular, for gene therapy. Identification of the AAV receptor creates the opportunity to limit the infectivity of AAV by interfering with the normal virus-receptor interaction. Accordingly, the instant invention provides methods of inhibiting or preventing infection of AAV into a cell. In general, this embodiment of the invention is practiced with cells that are permissive (as defined above) to infection by AAV. This embodiment may be advantageously carried out with AAV vectors that are targeted to cells by mechanisms other than by the cellular receptor disclosed herein. For example, the AAV vector may have acquired a new tropism by introduction of a mutation into the structure of the AAV capsid. Alternatively, the AAV vector may be targeted by means of an antibody (e.g., a bispecific antibody) or any other molecule that can target the virus to a cell.

The expression "inhibiting or preventing infection" and "prevents or inhibits the attachment", as used herein, indicates that the infection or attachment, respectively, of AAV into the host cell is reduced or diminished as compared with the rates of infection or attachment seen in the absence of the inventive methods or treatments. It is not necessary that AAV infection/attachment are completely abolished. In general, AAV attachment and/or infection will be reduced by at least 25%, 50%, 75%, 85%, 90%, 95%, 99% or more as compared with attachment and/or infection in the absence of the inventive methods and reagents.

In one particular embodiment, the present invention provides a method of inhibiting or preventing infection of a cell by AAV, which method involves contacting the AAV with a compound that inhibits or prevents attachment of AAV to a cellular receptor (as described above) prior to or concurrently with exposing the AAV to the cell. Preferably the cellular receptor contains heparin or HS moieties. It is also preferred that the AAV and the compound are pre-incubated together prior to contacting the AAV with the cell.

The compound can be any molecule that disrupts the interaction of AAV and the cellular receptor so as to inhibit or prevent the attachment and infection of AAV into the cell. Preferably, the molecule is a polyanion, more preferably it contains GAG moieties, more preferably still heparin, HS, dermatan sulfate, or high molecular weight dextran sulfate moieties, yet more preferably heparin or HS moieties. Alternatively, the compound can be an antibody (e.g., monoclonal or polyclonal antibody or a Fab fragment) directed against the AAV capsid. Methods of producing polyclonal and monoclonal antibodies against particular epitopes are known in the art. The antibody may specifically recognize the receptor binding site(s) on the AAV capsid or it may non-specifically interfere with receptor binding (e.g., by steric hindrance or by inducing conformational changes) by interacting with other sites on the capsid. As a further alternative, other techniques known in the art such as screening of a phage display library can be used to select for compounds that bind to the AAV receptor binding site(s) and interfere with AAV binding to the cellular receptor.

There is no particular concentration of the compound required to interfere with AAV infection. Suitable concentrations can be readily determined by those skilled in the art and will vary with the compound and the host cell. In particular embodiments, microgram quantities of heparin or HS per milliliter are added to host cells to inhibit AAV infection (e.g., 0.5–1000 μg/mL, 1–500 μg/mL, 2.5–250 μg/ml, or 5–100 μg/mL).

In another particular embodiment, an antibody (as described above) to the cellular receptor for AAV is employed to inhibit or prevent attachment and infection of AAV into the cell (e.g., anti-GAG antibody or anti-HS antibody). According to this embodiment, the cell is preferably exposed to the antibody prior to or concurrently with being contacted with the AAV. Preferably, the cell is pre-incubated with the antibody prior to being contacted with the AAV.

In another particular embodiment, the present invention provides a method of inhibiting or preventing infection of AAV into a cell by treating the cell with a reagent that alters or removes cellular receptors so that attachment of AAV thereto, and subsequent. infection into the cell, is inhibited or prevented. Preferably, the reagent is an enzyme that cleaves GAG, more preferably heparin or HS. Alternatively, the enzyme is a protease (e.g., trypsin). In the most preferred embodiments, the reagent is heparinase I or heparitinase. Alternatively, the reagent does not cleave the cellular receptor but alters the receptor such that binding of AAV thereto is inhibited or prevented.

V. AAV Vectors with Altered Binding to the AAV Cellular Receptor

Furthermore, now that a primary receptor for AAV has been identified, the tropism of the virus can be altered by modifying (i.e., mutating) the AAV capsid. The capsid structure can be modified to facilitate or enhance binding of AAV to the cellular receptor or to inhibit or prevent binding thereto. The AAV can be modified by introducing a mutation (s) into the Cap protein(s) by standard methods known in the art. Preferably, the mutation is in the receptor binding domain(s) on the AAV capsid. Those skilled in the art will appreciate that mutations outside of this region may also modify the attachment of AAV to the cellular receptor. The mutation may be a deletion or insertion mutation that ablates or disrupts the receptor binding domain. Alternatively, the mutation may be a substitution mutation that results in an increased or decreased affinity of the mutant AAV for the cellular receptor.

Several consensus sequences have been identified among ligands that bind to heparin/HS receptors. In general, heparin/HS appears to bind to sequences including clusters of basic amino acids. Illustrative consensus sequences include but are not limited to BBXB, BBBXXB, and $RX_7FRXKKXXXK$, where B is a basic amino acid, and X is any amino acid. Three sequences containing clusters of basic amino acids are present in the first 170 amino acid residues of the VP1 capsid protein of AAV type 2 as follows: $RX_5KKR$ at amino acids 116 to 124, $KX_4KKR$ at amino acids 137 to 144, and $KX_6RKR$ at amino acids 161 to 170 (AAV type 2 sequence and numbering as described by Srivastava et al., (1983) *J. Virology* 45:555, as modified by Ruffig et al., (1994) *J. Gen. Virology* 75:33 85, Muzyczka, (1992) *Curr. Topics Microbiol. Immunol.* 158:97, and Cassinotti et al., (1988) *Virology* 167:176). In addition, the consensus sequence ($RX_7FRPKRLNFK$) is found in the VP1 capsid subunit of AAV type 2 at amino acids 299 to 315. These sequences are present at homologous positions in the VP1 capsid protein of other AAV serotypes.

The heparin/HS consensus sequences are marked by an abundance of basic amino acids. Accordingly, in one particular embodiment of the invention, a mutant AAV with a reduced affinity to the cellular receptor is provided by deleting one or more of the basic amino acid residues in the consensus sequencers) or by substituting neutral (e.g., alanine) or acidic amino acid residues therefor. Likewise, an AAV with an increased affinity for the cellular receptor is provided by inserting or substituting additional basic amino acid residues into the consensus sequence.

Methods of facilitating or enhancing, or conversely inhibiting or preventing, the infection of AAV into a cell employing the mutant AAV described above are also encompassed by the present invention. These methods involve contacting a cell with a mutant AAV, where the mutation in the AAV facilitates and enhances, or conversely inhibits or prevents, the attachment of the mutant AAV to the cellular receptor, with corresponding effects on the infection of the mutant AAV into the cell.

VI. Targeted Gene Therapy

The various methods described above for altering AAV tropism by facilitating/enhancing and inhibiting/preventing attachment to the AAV cellular receptor can be used in conjunction to develop methods of targeting AAV vectors to particular host cells and to divert them away from others (e.g., for targeted gene therapy). For example, to target an AAV vector to bone marrow stem cells, a bone marrow sample can be removed from a subject and the cells sorted (e.g., by fluorescence activated cell sorting) to separate out the target cells. Any of the methods or reagents described above can be employed to facilitate or enhance infection of the desired target cells with the AAV vector. Concomitantly, any of the methods or reagents described above can be used to inhibit or prevent binding of the AAV vector to the other cells in the bone marrow sample prior to re-introducing the cells back into the subject. For example, the target cells can be treated with a low concentration of a receptor-like molecule that facilitates or enhances AAV attachment and infection prior to or concurrently with the AAV vector. The cells that are not to receive the AAV vector can be treated with an enzyme that cleaves heparin/HS prior to returning the cells back to the subject.

Applications of the present invention to gene therapy are discussed in greater detail hereinbelow.

VII. Methods of Facilitating or Enhancing AAV Infection Into a Cell by Upregulating Integrin and Screening Methods Related Thereto The finding that $\alpha_v\beta_5$ integrin is a co-receptor for AAV provides additional possibilities for facilitating or enhancing AAV infection into a host cell. In one embodiment of the invention, the infection of AAV into a cell is facilitated or enhanced by treating the cell with a compound that induces or enhances (i.e., increases or upregulates) expression of integrin by the cell (preferably the integrin are $\alpha_v$ integrins, more preferably $\alpha_v\beta_5$ integrin). Such compounds are known in the art and include, but are not limited to, cytokines (e.g. interleukins, in particular, IL-1b), phytohemagglutinin, granulocyte-macrophage colony stimulating factor, and macrophage colony-stimulating factors. The host cell may or may not exhibit expression of integrin in the absence of the compound. By "induce" or "enhance" the expression of integrin, it is intended that the presence of integrin on the cell surface is increased or upregulated by the compound.

The present invention also encompasses methods of screening cells for permissiveness to infection by AAV by detecting cellular expression of integrins, preferably $\alpha_v$ integrins, more preferably $\alpha_v\beta_5$ integrin (e.g., by detecting RNA, DNA or protein). Preferably the presence or abundance of integrin on the cell surface is detected, as described above for methods of screening for expression of AAV cellular receptors.

VIII. Kits

A kit containing the required components for screening cells for permissiveness to infection by AAV based on detection of the presence or abundance of the cellular AAV receptor and/or integrin can be assembled. In one embodiment, the kit comprises a first reagent that binds to the AAV cellular receptor and a second reagent that detects the binding of the first reagent to the AAV cellular receptor. Preferably the first reagent (e.g., an antibody) detects heparin and/or HS. Alternatively, a kit for screening cells for permissiveness to infection by AAV comprises a first reagent that binds to integrin (preferably, $\alpha_v$ integrins, more preferably, $\alpha_v\beta_5$ integrin) and a second reagent that detects the binding of the first reagent to the integrin.

The first and second reagents included in the kits of the present invention can be based on any suitable detection system known in the art for detecting the AAV cellular receptor or the integrin. Exemplary methods include double-antibody detection methods. The second reagent (ie., detecting reagent) can incorporate any detectable label known in the art including radioisotopes, chemiluminescence agents, enzymes that produce a visible reaction product, or gold particles. Preferably, the cells used in the inventive screening methods are intact cells. The kits of the present invention may optionally include reagents for fixing cells (e.g., paraformaldehyde).

Also provided is a kit for facilitating or enhancing infection of AAV into a cell comprising a receptor-like molecule that mediates attachment and infection of AAV into the cell and an AAV vector. The receptor-like molecule and the AAV vector may optionally be present in a physiologically or pharmaceutically acceptable carrier.

Further provided is a kit for titering AAV particles comprising the receptor (e.g., heparin or HS) immobilized to a polymeric surface (as described in detail hereinabove). The kit may further contain reagents for detecting the bound virus (e.g., antibody) as well as standard solutions containing a known concentration of virus particles for generating a standard curve.

The components of the kits described above are preferably packaged together in a common container, typically including instructions for performing selected embodiments of the invention described herein.

IX. Gene Transfer Technology

The present invention is also advantageously employed to facilitate or enhance delivery of a nucleic acid to a cell in vitro or in vivo, e.g., for gene therapy. In particular, the invention can be used to deliver or transfer nucleic acids to animal cells. According to this aspect of the invention, a cell is contacted with a receptor-like molecule that mediates AAV attachment and infection (as defined above) and with a rAAV vector carrying a nucleic acid to be delivered or transferred to the cell. The cell may be one that is normally non-permissive or permissive for AAV infection. Generally, however, this embodiment of the invention is practiced with cells that normally exhibit no, or a low level, of AAV infection (e.g., bone marrow progenitor cells, airway epithelial cells, megakaryocytes).

The rAAV vector carries at least one heterologous nucleic acid sequence to be delivered to the target cell. Those skilled in the art will appreciate that the rAAV genome can encode more than one heterologous nucleic acid sequence (e.g., two, three or more heterologous nucleic acid sequences), generally only limited by the packaging capacity of the virus capsid.

Heterologous nucleic acid sequence(s) for use according to the present invention include nucleic acids encoding peptides and proteins, preferably therapeutic (e.g., for medical or veterinary uses) or immunogenic (e.g., for vaccines) peptides or proteins. Therapeutic peptides and proteins include, but are not limited to, CFTR (cystic fibrosis transmembrane regulator protein), dystrophin (including the protein product of dystrophin mini-genes, see, e.g, Vincent et al., (1993) *Nature Genetics* 5:130), utrophin (Tinsley et al., (1996) *Nature* 384:349), clotting factors (Factor XIII, Factor IX, Factor X, etc.) and any other peptide or protein that has a therapeutic effect in a subject in need thereof. Alternatively, in particular embodiments of the invention, the nucleic acid of interest may encode an antisense nucleic acid, a ribozyme, or other non-translated RNAs, such as "guide" RNAs (Gorman et al., (1998) *Proc. Nat. Acad Sci. USA* 95:4929), and the like.

The present invention also provides methods and reagents useful for vaccination. The antigen can be presented in the AAV capsid, alternatively, the antigen can be expressed from a heterologous nucleic acid introduced into the recombinant AAV genome. Any imnmunogen of interest can be provided by the AAV vector. Immunogens of interest are well-known in the art and include, but are not limited to, immunogens from human immunodeficiency virus, influenza virus, gag proteins, cancer antigens, and the like.

The methods of the present invention provide a means for delivering heterologous nucleic acid into a broad range of host cells, including both dividing and non-dividing cells. The vectors, methods and pharmaceutical formulations of the present invention are additionally useful in a method of administering a protein or peptide to a subject in need thereof, as a method of treatment or otherwise. In this manner, the protein or peptide may thus be produced in vivo in the subject. The subject may be in need of the protein or peptide because the subject has a deficiency of the protein or peptide, or because the production of the protein or peptide in the subject may impart some therapeutic effect, as a method of treatment or otherwise, and as explained further below.

Gene transfer has substantial potential use in understanding and providing therapy for disease states. There are a number of inherited diseases in which defective genes are known and have been cloned. In some cases, the function of these cloned genes is known. In general, the above disease states fall into two classes: deficiency states, usually of enzymes, which are generally inherited in a recessive manner, and unbalanced states, at least sometimes involving regulatory or structural proteins, which are inherited in a dominant manner. For deficiency state diseases, gene transfer could be used to bring a normal gene into affected tissues for replacement therapy, as well as to create animal models for the disease using antisense mutations. For unbalanced disease states, gene transfer could be used to create a disease state in a model system, which could then be used in efforts to counteract the disease state. Thus the methods of the present invention permit the treatment of genetic diseases. As used herein, a disease state is treated by partially or wholly remedying the deficiency or imbalance that causes the disease or makes it more severe. The use of site-specific integration of nucleic sequences to cause mutations or to correct defects is also possible.

In general, the present invention can be employed to deliver any foreign nucleic acid with a biological effect to treat or ameliorate the symptoms associated with any disorder related to gene expression. Illustrative disease states include: hemophilias (e.g., hemophilia A and hemophilia B) and other clotting disorders, Gaucher's Disease, diabetes mellitus, cystic fibrosis (and other diseases of the lung), muscular dystrophies (e.g., Duchenne, Becker), diseases of the nervous system (e.g., Alzheimer's Disease, Parkinson's Disease, amyotrophic lateral sclerosis, epilepsy), retinal degenerative diseases (and other diseases of the eye), diseases of solid organs (e.g., brain, liver, kidney, heart).

The instant invention can also be employed to provide an antisense nucleic acid to a cell in vitro or in vivo. Expression of the antisense nucleic acid in the target cell diminishes expression of a particular protein by the cell. Accordingly, antisense nucleic acids can be administered to decrease expression of a particular protein in a subject in need thereof. Antisense nucleic acids can also be administered to cells in vitro to regulate cell physiology, e.g., to optimize cell or tissue culture systems. The present invention is also useful to deliver other non-translated RNAs, e.g., ribozymes or "guide" RNAs (see, e.g., Gorman et al., (1998) *Proc. Nat. Acad. Sci. USA* 95:4929) to a target cell.

Finally, the instant invention finds further use in diagnostic and screening methods, whereby a gene of interest is transiently or stably expressed in a cell culture system.

X. Subjects, Formulations, Vaccines and Modes of Administration

Disclosed herein are formulations comprising a receptor-like molecule that mediates attachment and infection of AAV into a cell and an AAV vector in a physiologically acceptable carrier. Also provided are formulations comprising a compound that inhibits or prevents attachment of AAV to cellular receptors and an AAV vector in a physiologically acceptable carrier. In general, a "physiologically acceptable carrier" is one that is not toxic or unduly detrimental to cells. Exemplary physiologically acceptable carriers include sterile, pyrogen-free water and sterile, pyrogen-free, phosphate buffered saline. Physiologically-acceptable carriers include pharmaceutically-acceptable carriers. By "pharmaceutically-acceptable" it is meant a material that is not biologically or otherwise undesirable, i.e., the material may be administered to a subject without causing any undesirable biological effects. Thus, a pharnaceutically-acceptable carrier can be used, for. example, in transfection of a cell ex vivo or in administering a viral particle directly to a subject. Further provided is a formulation comprising a mutant AAV vector (as described above) in a physiologically acceptable carrier.

The present invention finds use in veterinary and medical applications. Suitable subjects include both avians and mammals, with mammals being preferred. The term "avian" as used herein includes, but is not limited to, chickens, ducks, geese, quail, turkeys and pheasants. The term "mammal" as used herein includes, but is not limited to, humans, bovines, ovines, caprines, equines, felines, canines, lagomorphs, etc. Human subjects are the most preferred.

In particular embodiments, the present invention provides a pharmaceutical composition comprising a receptor-like molecule that mediates attachment and infection of AAV into a cell and an AAV vector in a pharmaceutically-acceptable carrier or other medicinal agents, pharmaceutical agents, carriers, adjuvants, diluents, etc. Also provided are formulations comprising a compound that inhibits or prevents attachment of AAV to cellular receptors and an AAV vector in a pharmaceutically acceptable carrier. Finally, also provided are mutant AAV vectors (as described above) in a pharmaceutically-acceptable carrier.

For injection, the carrier will typically be a liquid. For other methods of administration, the carrier may be either solid or liquid, such as sterile, pyrogen-free water or sterile pyrogen-free phosphate-buffered saline solution. For inhalation administration, the carrier will be respirable, and will preferably be in solid or liquid particulate form. As an injection medium, it is preferred to use water that contains the additives usual for injection solutions, such as stabilizing agents, salts or saline, and/or buffers.

Vaccines of the present invention comprise an immunogenic amount of infectious virus particles as disclosed herein in combination with a pharmaceutically-acceptable carrier. An "immunogenic amount" is an amount of the infectious virus particles that is sufficient to evoke an immune response in the subject to which the pharmaceutical formulation is administered. An amount of from about $10^3$ to about $10^7$ virus particles, and preferably about $10^4$ to $10^6$ virus particles per dose is suitable, depending upon the age and species of the subject being treated, and the immunogen against which the immune response is desired. Subjects and immunogens are as described above.

The present invention further provides a method of delivering a nucleic acid to a cell. For in vitro methods, the virus can be administered to the cell by standard viral transduction methods, as are known in the art. Preferably, the virus particles are added to the cells at the appropriate multiplicity of infection according to standard transduction methods appropriate for the particular target cells. Titers of virus to administer can vary, depending upon the target cell type and the particular virus vector, and can be determined by those of skill in the art without undue experimentation. Alternatively, administration of an AAV vector of the present invention can be accomplished by any other means known in the art.

The cell to be administered the virus vector can be of any type, including but not limited to neural cells (including cells of the peripheral and central nervous systems), retinal cells, gut and respiratory epithelial cells, muscle cells, pancreatic cells (including islet cells), hepatic cells, myocardial cells, bone cells (e.g., bone marrow stem cells), fibroblasts, endothelial cells, germ cells, and the like. Moreover, the cells can be from any species of origin, as indicated above.

In particular embodiments of the invention, cells are removed from a subject, the AAV vector is introduced therein, and the cells are then replaced back into the subject. Methods of removing cells from subject for treatment ex vivo, followed by introduction back into the subject are known in the art.

A further aspect of the invention is a method of treating subjects in vivo with an AAV vector. Administration of the AAV vector to a human subject or an animal in need thereof can be by any means known in the art for administering virus vectors. Exemplary modes of administration include oral, rectal, transmucosal, topical, transdermal, inhalation, parenteral (e.g., intravenous, subcutaneous, intradermal, intramuscular, and intraarticular) administration, and the like, as well as direct tissue or organ injection, alternatively, intrathecal, direct intramuscular, intraventricular, intravenous, intraperitoneal, intranasal, or intraocular injections. Injectables can be prepared in conventional forms, either as liquid solutions or suspensions, solid forms suitable for solution or suspension in liquid prior to injection, or as emulsions. Alternatively, one may administer the virus in a local rather than systemic manner, for example, in a depot or sustained-release formulation.

Dosages will depend upon the mode of administration, the disease or condition to be treated, the individual subject's condition, the particular virus vector, and the gene to be delivered, and can be determined in a routine manner. Exemplary doses for achieving therapeutic effects are virus titers of $10^8$–$10^{14}$ particles, preferably $10^{10}$–$10^{13}$ particles, yet more preferably $10^{12}$ particles.

In preferred embodiments, the rAAV vector is administered intramuscularly, more preferably by intramuscular injection or by local administration (as defined above). In other preferred embodiments, the rAAV vector is administered to the lungs.

The rAAV vector may be administered to the lungs of a subject by any suitable means, but are preferably administered by administering an aerosol suspension of respirable particles comprised of the AAV vector, which the subject inhales. The respirable particles may be liquid or solid. Aerosols of liquid particles comprising the AAV vectors may be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the inventive virus vectors may likewise be produced with any solid particulate medicament aerosol generator, by techniques known in the pharmaceutical art.

In summary, the reagents and methods of the present invention can be used to direct a nucleic acid to either dividing or non-dividing cells, and to stably express the heterologous nucleic acid therein. Using this vector system, it is now possible to introduce into cells, in vitro or in vivo, genes that encode proteins that affect cell physiology. The present invention is thus usefull in gene therapy for disease states or for experimental modification of cell physiology.

The invention will now be illustrated with reference to certain examples which are included herein for the purposes of illustration only, and which are not intended to be limiting of the invention.

The following abbreviations are used in the Examples: The term "Ab" means antibody, the term "Ad" means adenovirus, the term "bp" means base pair, the term "CHO" means Chinese Hamster Ovary, the term "cm" means centimeter, the term "$cm^3$" means cubic centimeter or milliliter, the term "CMV" means cytomegalovirus, the term "CsCl" means cesium chloride, the term "$dH_2O$" means de-ionized water, the term "$ddH_2O$" means distilled de-ionized water, the term "DI" means defective interfering (particle), the term "DMEM" means Dulbecco's modified Eagle's medium, the term "DMEM-H" means Dulbecco's modified Eagle's medium-high glucose, the term "dsDNA" means double-stranded DNA, the term "EDTA" means ethylenediaminetetraacetate, the term "EGTA" means ethylene glycol-bis(b-aminoethyl ether) N,N,N',N'-tetraacetic acid, the term "FACS" means fluorescence activated cell scanning, the term "FBS" means fetal bovine serum, the term "FITC" means fluorescein-isothiocyanate, the term "g" means gram, the term "GAG" means glycosaminoglycan, the term "h" means hour, the term "HBS" means HEPES-buffered saline, the term "HBSB" means HEPES-buffered Saline containing BSA, the term "HRP" means horseradish peroxidase, the term "HSPG" means heparan sulfate proteoglycan, the term "IMDM" means Iscove's modified Dulbecco's medium, the term "$k_d$" means dissociation constant, the term "kDa" means kilodalton, the term "L" means liter, the term "Lac-Z" means the gene expressing β-galactosidase, the term "LB" means Luria broth, the term "μg" means microgram, the term "μl" means microliter, the term "M" means molar, the term "mAb" means monoclonal antibody, the term "mCi" means millicurie, the term "mg" means milligram, the term "min" means minute, the term "ml" means milliliter, the term "mm" means millimeter, the term "mM" means millimolar, the term "MOI" means multiplicity of infection, the term "mu" means map unit, the term "ng" means nanogram, the term "PAGE" means polyacrylamide gel electrophoresis, the term "PBS" means phosphate-buffered saline, the term "pfu" means plaque forming unit, the term "rAAV" means recombinant adeno-associated virus, the term "RLU" means relative light unit, the term "rpm" means revolutions per minute, the term "SDS" means sodium dodecyl sulfate, the term "ssDNA" means single-stranded DNA, the term "TE" means Tris/EDTA, the term "TEMED" means N,N,N',N'- tetramethylene diamine, the term "TR" means (AAV) terminal repeat, the term "UV" means ultraviolet light, the term "wt AAV" means wild-type AAV, and the term "X-gal" means 5-bromo-4-chloro-3-indolyl-β-D-galactopyranosidase.

EXAMPLE 1

Reagents

GAG lyases; chondroitinase ABC, heparinase I, and heparinase III (heparitinase) were purchased from Sigma (St. Louis, Mo.). The soluble glycosaminoglycans heparin (from porcine intestinal mucosa), chondroitin sulfate A (from bovine trachea), chondroitin sulfate B (from porcine intestinal mucosa) and chondroitin sulfate C (from shark cartilage) were also purchased from Sigma. Chondroitinase AC was obtained from Seikagagku America Inc.

Plasmid SSV9 is a wt AAV-type 2 infectious DNA plasmid that contains the entire AAV-2 genome and has been described previously (Samulski et al., (1987), *J. Virol.* 61:3096). The rAAV vector plasmid, pAB-11, contains a β-galactosidase (LacZ) gene under control of the human cytomegalovirus (CMV) immediate early promoter. This is a transgene cassette which has been inserted between the AAV terminal repeats (TRs) (Goodman et al., (1994) *Blood* 84:1492). The pAAV/Ad helper plasmid contains the AAV rep and cap genes flanked adenovirus terminal repeats (Samulski et al., (1989) *J. Virol.* 63:3822). Plasmid pBHG10 is a non-infectious Ad plasmid that contains a deleted Ad type 5 genome. The Ad packaging signal and Ad E1 region have been removed from the wt Ad genome to prevent Ad replication (Bett et al., (1994) *Proc. Natl. Acad. Sci USA* 91:8802).

Monoclonal antibody A-20, which is an IgG antibody specific for intact AAV capsids (Wistuba et al., (1995) *J. Virol.* 69:5311) was kindly provided by Jurgen Kleinschmidt (Deutsches Krebsforschungszentrum, Germany). Two mouse monoclonal IgG1 antibodies against human integrin $\beta_5$ subunit were used; clone B5-IVF2 (Upstate Biotechnology Inc.) and B5-IA9. Clone B5-IA9, provided in the form of acites fluid, was used for immunoprecipitation and was a generous gift from Martin E. Hemler (Dana Farber Cancer Inst, Boston) and has been described previously (Pasqualini et al., (1993) *J. Cell Sci.* 105:101). Goat anti-mouse IgG conjugated to horseradish peroxidase (HRP) (Jackson Immuno-Research Laboratories Inc.) was used for chemiluminescence analysis in both western and viral overlay analysis. Mouse IgG1, produced from MOPC 21 tumor line, is provided in the form of clarified acites (Sigma) and was used as the isotype control antibody in immunoprecipitation and flow cytometry experiments. Monoclonal antibody P1F6 (Gibco/BRL) against $\alpha_v\beta_5$ purified from acites and goat anti-mouse IgG conjugated to fluorescein isothiocyanate (FITC) purchased from Caltag (Burlingame, Calif.) were used for flow cytometric analysis.

Monoclonal Ab HepSS-1 that recognizes heparan sulfate was purchased from Seikagaku America Inc. (Item #270246) and is an IgM antibody purified from acites. Mouse IgM antibody was purchased from Dako (item #X0942) and used as a negative control for the HepSS-1 mAb. Goat anti-mouse IgG (H+L) conjugated to fluorescein isothiocyanate (FITC) was purchased from Caltag and was used as the secondary antibody for detection of HS by flow cytometric analysis.

EXAMPLE 2

Virus and Cell Culture

HeLa, CHO-K1, and CHO-K1 mutants deficient in proteoglycan biosynthesis were obtained from the American Type Culture Collection (Rockville, Md.). HeLa cells were maintained in DMEM-H media supplemented with 10% fetal calf serum (FCS) and CHO cells were grown in Ham's F-12 media, 10% FCS.

The CS-1 (Farishian and Whittaker, (1979) *Arch. Biochem. Biophys.* 198:449) and CS1/β5 (Wicham et al., (1994) *J. Cell Biol.* 127:257) cell lines were generously provided by David Cheresh (Scripps Clinic & Res. Fndn.) with permission of Carolyn Damsky (University of California at San Francisco) and were propagated as previously described (Id.).

Mo7e cells were a generous gift from Chris Walsh (University of North Carolina at Chapel Hill) and were propagated in DMEM-H supplemented with 20% FBS and 5 u/ml human recombinant IL-3. Human 293 cells were obtained from ATCC and grown in DMEM-H supplemented with 10% FBS. The CD34+ cells were purified by the laboratory of Chris Walsh using immuno-selection. Recombinant AAV type 3 Lac-Z virus was obtained from the University of North Carolina vector core facility (Chapel Hill).

Wild type AAV-2, rAAV-LacZ, $^3$H-AAV-2, Cy3-AAV-2, Ad dl309, and rAd-LacZ were prepared according to methods previously described (Samulski et al., (1989) *J. Virol.* 63:3822; Snyder et al., (1996) Production of recombinant adeno-associated virus vectors, p. 12.1.1–12.2.23, in N. Dracopoli et al., (eds.), Current Protocols In Human Genetics. John Wiley & Sons Inc., New York). All virus preparations were purified by two successive bandings on CsCl gradients to ensure purity. Wild type AAV particle numbers were determined by protein quantitation (BCA reagent, Pierce) considering the molecular weight of an AAV virion is $4.5\times10^6$ g/mole. Recombinant virus titers were determined as described (Snyder et al., (1996) Production of recombinant adeno-associated virus vectors, p. 12.1.1–12.2.23, in N. Dracopoli et al. (eds.), Current Protocols In Human Genetics. John Wiley & Sons Inc., New York). For preparation of radiolabeled wt AAV, $3\times10^8$ HeLa cells were infected with wt AAV and Ad dl309 at MOIs of 10 and 5 respectively. $^3$H-methyl-thymidine (Amersham) was added 7 hours post-infection to a final concentration of 1 μCi/ml (Berns et al., (1970) *J. Virol.* 5:693). Labeled virus was purified 48 hours after infection as referenced and described above for wt AAV. $^3$H-AAV specific activity was approximately $4.0\times10^{-8}$ cpm/virion. Fluorescent Cy3 labeled AAV-2 was a gift from Dr. Jeff Bartlett (Gene Therapy Center, University of North Carolina at Chapel Hill).

EXAMPLE 3

Preparation of Plasmid DNA

Plasmid DNA was prepared by a modified alkaline lysis methods (Ausubel et al., (1995) Current Protocols in Molecular Biology, vol. 1 (K. Janssen, ed.). John Wiley & Sons, Inc., New York). Briefly, a 10 ml seed culture of bacteria containing the desired plasmid was grown to log phase under appropriate selection in Luria broth (LB) media. The seed culture was then used to inoculate 1 liter of LB media and the bacteria was grown to log phase in a 37° C. incubator, shaking at 250 rpm. The bacteria were harvested by centrifugation at 5,000 rpm for 10 minutes. The pellet was then washed with a solution of 50 mM Tris-HCl pH 8.0, 10 mM EDTA (solution I) before resuspension in 30 ml of wash solution (solution I). Next, 60 ml of freshly prepared solution II (0.2 M NaOH, 1% SDS w/v) was added. Solution II was mixed in by gentle inversion and the cells were incubated on ice for 15 minutes. This was followed by the addition of 30 ml ice cold solution III (3 M potassium, 5M acetate—prepared with potassium acetate, glacial acetic acid, and $H_2O$). The solution was again mixed by gentle inversion and incubated on ice for 15 minutes. After centrifugation at 5,000 rpm for 10 minutes at 4° C., the supernatant was filtered using cheese cloth. The clarified supernatant was mixed with 0.6 volumes (72 ml) of 2-propanol and incubated at room temperature for 5–10 minutes. The precipitate was then pelleted by centrifugation at 5,000 rpm for 5 minutes at 4° C., resuspended in 7 ml of $ddH_2O$, and transferred to a 50 ml tube. Next, an equal volume of solution IV (5 mM Tris-HCl pH 7.6, 5 M $LiCl_2$) was added and the solution was incubated on wet ice for 15 minutes. To pellet precipitated RNA, the solution was then centrifuged at 3,400 rpm for 5 minutes at 4° C. After transfer of the supernatant to a new tube, DNA was precipitated by addition of 2.5 volumes ethanol (35 ml) followed by an overnight incubation at −20° C. The DNA was then pelleted and washed in cold 75% ethanol. The pellet was allowed to air dry before resuspension in 10 ml of a 1.1 g/ml w/v CsCl solution containing 400 µl of a 10 mg/ml ethidium bromide solution.

The plasmid DNA was then purified by equilibrium density centrifugation. The DNA/CsCl mixture was centrifuged in a NVT65 rotor (Sorvall) at 65,000 rpm for four hours at 20° C. After centrifugation, plasmid DNA was removed with use of a syringe and a 21 gauge needle. The DNA was then placed on a second 1.1 g/mi CsCl equilibrium gradient using the centrifugation conditions described above. The ethidium bromide was then extracted from the purified plasmid using distilled $H_2O$ saturated with n-butanol. Next, to remove CsCl, the DNA was dialyzed at 4° C. against 8 liters of Tris-EDTA (10 mM Tris-HCl pH 8.0, 1 mM EDTA) using 2 liters of buffer at a time with three buffer changes. All DNA was quantified by measuring absorbance at 260 nm (1 OD absorbance unit is equivalent to 50 µg/ml double-stranded DNA). The quality of the DNA preparation was monitored by assessing the absorbance ratio of 260/280 nm (a value of 1.8 represents a pure preparation of DNA) and agarose gel electrophoresis.

EXAMPLE 4

Preparation of Adenovirus

Stock adenovirus was prepared by infecting ten 15 cm plates of 70–80% confluent 293 cells with Ad5 dl309 at an MOI of 10. At full Ad cytopathic effect (48–56 hours), cells were harvested, resuspended in 10 ml PBS (137 mM NaCl, 2.7 mM KCl, 4.3 mM $Na_2HPO_4$ 7 $H_2O$, 1.4 mM $KH_2PO_4$ pH 7.4) and subjected to three freeze-thaw cycles by alternating incubations in a dry ice/ethanol bath and a 37° C. $H_2O$ bath. The lysate was then centrifuged at 3000g for 5 minutes at 4° C. to remove cell debris. Five to six ml of the clarified supernatant was layered onto two 7 ml CsCl step gradients prepared in 12.5 ml Ultra-Clear centrifuge tubes (3.5 ml of a 1.4 g/ml CsCl in PBS under 3.5 ml of a 1.2 g/ml CsCl in PBS). The gradient was then centrifuged in a SW41 rotor for 1 hour at 30,000 rpm at 20° C. The lowest virus band was removed from each tube with a 5 ml syringe and a 21 gauge needle. Viral bands were combined and mixed with 1.3 g/ml CsCl solution to a final volume of 12 ml. This mixture was then overlaid onto 0.5 ml of a 1.5 g/ml CsCl solution placed in a 12.5 ml Ultra-Clear tube. After centrifugation overnight in a SW41 rotor at 30,000 rpm at 20° C., the adenovirus band was removed with a needle and syringe. The adenovirus preparation was then mixed with an equal volume of filter sterilized 2× storage buffer (10 mM Tris-HCl pH 8.0, 100 mM NaCl, 1 mM $MgCl_2$, 50% glycerol and 0.1% BSA) and stored in small aliquots at −20° C.

Adenovirus titer was determined by plaque assay. Eight-10 fold dilutions of the adenovirus preparation were made in 1 ml of DMEM without serum. One hundred µl of each dilution was used to infect 293 cells grown to 80% confluency in 60 mm dishes. Infection was allowed to proceed for 2 h before aspiration of media and addition of 5 ml plaque overlay solution previously warmed to 37° C. The plaque overlay solution consisted of a cooled (39° C.) autoclaved solution of 2% SEAPLAQUE™ low gelling temperature agarose made with distilled water that had been mixed with an equal volume of 2×DMEM (without phenol red) supplemented with 4% FBS, 25 mM $MgCl_2$, 0.3% sodium bicarbonate, 40 mM HEPES pH 7.5 and penicillin-streptomycin. The overlay solution was allowed to harden on the cells at room temperature before placement of cells in a 5% $CO_2$ 37° C. incubator. Cells were fed after five days by adding 2 ml of plaque overlay solution. Seven to eight days post infection plaques were counted to determine virus titer, taking into consideration the dilution factor used.

EXAMPLE 5

Preparation of wt AAV

For preparation of wt AAV, HeLa S3 cells were co-infected with adenovirus dl309 and a wt AAV seed stock. To prepare wt AAV seed stock, two 10 cm plates of 293 cells (seeded the night before at $5 \times 10^6$ cells/plate) were infected with adenovirus at an MOI of 5 in a 1 ml total volume of serum free media. After a 1 h incubation at 37° C. in a $CO_2$ incubator, cells were transfected with SSV9 wt AAV infectious plasmid DNA (15 µg/plate) using lipofectin, as described by the manufacturer. Transfection mixes were prepared with OPTIMEM™ media such that the transfection mix added per plate was 4 ml (total volume of 5 ml including Ad infection). Transfections were stopped after an 8–9 hour incubation by aspiration of media and addition of 10 ml fresh media containing 10% FBS. After 48 hours the cells and media were harvested and placed at −80° C. for later use. Virus from two 10 cm plates of seed stock is sufficient for infection of $1 \times 10^9$ cells.

For the large scale preparation of wt AAV, 3 L of HeLa S3 cells were grown in a 3 L spinner flask to a concentration of $5 \times 10^5$/ml. The wt AAV seed stock was subjected to 3 freeze-thaw cycles (alternating from a dry ice/ethanol bath to a 37° C. bath), spun to remove debris, and placed at 56° C. for 30 minutes to heat inactivate Ad. Prior to infection, HeLa S3 cells were harvested, resuspended in 100 ml of OPTIMEM™ media, and placed in a 150 ml spinner flask. Adenovirus, at an MOI of 5, and wt AAV seed stock were then added to the cells and infection was allowed to proceed for 1 hour at 37° C. Cells were then transferred to a 3 L spinner flask and the culture was brought up to 3 L with media containing 10% FBS. After incubation in a $CO_2$ chamber at 37° C. for 48 hours to allow for virus production, the cells were harvested, washed, and resuspended in PBS to a final volume of 45 ml. The cell suspension was then split equally into three 50 ml tubes, 15 ml/tube, and subjected to three freeze-thaw cycles followed by sonication with three 10–15 pulses at an output of 3, duty cycle 50. The resulting cell lysate was treated with 10 µg/ml DNAse and placed in a 37° C. $H_2O$ bath for 20 minutes. This was followed by addition of deoxycholate and trypsin to a final concentration of 2% and 0.02% respectively. After thorough mixing, the lysate was incubated for 20 minutes in 37° C. bath (mixing often during the incubation). The lysate was then homogenized by 20 strokes in a dounce homogenizer with a tight fitting pestle. Next, 10 g of CsCl/tube was added to 20 ml of lysate (volume brought up to 20 ml, if necessary, after addition of CsCl) before placement in a total of six 12.5 Ultra-Clear ultracentrifuge tubes (10 ml/tube). Tubes were then balanced with 1.4 g/ml CsCl and a continuous gradient was formed by centrifugation in a SW41 rotor at 40,000 rpm for 48 hours. Next, virus was extracted from the gradient with a needle, loaded on another continuous gradient of 1.4 g/ml CsCl (3 gradients), and centrifuged as above in a AH-650 rotor for 24 hours. AAV-2 settles at a density of 1.41–1.42 g/cm$^3$ in CsCl. Typically the measured refractive index of virus isolated from the CsCl gradient was between 1.3735 and 1.3740. Empty adenovirus was found at 1.298 g/cm$^3$ and infectious Ad at 1.362 g/cm$^3$ corresponding to refractive indexes of 1.3625 and 1.3680 respectively.

EXAMPLE 6

Preparation of $^3$H-labeled wt AAV

For preparation of radiolabeled wt AAV, 3×10$^8$ HeLa adherent cells (approximately 25 T75 cm$^2$ flasks at 80% confluency (1.2×10$^7$ cells/flask)) were infected with wt AAV seed stock and Ad dl309 at an MOIs of 5. Infections were performed in a total volume of 2 ml serum-free DMEM-H media/flask. The wt AAV seed stock was prepared from one 10 cm plate as described above. For infection, cells were incubated with virus at 37° C. for 1 hour, tilting every 15 minutes. DMEM-H media (2 ml), supplemented with 2% FBS, was then added per flask and the infection was allowed to continue for 6 hours (7 hours from initial infection). After 6 hours, 5 mCi of $^3$H-methyl-thymidine (Amersham) was added to 100 ml of DMEM-H media supplemented with 10% FBS and 4 ml of radioactive media was added per flask. The final concentration of $^3$H-methyl-thymidine in each flask was 25 µCi/ml. After 6–8 hours, 6 ml of 10% DMEM-H media was added/flask. The labeled virus was purified 48 hours after infection, as described above for wt AAV with several exceptions. First, cells were harvested in disposable tubes and all cells were resuspended in a total volume of 8 ml PBS. Second, after dounce homogenization, 6.2 grams of CsCl was added to approximately 9 ml of lysate and the volume was later brought up to 12 ml before distribution into three AH-650 rotor centrifuge tubes (4 ml/tube). Gradients were formed by centrifugation at 40,000 rpm in a AH-650 rotor for 24–36 hours after balancing the tubes with 1.4 g/ml CsCl. Virus was then removed, placed into two AH-650 tubes, balanced with 1.4 g/ml CsCl and subjected to another round of CsCl purification using the centrifugation conditions described above in Example 5.

EXAMPLE 7

Cy3 Labeling of AAV Virions

To prepare fluorescent labeled AAV, a CsCl preparation of wt AAV was dialyzed and adjusted to a concentration of 1.33×10$^{13}$ particles/ml (1 mg/ml) in 1 ml of 1.0 M sodium carbonate buffer, pH 9.3. One packet of Cy-Dye labeling reagent (Amersham, Cy-Dye FluoroLink reactive dye, Cy3.5 (PA23500) was then reconstituted with the dialyzed 1 mg/ml AAV stock. After confirming that all dye was dissolved, the mixture was incubated at room temperature for 30 minutes for conjugation. To purify the labeled AAV from unreacted dye, the mixture was dialyzed against at least 3 liters (1 liter at a time; 2 changes) of dialysis buffer (8.8 g NaCl, 2.0 g MgCl$_2$, 10 ml 1 M Tris-HCl, pH 7.8, 10% glycerol per liter) using a dialysis chamber (Slide-a-Lyser, 6,000–8,000 MW cutoff, Pierce Chem. Co.). Glycerol to 30% was then added to the conjugated virus and small aliquots of virus were stored at −20° C. until use. A dye to particle ratio was determined by reading the absorbance spectrum of labeled AAV and determining the dye concentration (per recalculated particle number) using the extinction coefficient for the Cy-Dye (provided by the manufacturer). AAV labeling ratios should be approximately 2 dye molecules per virion for the greatest sensitivity with the least effect on AAV physical properties. Cy3-AAV was then tested for its ability to be competed off cells with an excess unlabeled virus to ensure that the virions behaved like wt AAV. Cy3-AAV was further tested to ensure that the fluorescent virus showed the expected binding characteristics on the test cell lines: MO7e (negative control), and HeLa (positive control).

EXAMPLE 8

Preparation of rAAV-LacZ Made with Infectious Adenovirus rAAV was generated by a co-transfection/infection method using a modified calcium phosphate (CaPO$_4$) (Gibco-BRL) transfection method and Ad dl309. Briefly, human 293 cells were seeded in twenty 15 cm dishes the day before transfection (as to be 70–80% confluent the next morning) in DMEM-H (Gibco) containing 10% FBS (Gibco-BRL) with streptomycin and penicillin. Media was replaced with 25 ml of fresh IMDM media (Gibco-BRL) containing 10% FBS without antibiotics 3 h before transfection. Two transfection mixes were prepared each containing 250 µg AAV/Ad helper, 250 µg pAB-11 rAAV vector plasmid, 3 ml of 2.5 M CaCl$_2$, and ddH$_2$O up to 25 ml. Five ml of the DNA mix was then added to 5 ml of 2×HBS in a 15 ml polystyrene tube pipeting up and down three times to mix. After incubation for 1–5 minutes at room temperature, 5 ml of precipitate mixture was added dropwise to each of two 15 cm plates while swirling the media in the plates to ensure efficient coverage of cells. Cells were then placed at 37° C. in a 5% CO$_2$ chamber. This process was repeated additional times to complete transfection of all plates. After incubation for 8 hours, the cells were washed with IMDM media. Cells were then infected with Ad dl309 by first aspiration of wash media and then addition of 25 ml IMDM media (Gibco-BRL) supplemented with 10% FBS, antibiotics, and Ad dl309 equivalent to an MOI of 2.

To purify rAAV, the cells were harvested 48-hours post infection and the cell pellet was resuspended in 20 ml of OPTI-MEM™ media. Following three freeze-thaw cycles using a dry ice/ethanol bath and a 37° C. H$_2$O bath, the rAAV virus lysate was sonicated (40 bursts, 50% duty, power level 2). Debris was pelleted by centrifugation at 3000g for 5 minutes at room temperature. The supernatant was then transferred to a fresh tube and the cell debris pellet was resuspended in 20 ml of OPTI-MEM™ media and again sonicated. The second supernatant was clarified by centrifugation and pooled with the first supernatant. Undesired proteins were precipitated from the pooled supernatant by addition of one-third volume of ice cold saturated (NH$_4$)$_2$SO$_4$ (25% final volume) and incubation on ice for 10 minutes. Precipitated protein was removed by centrifugation at 8000 rpm in a SS34 rotor for 10 minutes at 4° C. To precipitate rAAV and adenovirus virions, two-third volume (volume=initial pooled supernatant) of ice cold saturated (NH$_4$)$_2$SO$_4$ (50% final) was added to the supernatant and the supernatant was incubated on ice for 20 minutes. After centrifugation in a SS34 rotor at 12,000 rpm for 20 minutes at 4° C., virus containing pellets were dissolved in a 20 ml total volume of 1.37 g/ml CsCl solution and centrifuged at 41,000 rpm in a SW41 rotor at 15° C. for 48 hours. Virus was then extracted with a needle and placed on a second CsCl gradient for 24 hours to ensure purity. rAAV-LacZ titers were determined by infecting 293 cells in the presence of Ad dl309 followed by staining at 24 h for β-galactosidase activity.

EXAMPLE 9

Preparation of rAAV-LacZ with Non-Infectious Ad Plasmid

Recombinant AAV-LacZ made without infectious adenovirus was purified and prepared as described in Example 8 except the Ad dl309 infection was omitted and a triple co-transfection was performed with pAB-11 rAAV vector plasmid, pAAV/Ad plasmid, and pBHGIO non-infectious Ad plasmid using the modified calcium phosphate (Gibco-BRL) transfection method described for the preparation of rAAV-LacZ using infectious adenovirus in Example 8. Transfections were performed with 2 µg pAB-11, 8 µg pAAV/Ad, and 15 µg pBHG10 per plate.

EXAMPLE 10

Staining Cells for β-Galactosidase Activity

Staining of cells for β-galactosidase activity was performed by a method described previously (Sanes et al., (1986) *EMBO J.* 5:3133). Typically, enzyme activity was assayed 24 h post infection for rAd-LacZ infections, or 48 h post infection for rAAV-LacZ infections performed without adenovirus unless otherwise indicated. Briefly, cells were washed in PBS and fixed in fixative containing 0.2% glutaraldehyde and 2% paraformaldehyde for 5 minutes at room temperature. Cells were then washed three times and overlaid with a staining solution (1 mg/ml 5-bromo-4-chloro-3-indolyl-β-D galactopyranoside (X-gal), 0.4 M MgCl$_2$, 1.64 mg/ml potassium ferricyanide, 2.12 mg/ml potassium ferrocyanide in PBS). The cells, overlaid with staining solution, were then placed in the dark at 37° C. for 12 h before counting those cells that stained blue.

EXAMPLE 11

Luminometer Assay for β-Galactosidase Activity

β-galactosidase activity was monitored in a luminometer by use of a Galacto-light Plus kit purchased from Tropix (Bedford, Mass.) as described by the manufacturer. In all infection experiments with rAAV-LacZ or rAd-LacZ vectors, cells were seeded the night before at the following densities: for 12-well dishes, 2×10$^5$ cells per well; for 12-well dishes, 5×10$^4$ cells per well; and for 48-well dishes, 3×10$^4$ cells per well. After infection proceeded for the indicated times, 50 µl of the provided lysis solution (Galacto-light Plus kit) was used to lyse cells in experiments performed in 48-well or 24-well plates and 100 µl of lysis solution was used for 12-well plates. The amount of lysate needed to assay enzymatic activity in the linear range was tested before assaying all samples. Generally 2–10 µl of lysate was assayed to keep the overall range of the experiment in the linear range of luminometer. A non-infected control lysate was used to monitor the background of the cell lysate. Before cell lysis, media was aspirated and cells were washed in PBS. The plates were then placed on ice and the appropriate amount of lysis solution was added to each well. Lysis was monitored by microscopy and was usually complete after incubation on ice for 10–15 minutes. Lysate was then transferred to Eppendorf tubes, ensuring complete transfer. To remove cell debris, the lysates were centrifuged at 4° C. then placed at −80° C. until use. Typically, lysate from one well was aliquoted into at least two tubes and one set placed at −80° C. to be reassayed if needed.

To assay enzymatic activity, enough reaction buffer for all assays was prepared and warmed to room temperature before use. A sealed-down version of the protocol provided by the manufacturer was performed using 100 µl of reaction buffer per assay. The reaction buffer consists of the provided "Galacton solution" diluted 100-fold in the provided Galacto-light reaction buffer diluent. The cell extract to be assayed (2–10 µl) was then aliquoted into polypropylene luminometer tubes, size 12×50 (Turner Designs, item #6185). In a timed fashion (i.e., every minute), 100 µl of the reaction buffer was added to each sample and allowed to incubate at room temperature for 1 h. During this time, the luminometer was set up as to inject 100 µl of provided accelerator solution per sample. After the 1-hour incubation, each reaction was assayed in a luminometer ensuring consistent timing between samples (addition of accelerator every minute). In some cases, enzyme activity was reported per pg of protein. To assess the protein concentration, 10 µl of lysate was quantitated in 96 well plates using 200 µl of BCA reagent (Pierce).

EXAMPLE 12

Binding Assays

All binding assays were done in a buffer which was determined to result in maximum cell viability, Hepes Buffered Saline containing 1% BSA (HBSB; virus binding buffer). For direct binding assays, $^3$H-labeled wtAAV-2 was incubated with cells either attached to plates or in suspension, as indicated, at a ratio of 4×10$^{11}$ particles/3×10$^5$ cells for 90 minutes at 4° C. in HBSB. Cells were then washed 3 times in ice cold HBSB to remove unbound virus, and were solubilized in 0.3 N NaOH. After neutralization with glacial acetic acid, cell-associated radioactivity was quantitated in a scintillation counter. For inhibition studies, and after enzymatic treatments, $^3$H-AAV was bound to adherent HeLa cells. Binding to wild type CHO and CHO cell mutants was done with suspended cells. Cells were first detached with 10 mM EDTA followed by two washes in Phosphate Buffered Saline (PBS) containing 8.8 mM CaCl$_2$ and 0.5 mM MgCl$_2$ and followed by one wash in HBSB before binding of $^3$H-AAV. Non-specific binding was determined in the presence of 100-fold excess unlabeled wt AAV (previously dialyzed in HBS, 10% glycerol). Binding of Cy3-labeled virus was done on wild type CHO and pgsA-745 cells grown on coverslips. After fixation in 4% paraformaldehyde for 20 minutes at room temperature, cells were mounted on slides and bound Cy3 labeled virus was detected by confocal microscopy. Images were obtained with an argon krypton laser at an excitation of 565-nm, a pinhole setting of 0.97 airy disk, a 585-nm dichroic reflector, and a 590-nm long pass barrier filter using Bio-Rad MRC-600 laser scanning attachment.

EXAMPLE 13

Viral Infection Assays

Inhibition assay:
rAAV-LacZ at an MOI of 2 was incubated in DMEM-H media in the presence or absence of indicated soluble GAGs at 1.0, 5.0, 10, 20, 30 µg/ml for 1 h at 37° C. For infection, rAAV-LacZ or the virus/GAG mixture was incubated with $2\times10^5$ HeLa cells for 1 h at 37° C. in a 5% $CO_2$ chamber. To stop the adsorption process, cells were washed thoroughly and overlaid with DMEM-H media supplemented with 2% FCS. After 44 h, cells were washed in PBS and lysed with 100 mM potassium phosphate pH 7.8, 0.2% Triton X-100. β-galactosidase activity was then assayed using a Galacto-Light Plus kit (Tropix Inc., Bedford, Mass.) as described by the manufacturer. Data was collected in a luminometer within the linear range of the assay and enzyme activity is expressed as Relative Light Units (RLU)/ug of protein. Each experimental condition was done in duplicate and independent experiments yielded similar results. Preincubation studies were performed as above except HeLa cells were incubated with or without indicated concentrations of heparin in DMEM-H media for 1 at 37° C. and washed thoroughly prior to rAAV-LacZ infection.

Enzymatic treatment:

GAG lyases were reconstituted in phosphate buffered saline (PBS). For enzymatic digestion of cell surface GAGs, $3\times10^4$ HeLa cells were washed and incubated with the indicated concentrations of GAG lyases in PBS containing 0.1%BSA, 0.2% gelatin and 0.1% glucose (digestion buffer) for 1 hour at 37° C. in a 5% $CO_2$ chamber. Cells were then washed four times with digestion buffer and subjected to rAAV infection as described above. Prior to use, each enzyme was tested for activity by a standard method used to determine specific activity of GAG lyases, except that enzyme activity was monitored under the conditions used for digestion, PBS pH 7.4 at 37° C. (Linhardt, (1994) Analysis of glycosaminoglycans with polysaccharide lyases, p. 17.13.17–17.13.32. in K. Janssen (ed.), Current Protocols in Molecular Biology, vol. 3. John Wiley & Sons, Inc., New York). Cells remained attached to the plate after all enzymatic treatments. Each experimental condition was performed in triplicate. β-galactosidase activity was assayed as described above with respect to the inhibition assays and is expressed in RLU. Enzyme concentrations are expressed in International Units (IU) per milliliter (one IU is equivalent to 600 Sigma units).

CHO cell infection and UV treatment:

For UV treatment, $3\times10^4$ CHO cells were washed, overlaid with PBS, and treated with 45 Joules/$m^2$ ultra-violet irradiation in a UV Stratalinker (Stratagene, La Jolla, Calif.) prior to rAAV infection (Ferrari et al., (1996) J. Virol. 7:3277). rAAV infections, at an MOI of 10, for both UV treated and non-UV treated CHO cells were performed as described above with respect to the inhibition assays. β-galactosidase activity is expressed as the average RLUs from rAAV infections performed in triplicate.

EXAMPLE 14

AAV Binding and Infection are Inhibited by Soluble Glycosaminoglycans

Following the initial observation that AAV binds to a cellulofine sulfate column (data not shown), the possibility that AAV may use cell surface proteoglycans to mediate infection was evaluated. If AAV infection initiates through interaction with cell surface proteoglycans, one or more of the major glycosaminoglycans (GAGs) found on membrane-associated proteoglycans should act as competitive inhibitors of AAV infection and binding. To test this possibility, we performed competition experiments with several known GAGs found on membranes. In this assay, we analyzed the ability of four soluble GAGs (heparin, chondroitin sulfate A, chondroitin sulfate B, and chondroitin sulfate C) to inhibit rAAV-Lac-Z reporter gene transduction in HeLa cells.

Increasing concentrations of GAGs were incubated with rAAV prior to adsorption to cells at 37° C. for 1 h. Cells were harvested 44 hours, post-infection and assayed for β-galactosidase activity. Of the four GAGs tested, heparin, a molecule chemically very similar to heparan sulfate (HS) GAG, inhibited AAV infection maximally and in a dose-dependent manner (FIG. 1A). Heparin concentrations as low as 5 μg/ml resulted in nearly 100% inhibition. Chondroitin sulfate B, which shares the most structural similarity to heparin/HS, exhibited 71% inhibition at 30 μg/ml. In contrast, concentrations up to 30 μg/ml of chondroitin sulfate A and chondroitin sulfate C exhibited no significant effect, with less than 20% inhibition. The observed inhibition was specific for AAV since similar studies had no effect on adenovirus infection, another non-enveloped DNA virus whose receptor is coxsackie adenoviral receptor (CAR) (data not shown) (Bergelson et al., (1997) Science 275:1320).

Figure 1B:
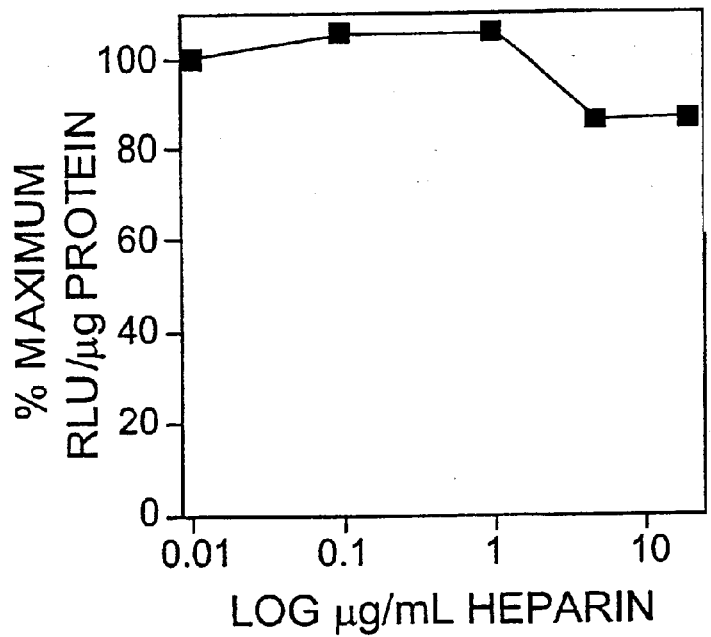

To rule out the possibility that significant inhibition of AAV infection by heparin was due to an induced cellular effect of this molecule on HeLa cells, preincubation studies were performed (FIG. 1B). HeLa cells were incubated with the indicated concentrations of heparin, washed extensively, and than infected with rAAV as described above. Unlike competition experiments, preincubation of HeLa cells with heparin had little effect on the ability of rAAV to transduce cells (FIG. 1B). While the presence of heparin (5 μg/ml) during viral adsorption demonstrated 100% inhibition (FIG. 1A), preincubation with heparin demonstrated less than 20% inhibition at concentrations up to 20 μg/ml (FIG. 1B). These data suggest that heparin interacts directly with AAV and inhibits an early event of viral infection.

Figure 2:
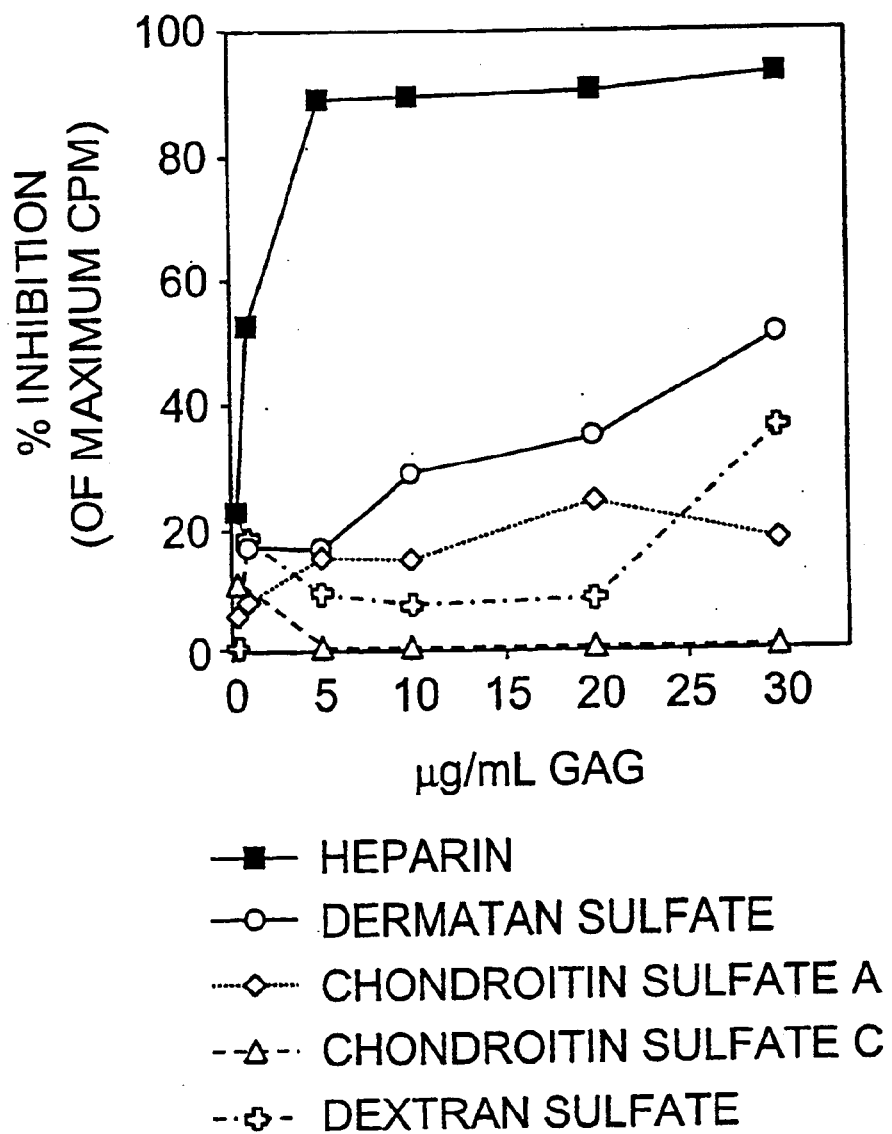
FIG. 2 illustrates that soluble heparin inhibits binding of AAV to the cell surface. After pre-incubation of 3H-wt AAV-2 with increasing concentrations of the indicated GAGs or the GAG analogue dextran sulfate, labeled virus was adsorbed to HeLa cells for 90 minutes at 4° C. Unbound virus was removed by three washes with ice cold binding buffer and radioactivity was quantitated as described in methods. Data is represented as the average % inhibition relative to the CPM bound in the absence of soluble GAG.

To further examine the observed specificity and to determine whether GAGs were inhibiting binding of the AAV virions to the cell surface, $^3$H-wt AAV was incubated with GAGs (heparin, dermatan sulfate, chondroitin sulfate A, chondroitin sulfate C, dextran sulfate) at various concentrations. After incubation with cells, the mixture was washed and cells were solubilized to quantify bound virus. By this assay, heparin (5 μg/ml) inhibited 90% of AAV binding (FIG. 2) correlating with rAAV transduction data (FIG. 1A). Furthermore, chondroitin sulfate B (dermatan sulfate, 30 μg/ml) inhibited binding by 51% (FIG. 2, circles). As expected, chondroitin sulfate A and C at similar concentrations did not significantly affect the ability of virus to bind to HeLa cells, exhibiting no more than 20% inhibition. These data suggest that heparin inhibits AAV infection by interfering with virion binding to the cell surface, presumably by competing for structurally related HS moieties.

Since heparin is known to be modified by more sulfate groups and has a higher charge density than the chondroitin sulfates (Ruoslahti (1989) J. Biol. Chem. 264:13369), it was important to determine whether inhibition by heparin reflected specificity or was simply a function of charge. The ability of a highly sulfated GAG analogue, dextran sulfate (MW 5,000), to act as a competitive inhibitor was examined. At the maximum concentration, 30 μg/ml, the observed inhibition by dextran sulfate was only 36% (FIG. 2) indicating that more than charge ratio is responsible for the inhibition of AAV by heparin and chondroitin sulfate B. Together, the above data support the hypothesis that AAV binds to cell surface proteoglycan, that this interaction is important for a productive infection, and that AAV exhibits specificity for particular GAG moieties.

EXAMPLE 15

AAV Requires Glycosaminoglycans On The Cell Surface For Infection

Since some GAGs are known to bind to specific cell surface receptors (Jackson et al., (1991) *Physiol. Reviews* 71:481), the above experiments could not completely rule out competition for a common receptor as a mechanism for inhibiting virus binding. To address this issue, enzymes that are known to specifically digest the GAGs present on the cell surface were used before assaying virus specific binding. Heparinase I and heparitinase cleave distinct linkages found in heparan sulfate Chondroitinase ABC cleaves at a linkage found in all chondroitin sulfates, including dermatan sulfate (chondroitin sulfate B), and chondroitinase AC cleaves only chondroitin sulfate type A and C (Linhardt (1994) Analysis of glycosaminoglycans with polysaccharide lyases, p. 17.13.17–17.13.1.32, in K. Janssen (ed.), Current Protocols in Molecular Biology, vol.3. John Wiley & Sons, Inc., New York). All enzymes were tested prior to use for activity and assayed with identical conditions used in the experiments described herein.

Figure 3A:
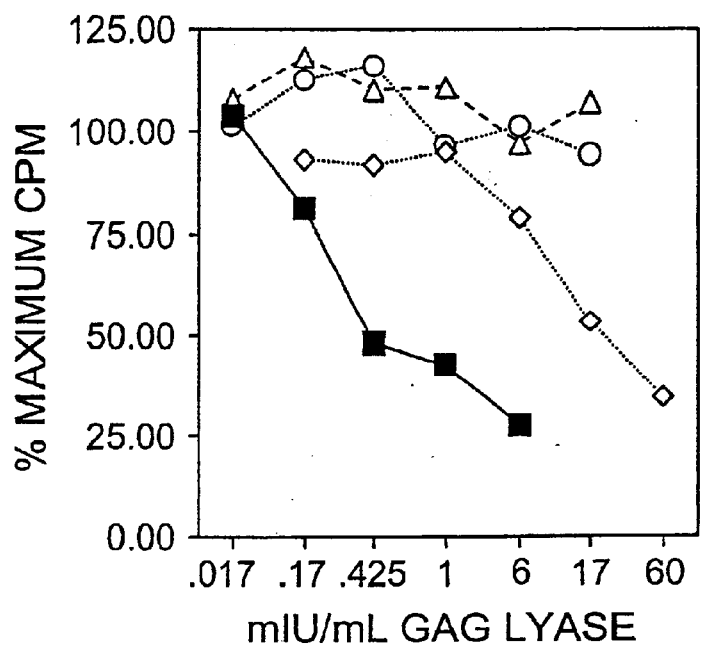
FIGS. 3A and 3B illustrate the effect of enzymatic digestion of cell surface glycosaminoglycans on AAV binding and infection. In the data shown in FIG. 3A, HeLa cells were treated with the indicated concentrations of the following GAG lyases: heparitinase (solid squares), heparinase I (open diamonds), chondroitinase ABC (open circles), or chondroitinase AC (open triangles), as described in Example 13, below. After thorough washing, the ability of AAV to bind the cell surface was assessed as described in Example 12, below. Data points represent the average % reduction in AAV binding relative to AAV binding obtained without enzymatic treatment. In the data shown in FIG. 3B, HeLa cells were treated with heparitinase or heparinase I as described herein. After thorough washing, rAAV was incubated with cells for a I hour adsorption period at 37° C. Cells were harvested 44 hours post-infection and assayed for β-galactosidase activity. Results are shown as the average % reduction in AAV transduction relative to transduction observed in the absence of enzymatic treatment. Data points represent the mean and standard deviation of experiments performed in triplicate.

Subconfluent HeLa cells were treated with various concentrations of each specific enzyme and assessed for $^3$H-AAV binding. Consistent with early experiments, enzymatic treatment with either heparitinase or heparinase greatly reduced the ability of virus to bind the cell surface; 73% and 66% respectively at the maximum concentration of enzyme tested (FIG. 3A). Further, chondroitinase ABC and chondroitinase AC treatment did not result in any reduction of AAV binding to HeLa cells (FIG. 3A). These data support that heparan sulfate proteoglycan (HSPG) mediates attachment of AAV to the cell surface.

The fact that ten-fold more heparinase as compared to heparitinase was required to obtain similar reduction of AAV binding was likely due to its known lower enzymatic activity under the conditions used (Linhardt (1994) Analysis of glycosaminoglycans with polysaccharide lyases, p. 17.13.17–17.13.1.32, in K. Janssen (ed.), Current Protocols in Molecular Biology, vol. 3. John Wiley & Sons, Inc., New York). Further, to ensure protease contaminants were not responsible for reduction in AAV binding, digestion in the presence of soluble substrate was performed. Exogenous addition of soluble heparan sulfate reversed the effect of heparitinase treatment on AAV binding to HeLa cells presumably by competing with the cell-surface HS for cleavage by lyase (data not shown). Therefore, specific removal of plasma membrane-associated heparan sulfate moieties results in a diminished ability of AAV to bind the cell surface. It was unexpected that chondroitinase ABC did not have any effect on AAV binding since the presence of soluble chondroitin sulfate B (dermatan sulfate) was able to inhibit AAV transduction and binding to HeLa cells, albeit much less efficiently than heparin. The lack of reduction in binding after enzymatic treatment with chondroitinase ABC suggests that AAV does not efficiently bind to dermatan sulfate present on the cell surface.

The above data thus rules out the possibility that. in the co-incubation experiments, soluble heparin and AAV were competing for a similar receptor or that heparin was sterically hindering binding to something other than membrane-associated GAGs. Instead, the data supports that AAV binds to cell surface proteoglycan and further suggests that this interaction is specific for heparan, not chondroitin, sulfate moieties.

Figure 3B:
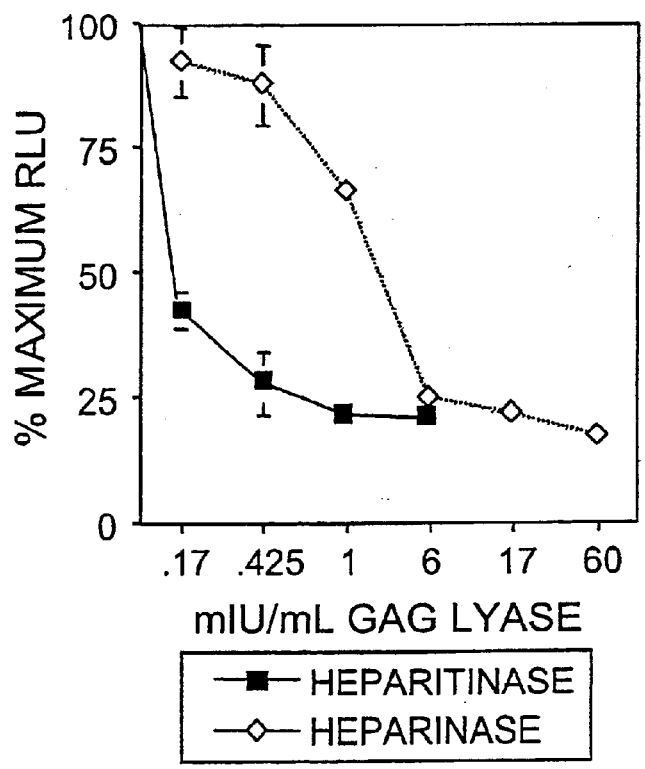

To demonstrate the biological relevance of AAV binding to cell surface heparan sulfate, we determined whether removal of HS moieties rendered cells less susceptible to AAV infection. We examined the ability of rAAV-LacZ to transduce HeLa cells after treatment with various concentrations of heparitinase or heparinase. rAAV transduction was reduced by 80% compared to untreated control cells (FIG. 3B). Importantly, as little as 0.425 mIU/ml heparitinase resulted in up to 72% reduction of AAV infection. Consistent with inefficient heparinase enzyme activity under these conditions, approximately ten-fold more enzyme was required for a similar reduction in AAV transduction. The reduced susceptibility of HeLa cells to AAV infection after enzymatic removal of membrane-associated HS GAG indicates a significant role for HSPG in AAV infection.

EXAMPLE 16

Mutants of the Glycosaminoglycan Synthesis Pathway Inhibit AAV Binding

CHO-cell derivatives defective in GAG synthesis were utilized to further define the requirement for heparan sulfate moieties for AAV infection. These mutant cell lines have defined deficiencies in the production of specific GAGs. Cell line pgsA-745 lacks xylosyltransferase, an enzyme necessary for the initiation of all GAG synthesis, and does not produce detectable levels of proteoglycans (Esko et al., (1985) *Proc. Natl. Acad. Sci USA* 82:3197). Mutant pgsB-618 has a defect in the galactosyltransferase I gene and makes about 15% the normal amount of proteoglycan synthesized by wild type cells (Esko et al., (1988) *Science* 241:1092; Esko et al., (1987) *J. Biol. Chem.* 262:12189). Cell line pgsE-606 is partially deficient in heparan sulfate N-sulfotransferase and produces an undersulfated form of HSPG (Bame et al., (1989) *J. Biol. Chem.* 264:8059; Bame et al., (1991) *J. Biol. Chem.* 266:10287). Finally, mutant pgsD-677 has a single mutation that affects both N-acetylglucosaminyltransferase and glucuronosyltransferase activities that are necessary for the polymerization of heparan sulfate disaccharide chains, and does not synthesize any HSPG. This mutant cell line also produces approximately three times more chondroitin sulfate as wild type cells (Esko et al., (1988) *Science* 241:1092; Lidholt et al., (1992) *Proc. Natl. Acad. Sci. USA* 89:2267).

Figure 4A:
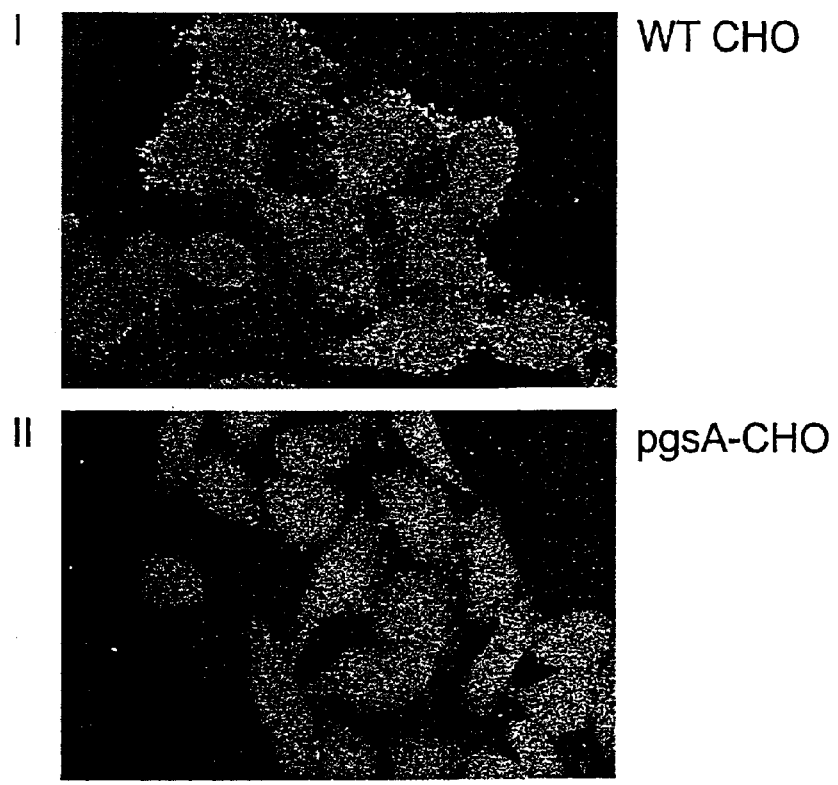
FIGS. 4A and 4B illustrate that heparan sulfate proteoglycan serves as a primary attachment receptor for AAV-2. Wild type CHO-K1cells and CHO-K1 mutants defective in proteoglycan synthesis were assessed for their ability to bind AAV-2. The cell line pgsA-745 lacks heparan sulfate and chondroitin sulfate proteoglycans. The cell line pgsD-677 lacks heparan sulfate proteoglycan and produces three fold excess chondroitin sulfate proteoglycans. The cell line pgsB-618 produces 15% of normal proteoglycans; while the cell line pgsE-606 produces an undersulfated form of heparan sulfate proteoglycan and normal levels of chondroitin sulfate proteoglycans.
Figure 4B:
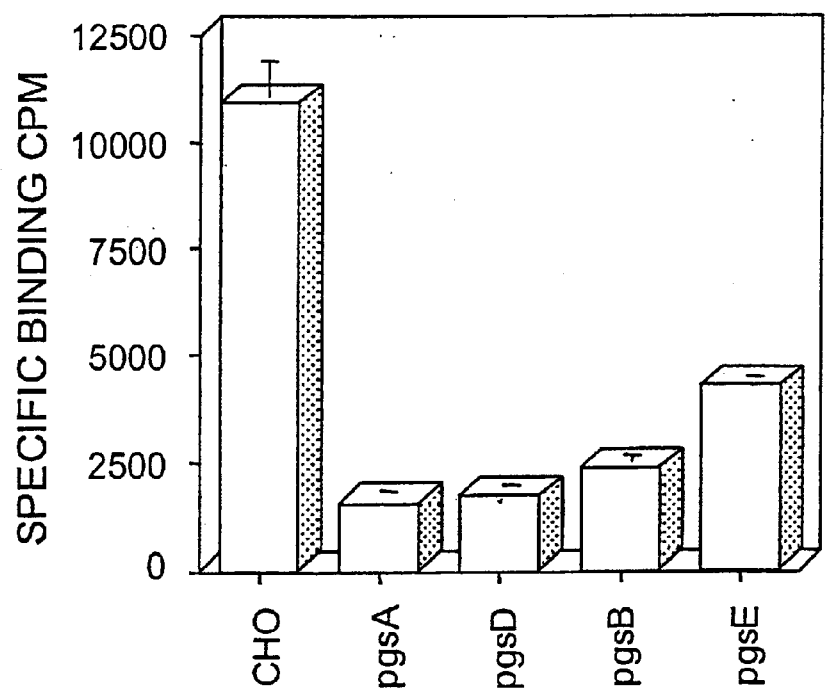

To assess AAV binding to wild type and mutant CHO cell lines, cells were incubated with Cy3 labeled virions or $^3$H-AAV-2 as described in Example 12. Bound $^3$H-virus was collected by centrifugation and fluorescent virus was visualized by confocal microscopy (FIGS. 4A and 4B). Although binding of Cy3-AAV to wt CHO cells was easily detectable (FIG. 4A, panel I), no significant virus binding to pgsA mutant CHO cells was observed (FIG. 4A, panel II). These binding observations were quantified using $^3$H-AAV-2. Compared with wild type CHO cells, there was a 7.0 and 6.4 fold reduction in AAV binding to cell lines pgsA-745 and pgsD-677, respectively. The poor attachment of AAV to the HS GAG minus mutant cells pgsA and pgsD (FIG. 4B) provides genetic data indicating that the presence of HSPG is a principle requirement for AAV attachment to the cell surface. Further, the inefficient binding to pgsD-677 demonstrates that AAV exhibits specificity for heparin. The 4.6-fold reduction in AAV binding to pgsB-618 was slightly higher than the binding to proteoglycan minus cells types pgsA and pgsD cells. This correlates well with the 85% overall lower production of GAGs by the pgsB-618 mutant cell line. AAV binding to the mutant pgsE-606 cell line that produces an undersulfated form of heparan sulfate, was also diminished, albeit to a lesser extent (2.6 fold). Since the pgsE-606 cell line is partially deficient in N-sulfotransferase, a reduction in AAV binding to this cell line suggests that N-sulfation of heparan sulfate may be an important determinant influencing AAV attachment. The observed differences in virus binding to wild type and GAG deficient cells was specific for AAV, since no effect was observed when binding of labeled adenovirus was used (data not shown).

Overall, these data indicate that the heparan and not chondroitin sulfate moieties of cell surface proteoglycans serve as attachment receptors for AAV. In addition, the diminished ability of AAV to bind pgsE-606 indicates that the degree of sulfation of heparan sulfate is an important factor influencing binding of AAV to heparan sulfate proteoglycan.

EXAMPLE 17

Heparan Sulfate Proteoglycan Mediates AAV Infection

Figure 5A:
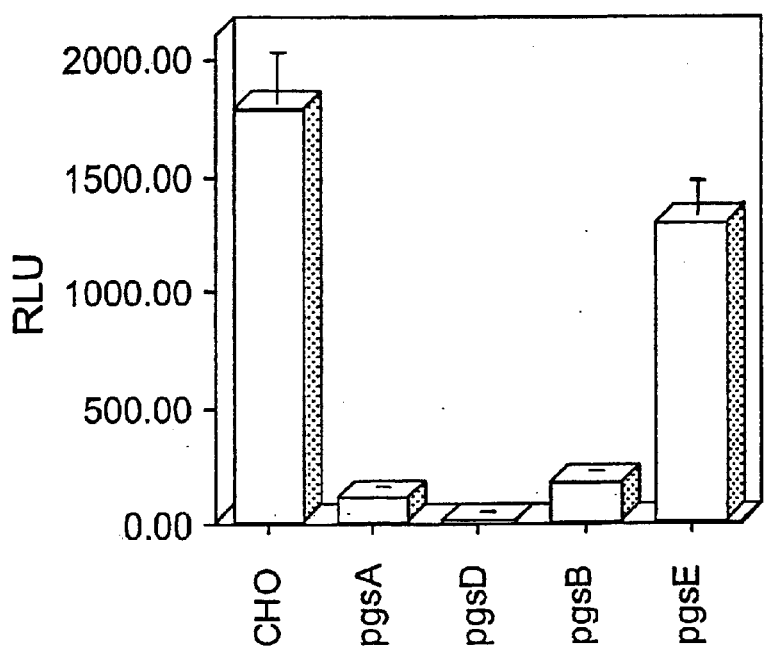
FIGS. 5A and 5B illustrate that heparan sulfate proteoglycan mediates AAV infection.

The CHO cell mutants defective in GAG synthesis were also used to provide genetic evidence that HSPG is necessary for an efficient AAV infection. As with the previous infection experiments, a rAAV-LacZ vector that expresses β-galactosidase was used to assess AAV-2 infectivity. The lack of cell surface HSPG significantly impaired the ability of AAV to infect CHO cells (FIG. 5A). Compared with AAV transduction of wild type cells, there was significant reduction in AAV transduction of pgsA and pgsD cells (FIG. 5A). In addition to lacking HSPG on the surface, the pgsD cells overproduce chondroitin sulfate proteoglycans. The poor infection of this cell line further demonstrates the specificity of AAV for cell surface heparan and not chondroitin moieties. We observed a 10-fold reduction in AAV transduction of pgsB cells which produce 85% less proteoglycan than wild type cells. With the exception of the pgsD cell line, the inefficient AAV transduction of the CHO cell mutants clearly paralleled the reduced ability of AAV to bind the cell surface. The above data indicate that infection by AAV is closely coupled to the amount of AAV that can attach to the cell surface and that this attachment is primarily mediated by HSPG. Finally, the pgsE cells that produce an undersulfated form of HSPG, supported AAV transduction but with 1.4-fold reduction (FIG. 5A), consistent with the previously observed level of AAV binding (FIG. 4B).

Figure 5B:
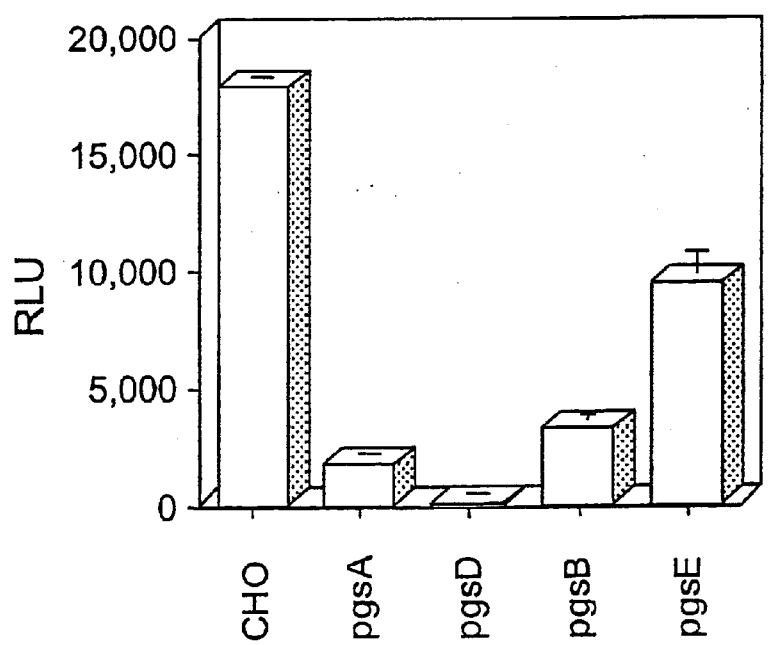

A rate limiting step in rAAV vector transduction is inefficient synthesis of second strand copies from virion ssDNA genomes (Ferrari et al., (1996) *J. Virol.* 7:3277; Fisher et al. (1996) *J. Virol.* 70:520; McCary et al, (1997) Adeno-associated viral vectors, p. 62–78, in Strauss and Barranger (eds.), Concepts in Gene Therapy). To ensure that the observed differences in AAV infection were a result of inefficient AAV binding and not due to impaired second strand synthesis, we treated cells with UV, a technique known to overcome inefficiencies at this step (Ferrari et al., (1996) *J. Virol.* 7:3277). When mutant cells were treated with UV to maximize transgene expression, enhancement of rAAV-LacZ transduction was observed (10-fold) but overall AAV infections were similar to non UV treated cells (FIG. 5B). Taken together, the results obtained with the CHO cell mutants deficient in GAG synthesis provide genetic evidence that HSPG mediates both attachment and entry of AAV-2.

EXAMPLE 18

Low Concentrations of Soluble Receptor-Like Molecules Enhance AAV Infection

Figure 6:
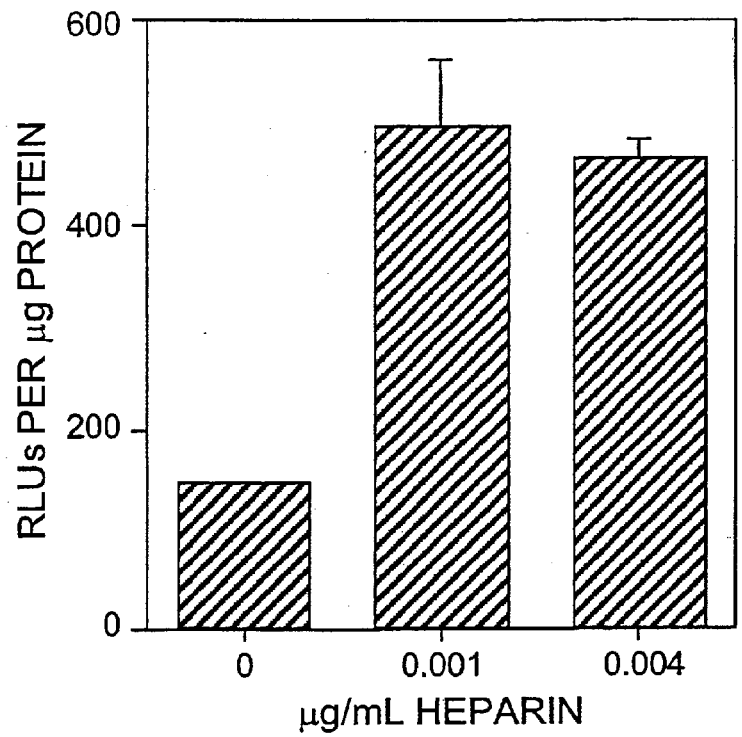
FIG. 6 illustrates that low concentrations of heparin enhance rAAV transduction of HeLa cells. HeLa cells were infected with rAAV-lacZ virus in the presence or absence of heparin, at the indicated concentrations, for one hour at 37° C. 48 hours after infection, cells were harvested and assayed for β-galactosidase activity, which is indicates as relative light units (RLU)/µg protein. Results are reported as the mean and standard deviation of one experiment performed in triplicate.

HeLa cells were infected with rAAV-lacZ virus in the presence or absence of heparin, at concentrations of 0 μg/mL, 0.001 μg/mL, and 0.004 μg/mL, for one hour at 37° C. Forty-eight hours after infection, cells were harvested and assayed for β-galactosidase activity, which is indicated as relative light units (RLU)/μg protein. The results of this experiment are shown in FIG. 6 as the mean and standard deviation of one experiment performed in triplicate. These data illustrate that low concentrations of heparin enhance rAAV transduction of HeLa cells.

EXAMPLE 19

Binding of Other AAV Serotypes to Cell-Surface Heparan Sulfate

Figure 7:
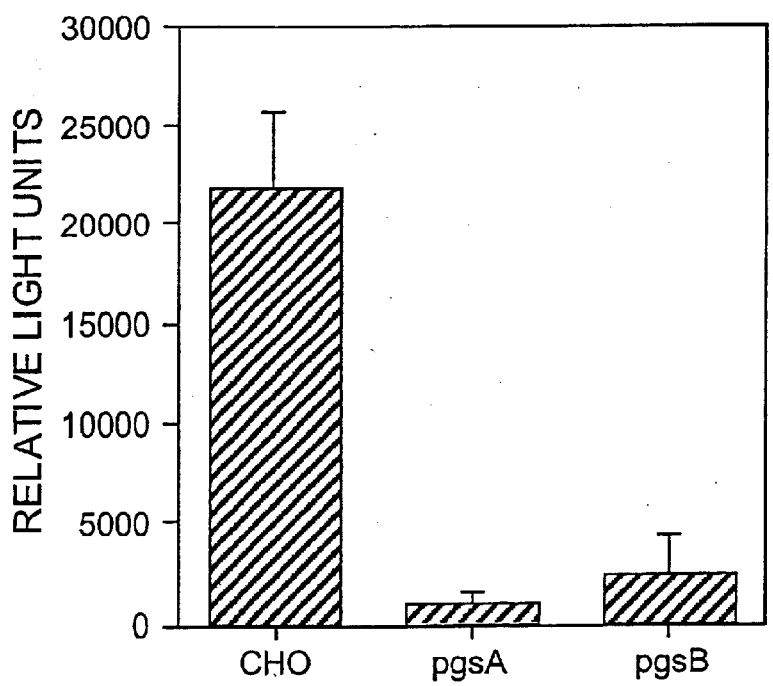
FIG. 7 demonstrates that HSPG is an important determinant of AAV type 3 infection. AAV3-LacZ virus was incubated with CHO cells and CHO cell mutants deficient in GAG synthesis at an MOI of 10 for 1 h at 37° C. Cells were harvested 44 h post infection and assayed for β-galactosidase activity. Data represent the mean and standard deviation of an experiment performed in triplicate.

Studies were performed to evaluate whether other AAV serotypes bind to HS. AAV3-LacZ virus was incubated with CHO cells and CHO cell mutants deficient in GAG synthesis (Example 2) at an MOI of 10 for 1 h at 37 ° C. Cells were harvested 44 h post-infection and assayed for β-galactosidase activity as described in Example 11. The results of these experiments suggest that AAV serotype 3 also requires HS for efficient infection (FIG. 7). Although a direct association of AAV-3 with HSPG remains to be determined, these observations raise the possibility that, as observed with AAV-2, AAV-3 may also interact with HSPG. The inability of AAV-2 to efficiently compete AAV-3 binding (Mizukami et al., (1996) *Virology* 217:124) may be reminiscent of HSV-1 and HSV-2 binding to specific sequences found in HS (Herold et al., (1996) *J. Virology* 70:3461). Preferential binding to distinct sequences found in HS may ultimately effect the efficiency by which AAV can infect cells. For example, the HS moieties displayed by syndecan proteoglycan are known to differ in their fine structure on different cell types

EXAMPLE 20

Screening of Targets for Susceptibility of AAV Infection

Figure 8:
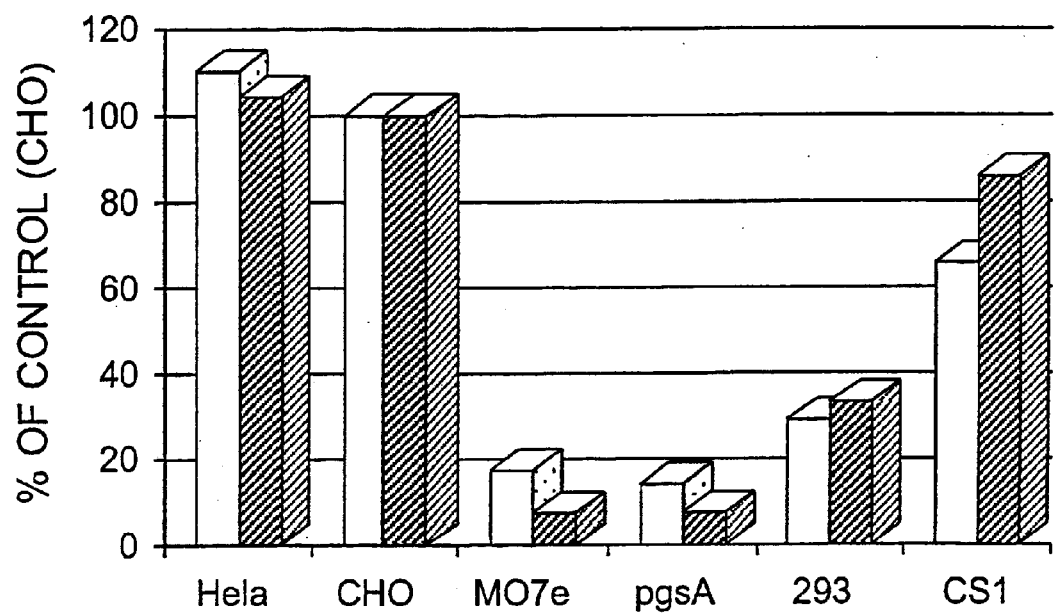
FIG. 8 demonstrates the correlation between relative HS expression levels and AAV-2 binding. Relative percent of cell surface heparan sulfate (HS) (left-hand bar) compared to AAV-2 binding (right-hand bar) to a panel of in vitro cell lines (CHO cells=100%). Cell surface heparan sulfate was determined by FACS analysis using anti-heparan sulfate HepSS-1 monoclonal antibody. Relative HS expression was determined by taking the fold difference between the median fluorescence obtained with a control antibody and HepSS-1. Binding studies were performed with $^3$H-labeled AAV-2 virions at 4° C.

Identification of HS as a receptor for AAV will aid in the identification of cell types that are capable of supporting rAAV transduction. The amount of heparan sulfate detected by fluorescent flow cytometric analysis (FACS) correlates with the ability of virus to bind various cell lines in vitro (FIG. 8).

Figure 9B:
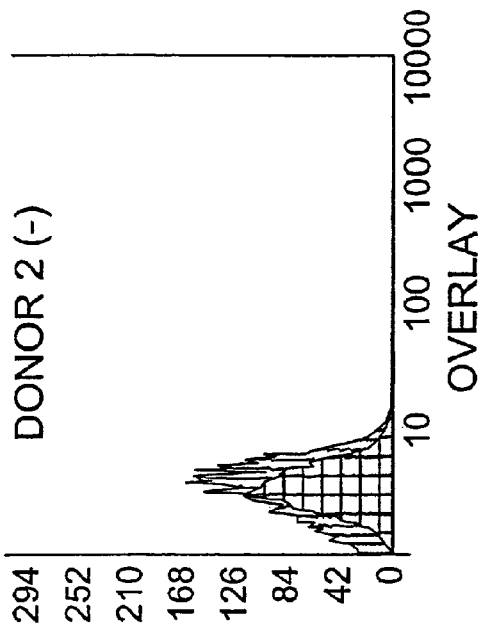
FIGS. 9A and 9B illustrate that screening of cell samples for the presence of the AAV receptor is predictive of the ability of cells to bind AAV.
Figure 9A:
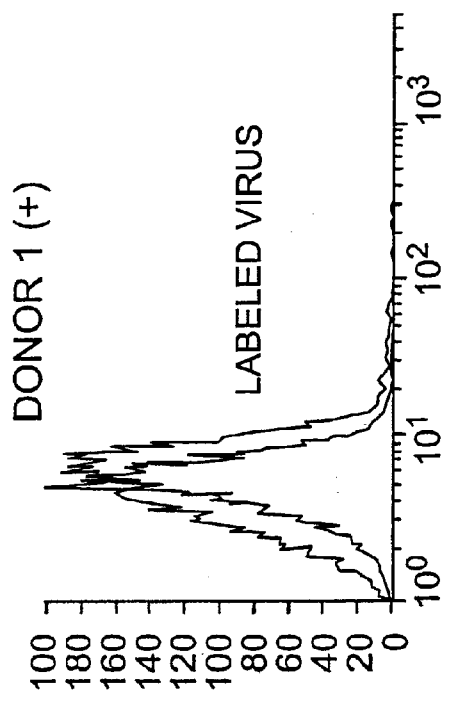

CD34+ bone marrow progenitor cells were screened for AAV binding and the presence of cell surface heparan sulfate. Of the four human donors of bone marrow cells tested, three donors had CD34+ cells that lack cell surface expression of heparan sulfate and were found to be incapable of binding AAV, while one donor had CD34+ cells that were positive for cell surface expression of heparan sulfate, and also were capable of binding AAV. This result was determined as follows: Cy3-labeled AAV or anti-heparan sulfate antibody (FITC) were incubated with cells for one hour at 4° C. Cells were washed three times and fixed in a 1% paraformaldehyde solution prior to FACS scan. The results are overlaid onto control samples with unlabelled virus or non-specific FITC-conjugated antibody. FIG. 9A illustrates human bone marrow CD34+ cells positive for both AAV virus binding (top graph) and heparan sulfate (bottom graph).

As is seen in FIG. 9A, cells that are positive for the AAV receptor cell surface heparan sulfate exhibit a shift in relative fluorescent value to the right (bottom graph), as compared to non-specific PITC conjugated antibody. Similarly, virus bound to the cell surface exhibit a spectroscopic shift to the right when compared to unlabelled virus. FIG. 9B illustrates a FACS analysis screen for cells that are negative for both cell surface heparan sulfate (ie., antibody specific for heparan sulfate does not bind to the cell) and for AAV virus binding. When the control data are overlaid onto the experimental data, no fluorescent shift is observed. FIGS. 9A and 9B illustrate that screening of cell samples for the presence of the AAV receptor is predictive of the ability of cells to bind AAV. These results also indicate that the primary block in rAAV transduction of CD34$^+$ cells is the initial binding of virus to the cell surface.

EXAMPLE 21

Purification of AAV Using Heparin/Heparin Sulfate

Recombinant AAV is prepared by transfection of HeLa or 293 cells using an adenovirus helper. A cell lysate is produced by successive freeze/thaw cycles, and cellular debris is removed by low-speed centrifugation. Viral and cellular proteins are concentrated by ammonium sulfate precipitation. Following an initial bulk purification (e.g., ammonium sulfate precipitation, size-exclusion chromatography, or density gradient fractionation), rAAV is affinity-purified by both conventional chromatography and HPLC using several commercially available heparin matrices (e.g., Heparin-Agarose Type I; Sigma). Binding is carried out as described by the manufacturer, typically under low salt conditions (e.g., 0.3 M). Bound AAV is eluted by a high salt wash (e.g., 1 M NaCl).

Figure 10:
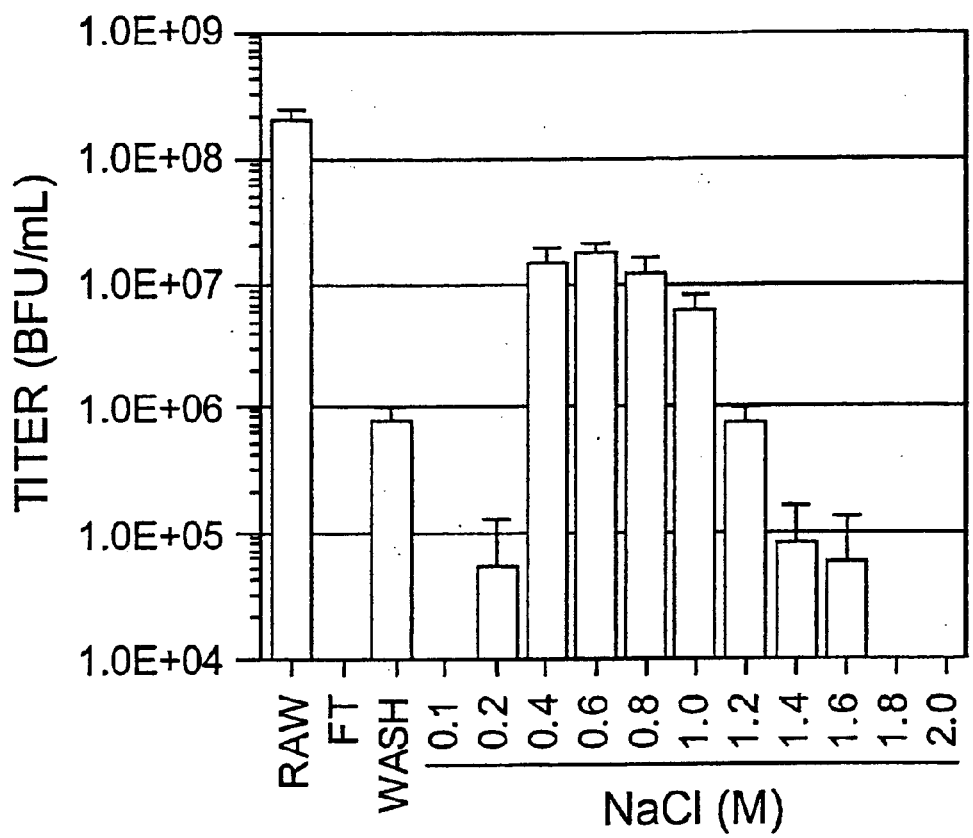
FIG. 10 illustrates the elution profile of AAV purified using affinity chromatography with heparin bound to a solid support. Results are shown as virus titer expressed in BFU/ml.

AAV has been purified as described above using a heparin sepharose column. The viral and cellular proteins in the cell lysate were concentrated using an ammonium sulfate precipitation. The resulting precipitate was resuspended and infectious rAAV particles were separated from cellular proteins by gel filtration chromatography using Sephacryl S-300 HR (Pharmacia). rAAV from positive fractions (as determined by ELISA) were concentrated and further purified by affinity chromatography using a heparin column and a linear salt gradient (Pharmacia) as illustrated in FIG. 10.

Purification of AAV using iodixanol density separation followed by heparin affinity purification is described by Zolotukhin et al. (*Gene Therapy*, in press). This method was employed to effectively purify AAV to over 99% purity from a crude cell lysate. Moreover, the majority of contaminating helper adenovirus was found in the flow-through fraction, and the concentration of adenovirus in the crude cell lysate was reduced by five orders of magnitude in the affinity-purified AAV fractions. Furthermore, particle-to-infectivity ratios of purified rAAV by heparin affinity purification are superior to those obtained by conventional purification methods employing ammonium sulfate fractionation followed by cesium chloride purification (particle-to-infectivity ratios of 26–73 vs. 241–1600).

Accordingly, strategies for purifying AAV based on its affinity for heparin/HS are fast, simple and reproducible as compared with conventional purification methods.

EXAMPLE 22

Plasma Membrane Purification

Plasma membranes were prepared from HeLa S3 cells by a sucrose gradient flotation method as described previously (Hennache and Boulanger, (1977) *Biochem. J.* 166:237). $1 \times 10^9$ HeLa S3 cells were harvested, washed in PBS, and resuspended in 7 ml ice cold lysis buffer (10 mM Tris-HCl pH 7.4, 10 mM NaCl, 1.5 mM MgCl$_2$, plus protease inhibitors: 10 µg/ml leupeptin, 1 mM PMSF, and 1 mM iodoacetamide). After a 10 minute incubation on ice, cells were lysed at 0–4° C. in a dounce homogenizer with a tight fitting pestle using 20–30 strokes. Complete lysis was monitored by light microscopy. A 50 µl aliquot was removed and placed at −80° C. for protein quantitation and later assessment of 5' nucleotidase activity. Next, 1 ml of 80% weight/volume sucrose was then added to give a final concentration of 10% sucrose. All sucrose solutions were made weight/volume in 10 mM Tris HCl pH 7.4, 5 mM MgCl$_2$ and filter sterilized. The lysate was then layered onto two preformed 50%/30% sucrose gradients (4 ml in lysate/tube) consisting of 5 ml 50% sucrose and 7.5 ml 30% sucrose. After centrifugation at 1,500 g for 15 minutes at 4° C., the 30%/50% interface was collected with a pasteur pipette and placed on ice. Membranes were then diluted with three volumes of ice cold buffer (10 mM Tris-HCL pH 7.4, 5 mM MgCl$_2$) and pelleted at 5,800 g for 20 minutes. Next, the pellet was resuspended in 18 ml of 65% sucrose, homogenized in a dounce with a loose fitting pestle, and 9 ml was placed on the bottom of a preformed 55%/45%/40% sucrose gradient (9 ml of each sucrose solution in SW28 tubes; $1 \times 3_{1/2}$ inch tubes (Beckman, item #344058)). Tubes were spun in a SW28 rotor for 2 hours at 24,000 rpm. The visible band at the 45/55 interface was enriched in plasma membranes as assessed by 5'-nucleotidase activity and was removed with a syringe and 18 gauge needle. Membranes were then diluted with 2–3 volumes of ice cold buffer and spun at 6,500 rpm for 35 minutes in a SW28 rotor to pellet. Membrane pellets were immediately placed at −80° C. for later use. To prepare membranes for electrophoresis, membrane pellets were resuspended in ice cold PBS containing 0.5% NP40 detergent. Protein concentration was determined using BCA Pierce reagent and BSA standards prepared in PBS/NP40. Purification was assessed by monitoring 5'-nucleotidase activity in the crude lysate compared to the purified fraction. Typically, 30-fold enrichment of activity is observed.

EXAMPLE 23

5'-Nucleotidase Assay

5'-Nucleotidase activity was monitored as described (Widnell and Unkeless, (1968) *Biochemistry* 61:1050). Assays were performed under reaction conditions of 100 mM Tris-HCl pH 8.5, 10 mM AMP, and 10 mM MgCl$_2$ in a total volume of 300 µl. Typically a 2× master reaction mix of Tris-HCl, AMP and MgCl$_2$ was prepared and aliquoted into Eppendorf tubes. H$_2$O was then added to the Eppendorf tubes in order that a range (1–10 µl) of crude lysate or membrane could be assayed in a 300 µl total volume. Membrane/lysate was added to tubes in a timed fashion and placed at 37° C. for 20 minutes. Each reaction was stopped at 20 minutes by addition of 700 µl of 1 part 10% ascorbic acid (made fresh) and 6 parts 0.42% ammonium molybate in 1N H$_2$SO$_4$ (0.5 M). Tubes were then incubated at 45° C. for 20 minutes and absorbance at 820 nm was determined using a spectrophotometer. Control reactions without AMP and without membrane were performed. The reaction without AMP served as the blank for the spectrophotometric reading. Results are reported in units (OD$_{820\ nm}$) per mg protein per minute.

EXAMPLE 24

Preparation of the 5–20% SDS PAGE Gradient Gel

Gradient gels were prepared using standard SDS PAGE separation and staking gel buffers (Sambrook et al., (1989)

Molecular Cloning, A Laboratory Manual, (N. Ford et al., eds.), Cold Spring Harbor Laboratory Press, New York). For one large gradient gel, using 16 cm plates and 1.5 mm spacers, two acrylamide solutions were prepared (1) 15 ml of a 5% bis-acrylamide solution (add 24 $\mu$l 1% APS) and (2) 30 ml of a 20% bis-acrylamide containing 4.5 grams of sucrose (add 21 $\mu$l of 1% APS). An ECONO TM pump (Bio-Rad) was set up in order that the 20% acrylamide solution could be pumped into the stirred 5% acrylamide solution. The peristaltic pump tubing that was set up to pump the mixed acrylamide solution was inserted between the protein gel plates to the bottom of the gel in order that acrylamide could be filled from bottom of the gel. Prior to pumping acrylamide, a layer of $H_2O$ is pumped into the bottom of the gel. After clearing all $H_2O$ from the pump tubing, 5 $\mu$l of TEMED was added to each solution and solutions were quickly placed in respective beakers. Pumping was performed at flow rate of 6.4 ml/minute. After polymerization, a standard SDS PAGE 4% bis-acrylamide stack was prepared.

EXAMPLE 25

Viral Overlay Assay and Western

Plasma membranes were prepared from HeLa S3 cells by a sucrose gradient flotation method as described previously (Hennache and Boulanger, (1977) *Biochem. J.* 166:237). Plasma membrane enrichment was assessed by following the activity of 5'-nucleotidase (Widnell and Unkeless, (1968) *Biochemistry* 61:1050). For the viral overlay analysis: 50–100 $\mu$g/lane of plasma membrane proteins were separated under reducing conditions on a 5–20% SDS-PAGE gradient gel then electrophoretically blotted to nitrocellulose by semi-dry transfer (Bio-Rad). Non-specific binding was blocked by incubation of the membrane overnight at 4° C. in phosphate-buffered saline/0.05% tween-20 (PBST) containing 10% non-fat dried milk (w/v). After blocking, the proteins were probed for 3 h at room temperature with $6 \times 10^{11}$ AAV particles per ml in PBST. A brief rinse was followed by two 10 minute washes with PBST to remove unbound virus. The blot was then incubated with a 1:300 dilution of mAb A20 hybridoma supernatant for 1 h. After washing three times for 5 minutes in PBST, the blot was incubated for 1 h with a 1:10,000 dilution of secondary goat/anti-mouse-HRP. The incubation was followed by one brief wash, one 15 minute wash, and three 5 minute washes in PBST. One final 5 minute wash using PBS without tween-20 was done before chemiluminescence analysis with a 1:1 mix of 2×luminol/enhancer and 2× stable peroxide solutions (Pierce). The control was processed as described above except virus was not used. The western blot analysis was performed with a 1:100 dilution of B5-1VF2 and a 1:10,000 dilution of secondary antibody as described by standard enhanced chemiluminescence (ECL) methods (Amersham) using the chemiluminescence reagent described above.

EXAMPLE 26

Immunoprecipitation

For each immunoprecipitation reaction, 1 ×10⁷ HeLa cells (one 10 cm plate 80–90% confluent) were extracted in 600 $\mu$l of RIPA lysis buffer (1% Triton X-100, 1% Na-deoxycholate, 0.1% SDS, 158 mM NaCl, 50 mM Tris-HCl pH 7.5 with protease inhibitors: 1 mM PMSF, 1 mM iodoacetamide, 25 $\mu$g/ml leupeptin, 10 $\mu$g/ml aprotinin and 1 mM EGTA). Cells were first washed in PBS. Plates were then placed on ice and 600 $\mu$l of ice cold lysis buffer was added to each plate. Lysis was allowed to occur on ice for 20–25 minutes before scraping the cells from the plates and pooling the lysate into a 15 ml conical tube. The lysate was then clarified by centrifugation at 3000 rpm in a microcentrifuge for 10 minutes at 4° C. and the supernatant was transferred to a fresh 15 ml tube. The lysate was pre-cleared with a non-specific antibody by incubation (rotating) with 5 $\mu$g of isotype matched mouse IgG1 antibody/500 $\mu$l lysate for 1 h at 4° C. To capture the pre-clearing antibody, 45 $\mu$l of protein A/G beads/500 $\mu$l lysate was subsequently added. After rotating with the beads for 1 hour at 4° C., the tube was centrifuged at 1,500 rpm in a Sorvall RT 6000B swinging bucket rotor for 5 minutes. The pre-cleared supernatant was then aliquoted to Eppendorf tubes on ice, 500 $\mu$l/tube. To immunoprecipitate $\beta_5$ integrin, 5 $\mu$g of B5-IA9 mAb was added per 500 $\mu$l lysate. Control immunoprecipitations were also performed with mouse IgG1 antibody (5 $\mu$g/500 $\mu$l lysate). Further, antibody was excluded from one tube (later to serve as the control for the secondary rabbit anti-mouse IgG antibody). All tubes, the $\beta_5$ immunoprecipitation reaction and controls, were rotated at 4° C. overnight. Next, 1 $\mu$l (2.5 $\mu$g) of rabbit anti-mouse IgG antibody (Jackson ImnmunoResearch) was added to each immunoprecipitation reaction to maximize adsorption of immunocomplexes to protein A/G sepharose beads (Santa Cruz Biotech.) (Pasqualini et al., (1993) *J. Cell Sci.* 105:101) and reactions were incubated for 1 hour at 4° C. Protein A/G beads, 45 $\mu$l per reaction, were then added to each reaction and tubes were placed at 4° C. rotating. Beads were then pelleted by centrifugation at 3000 rpm for 2 minutes at 4° C. The protein A/G beads were subsequently washed 4 times in ice cold immunoprecipitation buffer. Beads from each reaction were then resuspended in 35 $\mu$l SDS PAGE sample buffer (Sambrook et al., (1989) Molecular Cloning, A Laboratory Manual, (N. Ford et al., eds.), Cold Spring Harbor Laboratory Press, New York) and immediately boiled for 3 minutes. The immunoprecipitate was separated on a standard 7.5% SDS polyacrylamide gel under reducing conditions and then blotted to nitrocellulose for viral overlay analysis as described in Example 25.

EXAMPLE 27

Flow Cytometric Analysis

To prepare for fluorescence activated cell sorting (FACS) analysis, adherent cells were first detached with 10 mM EDTA followed by two washes in phosphate buffered saline (PBS) containing 8.8 mM $CaCl_2$ and 0.5 mM $MgCl_2$. All cells were washed in HEPES-buffered saline (HBS) (Sambrook et al., (1989) Molecular Cloning, A Laboratory Manual, (N. Ford et al., eds.), Cold Spring Harbor Laboratory Press, New York) and resuspended in HBS containing 1% BSA as to result in a concentration of $2 \times 10^6$ cells/ml. Next, 500 $\mu$l ($1 \times 10^6$ cells) of each cell type suspension to be analyzed was aliquoted into two Eppendorf tubes and placed on ice (one tube is for control Ab and the other for anti-$\alpha_v\beta_5$ integrin mAb). Either 3 $\mu$g of mAb PIF6 (anti-$\alpha_v\beta_5$ integrin antibody) or 3 $\mu$g mouse IgG1 antibody (control) were added to appropriate tubes and incubated with cells for 1 h rotating at 4° C. Cells were then washed twice with 1 ml ice cold HBS and resuspended in 500 $\mu$l HBS containing 1% BSA. Next, 1 $\mu$g of secondary goat anti-mouse antibody conjugated to fluorescein isothiocyanate was added to each tube and cells were incubated in the dark for 1 h at 4° C. rotating. Cells were then washed three times with ice cold PBS resuspended in one-half volume PBS+one-half volume 2% paraformaldehyde (final concentration 1%). Sample was stored at 4° C. until analysis.

EXAMPLE 28

Infectivity and Virus Binding Assays

All infectivity and binding assays were done in suspension in a buffer determined to result in maximum cell viability, HEPES-buffered saline (HBS) containing 1% BSA (HBSB) (Sambrook et al., (1989) Molecular Cloning, A Laboratory Manual, (N. Ford et al., eds.), Cold Spring Harbor Laboratory Press, New York). Adherent cells were first detached with 10 mM EDTA followed by two washes in phosphate buffered saline (PBS) containing 8.8 mM $CaCl_2$ and 0.5 mM $MgCl_2$ and one wash in HBS. To assess the effect of EDTA on AAV transduction, HeLa cells were incubated with recombinant virus at an MOI of 2 in HBS±20 mM EDTA for 1 hour at 4° C. After washing in HBS±EDTA to remove unbound virus, cells were resuspended in HBS±5 mM EDTA and placed at 37° C. for 30 minutes. Cells were then trypsinized (0.5 mg/ml) for 10 minutes to remove uninternalized virus (Mizukami et al., (1996) Virology 217:124), washed, and resuspended in media before transfer to 6-well tissue culture dishes. Cells were fixed and stained for β-galactosidase activity 24 h (rAd-LacZ)-36 h (rAAV-LacZ) after infection. For transduction experiments of CS1 cell lines, recombinant virus was bound to $5 \times 10^5$ cells at 4° C. in HBSB. After 1 h, unbound virus was removed, cells were washed, resuspended in HBSB and placed at 37° C. for 40 minutes. Cells were then plated in media containing 2% heat-inactivated fetal bovine serum (Gibco/BRL). After 24 h (rAd infection)-48 h (rAAV infection) cells were harvested and assayed for β-galactosidase activity with a Galacto-Light Plus kit (Tropix Inc., Bedford, Mass.) as described by the manufacturer. Data were collected in a luminometer within the linear range of the assay and enzyme activity is expressed as relative light units (RLU) per $1 \times 10^5$ cells. Each experimental condition was performed in triplicate and independent experiments yielded similar results.

Binding assays were performed in suspension. $^3$H-labeled wt AAV ($4 \times 10^{11}$ particles) was incubated with $3 \times 10^5$ cells in HBSB either in the absence or presence of 50 fold excess unlabeled wt AAV. After rotation at 4° C. for 90 minutes, cells were washed three times with ice cold HBSB, solubilized in 0.3 N NaOH, then neutralized with glacial acetic acid, and counted in a scintillation counter.

EXAMPLE 29

Internalization Assay

To monitor virus internalization, Cy3-labeled AAV-2 was incubated with $5 \times 10^5$ cells at a concentration of $3 \times 10^5$ particles/cell for 1 h at 4° C. in HBSB. After thorough washing with ice cold HBSB, cells were resuspended in HBSB and placed in a 37° C. water bath. At the indicated times, cells were placed on ice, washed once with ice cold HBSB, and resuspended in 2% paraformaldehyde in PBS. Cells were then distributed to coverslips previously treated with Cell-Taq Adhesive as described by the manufacturer (Collaborative Biomedical Prod.; item #40240).

EXAMPLE 30

Figure 11A:
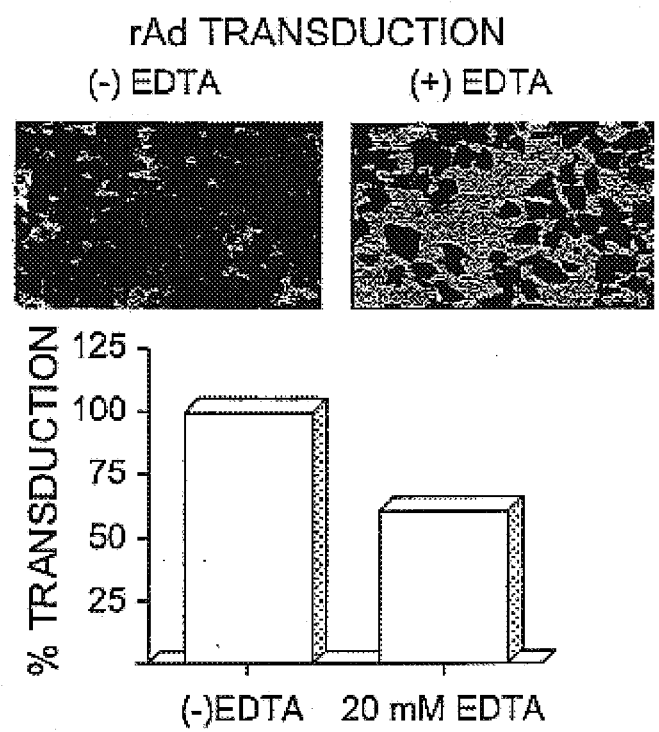
FIGS. 11A and 11B illustrate the effect of EDTA on Ad and AAV infection. HeLa cells were infected with recombinant virus (rAd-LacZ [FIG. 11A], rAAV-LacZ [FIG. 11B]) at an MOI of 2 either in the presence or absence of divalent cation chelator EDTA (20 mM) as described in methods. 24 h post Ad infection, and 36 h post AAV infection, cells were fixed and stained for β-galactosidase activity (upper panel). Transduction has been quantitated in the lower panel as the percentage of HeLa cells transduced in the presence or absence of EDTA.
Figure 11B:
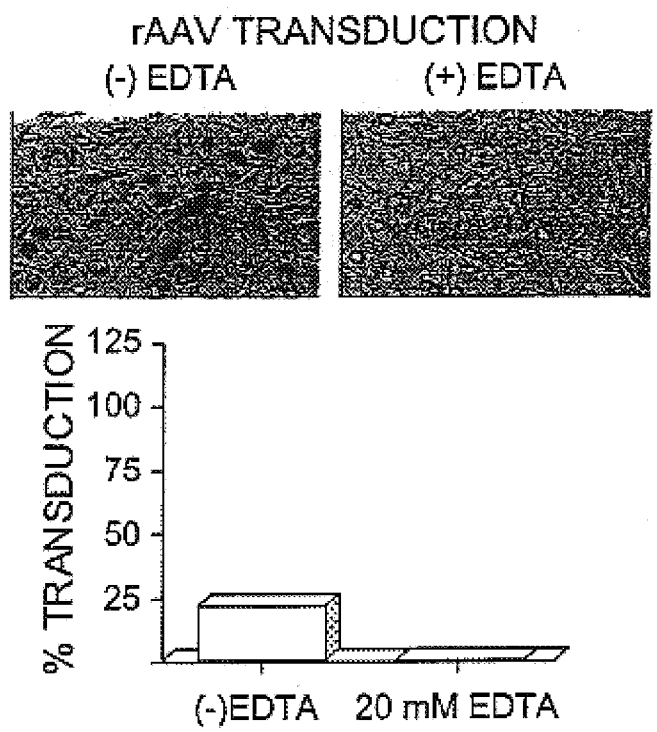

Effect of EDTA on AAV infection $α_v$ integrins require divalent cations for their proper folding and function (Tuckwell et al., (1993) Symp. Soc. Exp. Biol. 47:107). Previous studies have established that chelation of divalent cations with EDTA inhibits adenovirus infection (Svensson and Persson, (1984) J. Virol. 51:687) and that this inhibition, in part, is due to the disruption of av integrins (Wicham et al., (1993) Cell 73:309). Therefore, as a first assessment of whether or not AAV might use a similar uptake mechanism as adenovirus, we assayed AAV-2 infections on HeLa cells in the presence or absence of EDTA (FIGS. 11A and 11B). We observed a 40% inhibition of recombinant Ad-LacZ transduction (FIG. 11A) and greater than 90% inhibition of AAV infection (FIG. 11B) in the presence of 20 mM EDTA. While EDTA proved to be a potent inhibitor (>90%) of AAV infection, the level of inhibition observed with Ad was in agreement with previous published results (20–50% inhibition) (Svensson and Persson, (1984) J. Virol. 51:687). Interestingly, EDTA proves to be a potent inhibitor (>90%) of AAV infection (FIG. 11B). Although EDTA can have a multitude of effects on cells, these findings were consistent with a possible role for integrin in AAV-2 infection and warranted further investigation.

EXAMPLE 31

Cellular Proteins Identified by AAV Viral Overlay

Figure 12A:
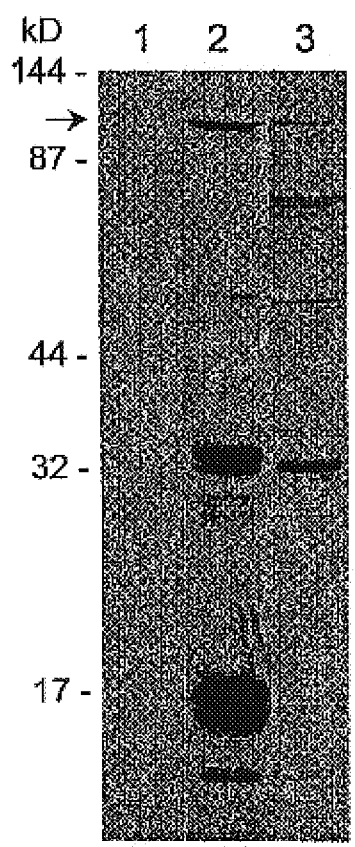
FIG. 12 illustrates viral overlay and western blot analysis of plasma membrane proteins. Panel A: Purified HeLa cell plasma membrane proteins were separated by 5–20% gradient SDS-PAGE under reducing conditions. After blotting to nitrocellulose, proteins were probed with either no virus (lane 1), purified AAV-2 virions (lane 2), or B5-IVF2 mAb for detection of the $\beta_5$ subunit of $\alpha_v\beta_5$ integrin (lane 3). Blots were then incubated with A20 mAb, which interacts with AAV-2 virions (lanes 1 & 2) and secondary goat anti-mouse IgG conjugated to HRP (lanes 1, 2, & 3) for detection by chemiluminescence and autoradiography. Panel B: Viral overlay analysis of two different membrane preparations. Lanes 1 & 2 represent an AAV-2 overlay. Arrows point to the 150 kDa (lane 1) and 100 kDa (lane 2) proteins that interact with AAV. The corresponding control overlays performed without virus are shown in lanes 3 & 4.
Figure 12B:
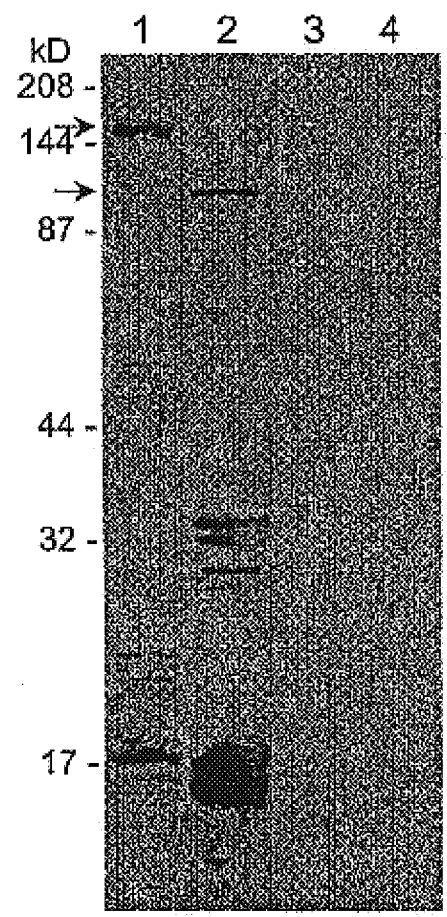

Integrins are often involved in mediating cell-cell and cell-matrix interactions and represent a family of transmembrane heterodimeric proteins comprised of distinct a and β subunits (Tuckwell et al., (1993) Symp. Soc. Exp. Biol. 47:107). We tested gradient purified AAV-2 for the ability to bind to purified plasma membrane proteins after fractionation on 5–20% gradient gels using a triple western technique (see Examples 24–25 for details). Using this assay, AAV-2 bound a series of proteins at 100, 55, 35, 33, 17, 15 and 11 kDa (FIG. 12, Panel A, lane 2). The interaction of AAV-2 with the 100 kDa protein was of specific interest since the $β_5$ subunit of $α_vβ_5$ integrin migrates with this apparent molecular weight under similar conditions (Ramaswamy and Hemler, (1990) EMBO J. 9:1561). Accordingly, western analysis of purified plasma membrane proteins performed with a mAb that recognizes the reduced form of the $β_5$ subunit (Pasqualini et al., (1993) J. Cell. Sci 105:101) detected a protein species at the same position as a species detected by the virus overlay (FIG. 12, Panel A, lane 3). To confirm that the $β_5$-specific mAb and AAV were each recognizing a protein that migrates at the same molecular weight, the viral overlay was stripped and reprobed with anti-$β_5$ mAb. The results from this analysis confirmed that the $β_5$ mAb and AAV recognized a protein of the same apparent MW (data not shown), suggesting that AAV may directly interact with the $β_5$ subunit of the $α_vβ_5$ integrin.

The absence of bands in the no virus control (FIG. 12, Panel A, lane 1) demonstrates that all proteins detected by this technique are the result of AAV binding and not due to non-specific binding of either the anti-AAV-2 Ab or the HRP conjugated secondary Ab.

It should be noted that AAV-2 has previously been shown to interact with a 150 kDa membrane protein by viral overlay analysis (Mizukami et al., (1996) Virology 217:124). When membranes are prepared in the manner described in this published work, we see similar results (FIG. 12, Panel B, lane 1). However, this membrane preparation purifies membranes on a 80%/60%/10% sucrose gradient according to a method described for the isolation of total membranes (Chong and Rose, (1993) J. Virol. 67:407) and thus most likely contains a high percent of contaminating non-plasma membrane proteins. The membranes used in this study (FIG. 12, Panel B, lane 2) were purified by a method for the isolation of plasma membrane proteins described by Hennache & Boulanger, (1977) Biochem. J. 166:237. This method fractionates membranes on a 65%/55%/45%/40% sucrose gradient and should yield a membrane preparation with less contamination of non-plasma membrane proteins.

The interaction of virus with the 150 kDa membrane protein observed by us and others may represent a virus interaction with a non-plasma membrane protein. Alternatively, it could be a cell surface protein that migrates in a different fraction in the later preparation. Whatever the cause for the observed differences, we are confident the protein preparations used in this study are highly enriched for plasma membrane proteins. This enrichment was estimated to be 30-fold as assessed by 5'-nucleotidase activity (Table 1).

TABLE 1

Enrichment for Plasma Membrane Proteins of HeLa Cells

| | Amount assayed | $OD_{820}$ | Protein Concentration | Specific Activity of 5'-nucleotidase $OD_{820}$ units/mg/20 min |
|---|---|---|---|---|
| Homogenate | 5 µl | 2.543 | 34 mg/ml | 14.7 units/mg/20 min |
| Plasma membrane fraction | 5 µl | 2.236 | 1.0 mg/ml | 440 units/mg/20 min |

EXAMPLE 32

Figure 13A:
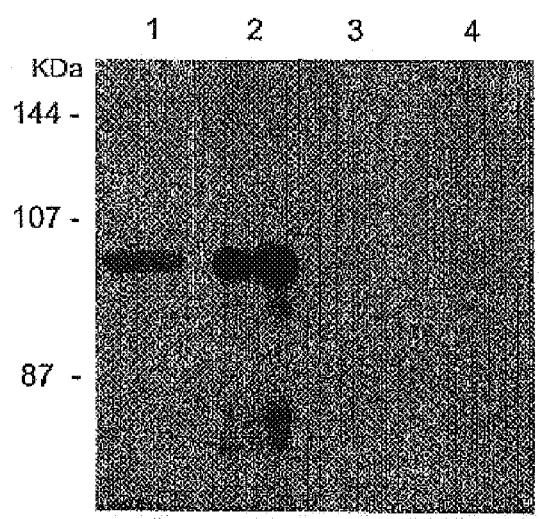
FIG. 13 illustrates a virus overlay of immunoprecipitated $\beta_5$ subunit of $\alpha_v\beta_5$ integrin (Panels A and B). Purified plasma membrane proteins (lanes 1, Panels A and B), immunoprecipitated $\beta_5$ subunit of $\alpha_v\beta_5$ integrin (lanes 2, Panels A and B), and control immunoprecipitations [isotype matched IgG1 Ab (Panels A and B, lanes 4), or rabbit anti-mouse Ab (Panels A and B, lanes 3)] were separated by 7.5% SDS-PAGE under reducing conditions. Proteins were blotted to nitrocellulose and probed with (Panel A) or without (Panel B) purified AAV-2 virions as described in FIG. 12.
Figure 13B:
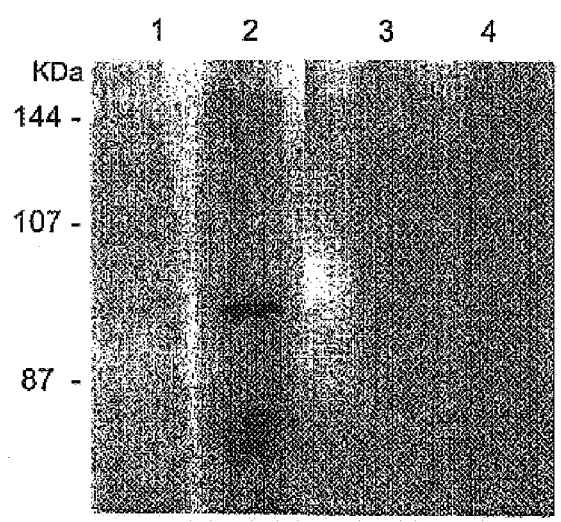

AAV-2 Directly Associates with the $\beta_5$ Subunit of $\alpha_v\beta_5$ Integrin To confirm that the 100 kDa species (FIG. 12, Panel A) identified in purified plasma membranes was the $\beta_5$ subunit of $\alpha_v\beta_5$ integrin, 5 was immunoprecipitated from HeLa cells, the immunoprecipitated material was transferred to nitrocellulose, and a viral overlay analysis was performed. The results are shown in FIG. 13 in Panel A (virus overlay) and Panel B (control overlay without virus). AAV-2 exhibited a direct association with the immunoprecipitated $\beta_5$ integrin subunit (FIG. 13, Panel A, lane 2). As expected, the signal generated with immunoprecipitated $\beta_5$ integrin was greater than that obtained from the total plasma membrane proteins (FIG. 13, Panel A, compare lane 1 with lane 2). In the absence of virus, the 100 kDa protein was not detected in either HeLa membranes (FIG. 13, Panel B, lane 1) or immunoprecipitated $\beta_5$ subunit extract (FIG. 13, Panel B, lane 2). Therefore, the detection of the 100 kDa species was virus specific. Furthermore, controls demonstrated that immunoprecipitation of the 100 kDa species was specific to anti-$\beta_5$ mAb, since no signal was detected when immunoprecipitations were performed with either a control IgG1 isotype match antibody (FIG. 13, Panel A, lane 4 and FIG. 13, Panel B, lane 4) or with the secondary antibody that was used to maximize adsorption of the protein/Ab complexes to protein A sepharose (FIG. 13, Panel A, lane 3 and FIG. 13, Panel B, lane 3).

EXAMPLE 33

$\alpha_v\beta_5$ Integrin Promotes AAV-2 Infection

Figure 14A:
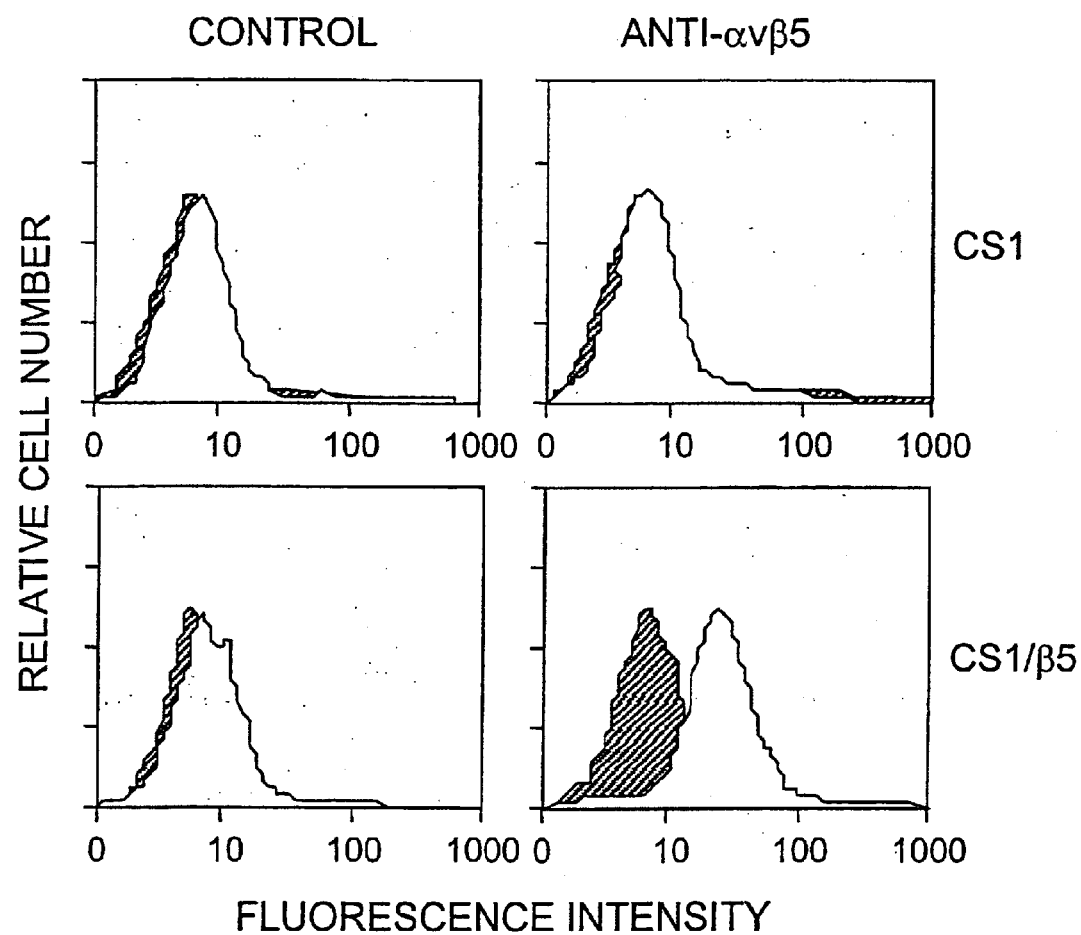
FIGS. 14A, 14B, and 14C illustrate $\alpha_v\beta_5$ expression and vector transduction of CS-1 and CS1/β5 cells. The data in FIG. 14A demonstrates FACS analysis of $\alpha_v\beta_5$ expression on CS-1 and CS1/β5 cell lines. $\alpha_v\beta_5$ integrin was identified with PIF6 mAb using mouse IgG$_1$ (MOPC 21) as control isotype matched Ab. Transduction of CS-1 and CS1/β5 cell lines with rAAV (FIG. 14B), or rAd (FIG. 14C). Gene transduction was determined by a chemiluminescence assay 24 h (rAd) or 48 h (rAAV) post infection. Data represent the mean and standard deviation of experiments performed in triplicate (FIGS. 14B and 14C). Separate experiments yielded the same results.
Figure 14B:
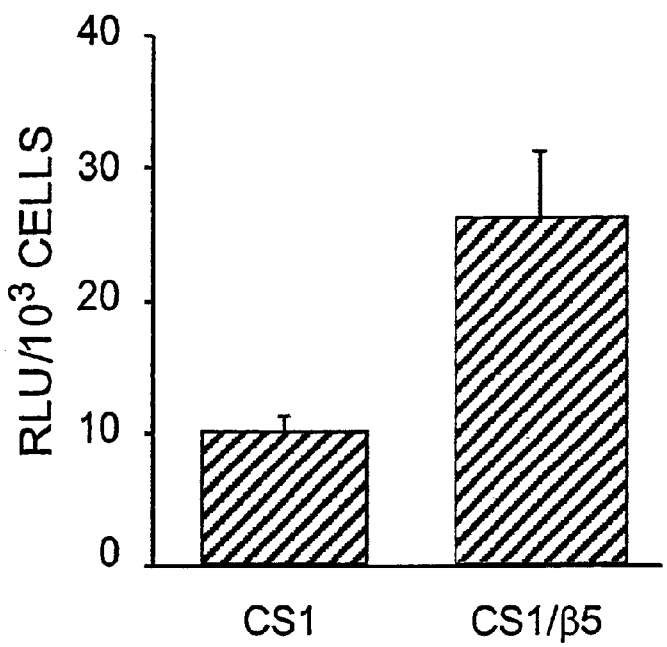
Figure 14C:
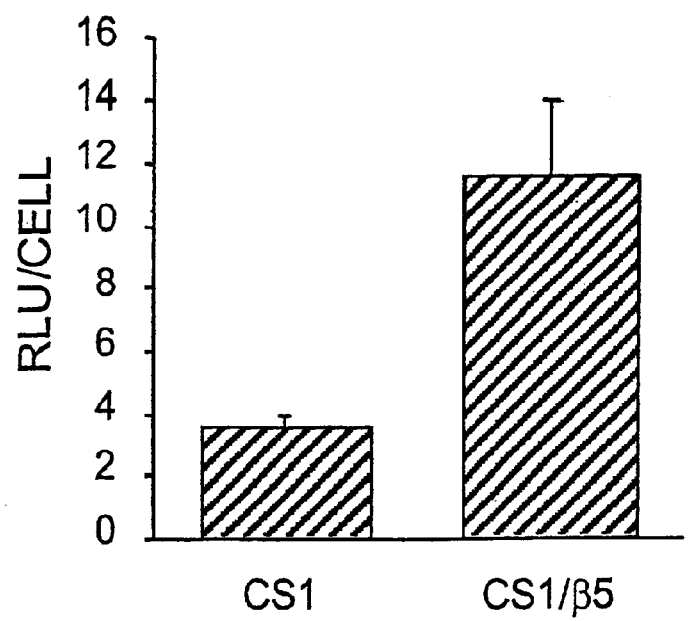

The above experiments demonstrated a physical interaction between AAV-2 virions and the beta subunit of $\alpha_v\beta_5$ integrin. To determine if this interaction was biologically significant, cell lines that either lack $\alpha_v\beta_5$ (CS-1), or express $\alpha_v\beta_5$ (CS1/$\beta$5), were tested for their ability to promote rAAV transduction. CS-1, a hamster melanoma cell line that lacks the integrin $\beta_5$ subunit, has an internal pool of $\alpha_v$ capable of complexing with integrin beta chains for expression of heterodimers on the cell surface (Thomas et al., (1993) *J. Cell Sci.* 105:191). The CS1/$\beta$5, which expresses $\alpha_v\beta_5$ on the surface, was derived by introducing a functional gene for the $\beta_5$ subunit into the CS-1 parental cell line (Wicham et al., (1994) *J. Cell biol.* 127:257). These cell lines have previously been used to assess the role of $\alpha_v\beta_5$ in adenovirus infection. Id. The CS-1 and CS1/$\beta$5 cell lines were analyzed by flow cytometric analysis (FACS) using a mAb against the $\alpha_v\beta_5$ heterodimer to ensure that homogeneous cell populations were being used (FIG. 14A). Cells were then infected with rAd-LacZ or rAAV-LacZ as described in methods and assayed for $\beta$-galactosidase activity. As shown in FIG. 14B, rAAV infection was 2.6-fold greater in CS1/$\beta$5 cells when compared to infection of parental CS-1 cells. The observed increase in rAAV transduction is similar to the 3.2-fold increase seen with rAd infection (FIG. 14C). These transduction experiments were performed with rAAV preparations that were made in the absence of infectious adenovirus (see Example 9). Thus, the possibility that Ad could affect AAV uptake or augment rAAV transduction was precluded. Therefore, these data demonstrate that the presence of $\alpha_v\beta_5$ integrin renders cells more susceptible AAV-2 infection. Since $\alpha_v\beta_5$ expression has a similar effect on both adenovirus and AAV infection, it is interesting to speculate that this integrin may play the same role in both infections.

EXAMPLE 34

Figure 15:
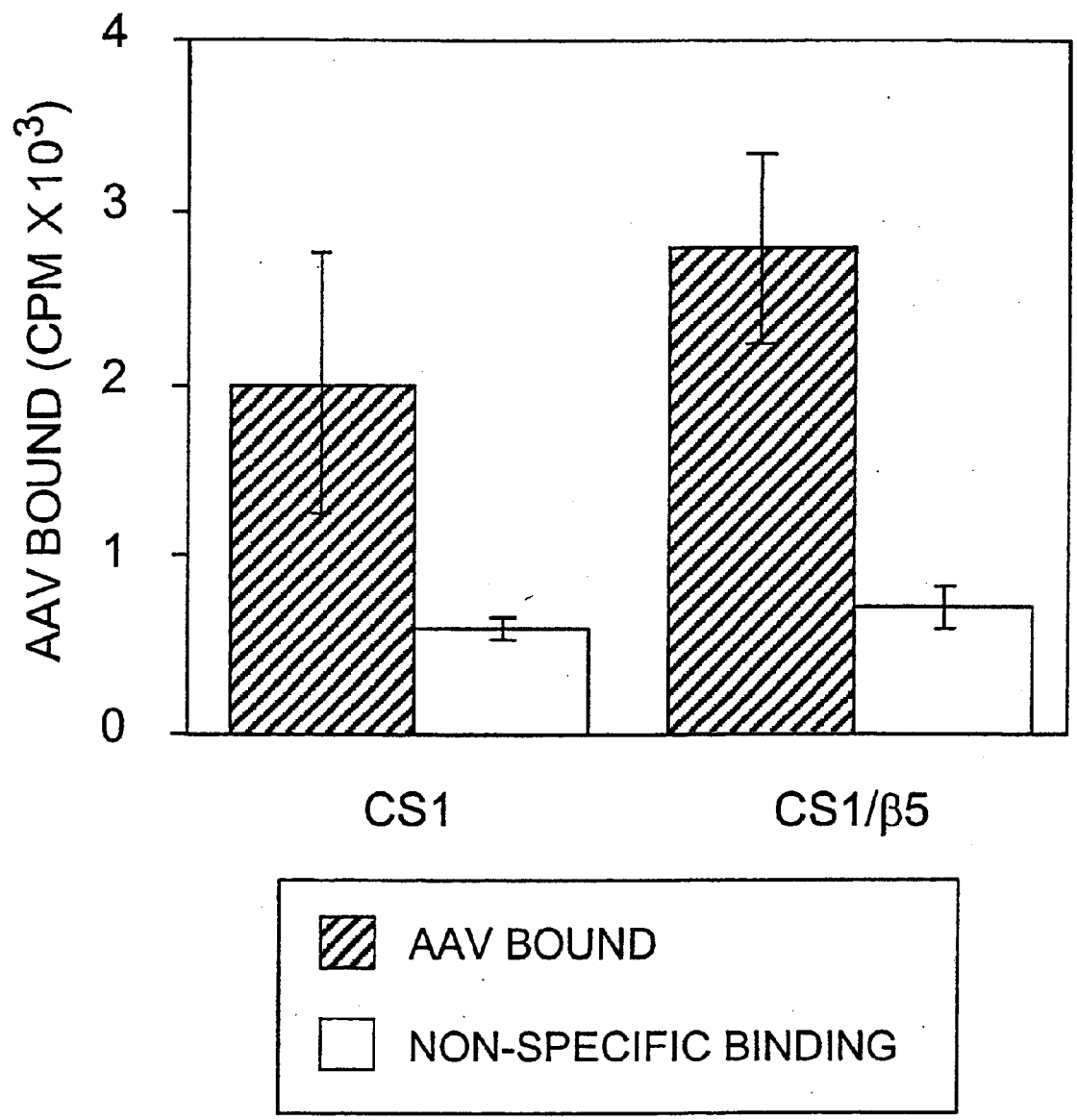
FIG. 15 demonstrates binding of AAV-2 to CS-1 and CS1/β5 cells. Direct binding assays were performed with $^3$H-wt AAV. Briefly, 4×10$^{11}$ labeled virus particles were incubated with 3×10$^5$ cells at 4° C. for 90 min. After extensive washing, cells were solubilized in 0.3 N NaOH and neutralized with glacial acetic acid prior to measuring cell associated radioactivity in a scintillation counter. Non-specific binding was determined in the presence of a 50 fold excess of unlabeled wt AAV (right-hand column). Data are the mean and standard deviation of two experiments performed in duplicate.
Figure 16A:
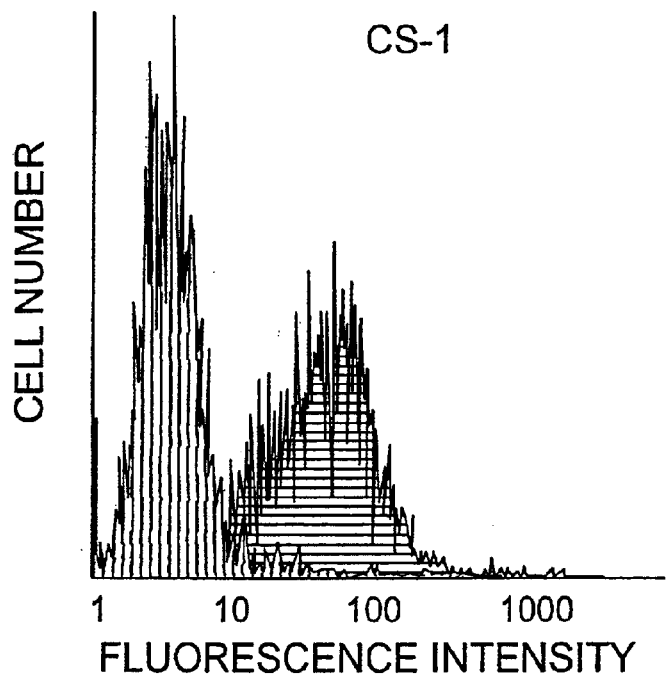
FIG. 16 illustrates cell surface expression of HS on CS-1 and CS1/β5 cells. Flow cytometric analysis of CS-1 (Panel A) and CS1/β5 (Panel B) cells was performed with monoclonal antibody HepSS-1 to detect cell surface expression of heparan sulfate. Results are overlaid onto fluorescence intensity histograms obtained with an isotype matched control antibody. CS-1 and CS1/β5 cells express similar levels of HS.
Figure 16B:
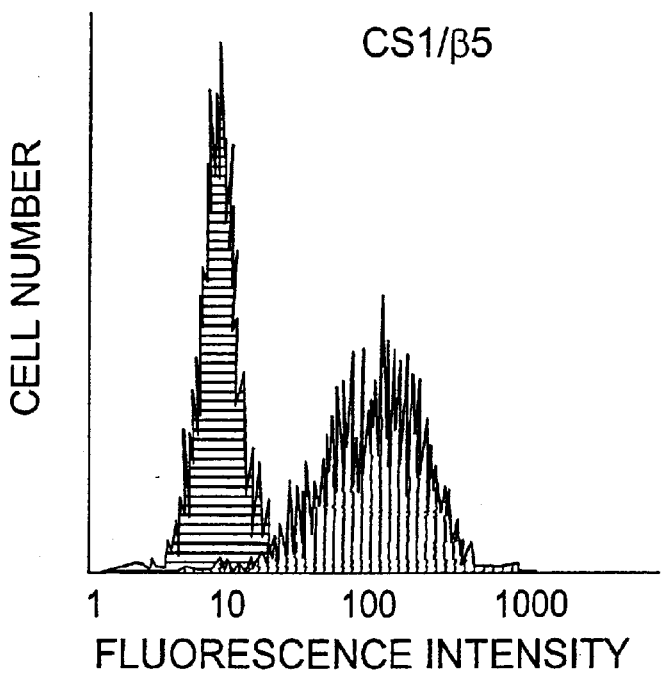

AAV-2 Attachment Is Not Significantly Enhanced by Cell Surface $\alpha_v\beta_5$ Integrin Viral overlay analysis demonstrated a direct physical interaction between AAV-2 and the $\beta_5$ subunit of $\alpha_v\beta_5$ integrin. Furthermore, viral transduction studies provided evidence that cell surface expression of $\alpha_v\beta_5$ integrin promotes AAV-2 infection. To identify a potential mechanism for the involvement of $\alpha_v\beta_5$ integrin in AAV-2 infection, the ability of $\alpha_v\beta_5$ integrin to promote binding of AAV-2 to the cell surface was assessed. Binding assays were performed with $^3$H-labeled AAV-2 in the absence or presence of a 50-fold excess of unlabeled wt AAV-2 (FIG. 15). $^3$H-AAV-2 bound specifically to both the CS-1 and CS1/$\beta$5 cell lines. While slightly more AAV-2 bound to the CS/$\beta$5 cell line, this level of binding was not significantly different than that observed to the parental cell line, CS-1. These data suggest that olvp integrin is not a primary attachment receptor for AAV-2. This is consistent with HSPG serving as a primary attachment receptor for AAV-2, since we have demonstrated that the CS-1 and CS-1/$\beta$5 cell lines express similar amounts of cell surface HSPG (FIG. 16). All of the above data led us to postulate that $\alpha_v\beta_5$ integrin may serve as a secondary receptor for AAV-2 infection. Drawing on what is known to occur during adenovirus infection, we postulated that $\alpha_v\beta_5$ integrin may facilitate virus internalization.

EXAMPLE 35

$\alpha_v\beta_5$ or Integrin Promotes AAV-2 Internalization

Figure 17:
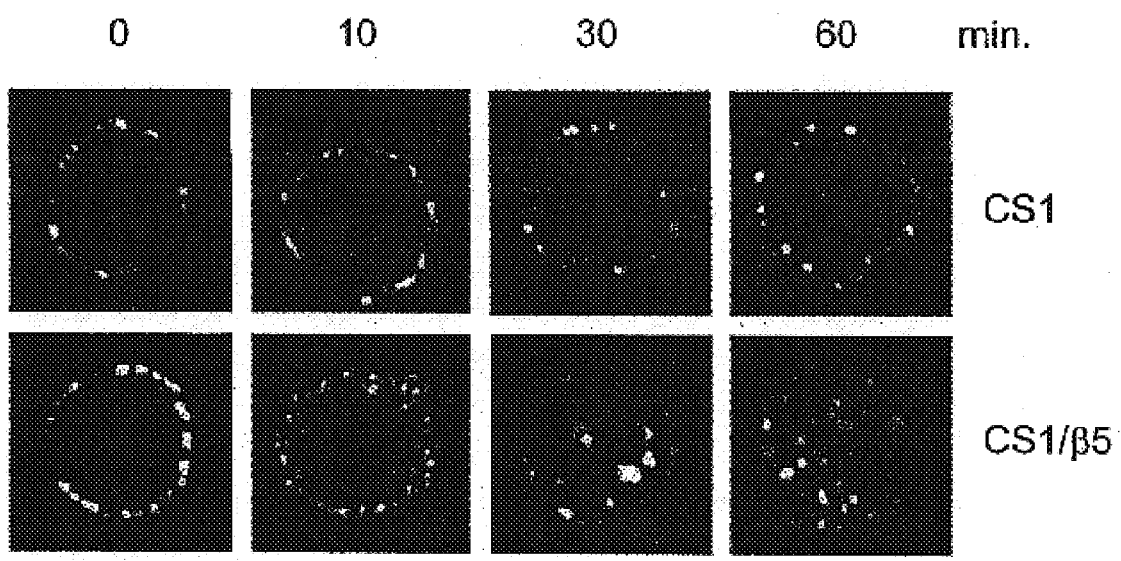
FIG. 17 illustrates Internalization of Cy3-AAV2 by CS-1 and CS1/β5 cells. Cells were incubated with Cy3-AAV2 for 1 h at 4° C., washed extensively, and then transferred to 37° C. to allow virus internalization. At the indicated times, cells were fixed and prepared for microscopy. Images were obtained by confocal microscopy from cross sections representative of the cells center. The CS1/β5 cell line shows a clear increase in the rate of internalization of the fluorescent virus relative to the CS1 cell line. Independent experiments yielded similar results.

To determine whether $\alpha_v\beta_5$ promotes AAV-2 entry, we investigated the rate of virus internalization in the CS-1 and CS1/$\beta$5 cell lines. Internalization was monitored using AAV-2 tagged with fluorescent (Cy3) dye. Fluorescent AAV-2 was incubated with cells at 4° C., and unbound virus was removed prior to initiating internalization at 37° C. At various times after the temperature shift (0', 10', 30', and 1 h), the cells were fixed and analyzed by confocal microscopy. Representative confocal images are shown in FIG. 17. The CS1/$\beta$5 cell line internalized virus at a significantly faster rate than the parental cell line (FIG. 17, compare CS1 to CS1/$\beta$5 at times 10', 30', and 60'). The enhanced rate of virus entry into the CS1/$\beta$5 cell line was specific for AAV-2, since internalization of a unrelated molecule (FITC-transferrin) was equivalent for both cell lines (data not shown). The dramatic difference in uptake of AAV into the genetically defined cell lines that lack or express $\alpha_v\beta_5$ integrin indicates that e integrin promotes AAV infection by facilitating viral internalization. This raises the interesting possibility that $\alpha_v\beta_5$ serves as a co-receptor for AAV-2.

EXAMPLE 36

Upregulation of Cell Surface Heparin Sulfate or Integrin Increases AAV Infection of Target Cells Cells to be transduced by an AAV vector, for example, for gene therapy are exposed to a compound that induces or upregulates (ie., increases) the expression of HS presumably in the form of HSPG) on the cell surface. The cells may be in vivo or removed from the subject and treated ex vivo. The compound can be transforming growth factor β, acidic fibroblast growth factor, and/or basic growth factor. Typically, the cells are preincubated with the compound prior to addition of the AAV vector. For example, the cells may be pre-treated for a sufficient time to upregulate HSPG expression prior to transducing the cells with an AAV vector. Alternatively, the cells can be treated with the compound and the AAV vector concurrently. The treatment of the cells with the compound that induces or upregulates HSPG expression increases the attachment of the AAV vector to the cell as compared with control cells. Moreover, the increase in AAV attachment to the cell is reflected by a concomitant increase in AAV infection into the cells.

Cells (as described above) can also be treated with a compound that induces or upregulates expression of $\alpha_v\beta_5$ integrin by the cell to facilitate or enhance the infection of an AAV vector into the cell. The compound may be a cytokine (e.g interleukins, in particular, IL-1b), phytohemagglutinin, granulocytemacrophage colony stimulating factor, and/or macrophage colony-stimulating factors. Cells are treated with the compound and AAV vector as described above. Exposure of cells to a compound that induces or upregulates $\alpha_v\beta_5$ integrin expression does not result in an increase in AAV binding to the cell, but it does produce an increase in AAV infection into the cell.

Cells are also treated concurrently with compounds that induce or increase HSPG and $\alpha_v\beta_5$ integrin expression to facilitate/enhance both the attachment to and infection of cells by AAV vectors.

Although the foregoing invention has been described in some detail by way of illustration and example for purposes of clarity of understanding, it will be obvious that certain changes and modifications may be practiced within the scope of the appended claims.

That which is claimed is:

1. A formulation in a physiologically acceptable carrier, comprising:
   (a) a recombinant adeno-associated virus (rAAV) vector comprising a heterologous nucleotide sequence, and
   (b) heparin.
2. The formulation of claim 1, wherein said rAAV vector is a type-2 rAAV vector.
3. The formulation of claim 1, wherein said rAAV vector is a type-3 rAAV vector.
4. The formulation of claim 1, wherein said formulation comprises a purified fraction of heparin.
5. The formulation of claim 1 further comprising heparan sulfate.
6. The formulation of claim 1, wherein said formulation comprises $10^8$ to $10^{14}$ rAAV particles.
7. The formulation of claim 1, wherein said formulation comprises $10^3$ to $10^7$ particles.
8. The formulation of claim 1, wherein said heterologous nucleotide sequence encodes a therapeutic protein or peptide.
9. The formulation of claim 8, wherein said therapeutic protein or peptide is selected from the group consisting of dystrophin, the product of a dystrophin mini-gene, utrophin, Factor VIII, Factor IX, Factor X, and the cystic fibrosis transmembrane regulator protein.
10. The formulation of claim 1, wherein said heterologous nucleotide sequence encodes an immunogenic protein or peptide.
11. The formulation of claim 1, wherein said heterologous nucleotide sequence encodes an antisense molecule.
12. The formulation of claim 1, wherein said rAAV vector comprises said heterologous nucleotide sequence inserted between AAV terminal repeats.
13. A formulation in a physiologically acceptable carrier, comprising:
    (a) a recombinant adeno-associated virus (rAAV) vector comprising a heterologous nucleotide sequence, and
    (b) heparan sulfate.
14. The formulation of claim 13, wherein said rAAV vector is a type-2 rAAV vector.
15. The formulation of claim 13, wherein said rAAV vector is a type-3 rAAV vector.
16. The formulation of claim 13, wherein said formulation comprises a purified fraction of heparin.
17. The formulation of claim 13, wherein said formulation comprises $10^8$ to $10^{14}$ rAAV particles.
18. The formulation of claim 13, wherein said formulation comprises $10^8$ to $10^7$ particles.
19. The formulation of claim 13, wherein said heterologous nucleotide sequence encodes a therapeutic protein or peptide.
20. The formulation of claim 19, wherein said therapeutic protein or peptide is selected from the group consisting of dystrophin, the product of a dystrophin mini-gene, utrophin, Factor VIII, Factor IX, Factor X, and the cystic fibrosis transmembrane regulator protein.
21. The formulation of claim 13, wherein said heterologous nucleotide sequence encodes an immunogenic protein or peptide.
22. The formulation of claim 13, wherein said heterologous nucleotide sequence encodes an antisense molecule.
23. The formulation of claim 13, wherein said rAAV vector comprises said heterologous nucleotide sequence inserted between AAV terminal repeats.
24. A formulation in a physiologically acceptable carrier, comprising:
    (a) a recombinant adeno-associated virus (rAAV) vector comprising a heterologous nucleotide sequence, and
    (b) a glycosaminoglycan consisting essentially of heparin.
25. A formulation in a physiologically acceptable carrier, comprising:
    (a) a recombinant adeno-associated virus (rAAV) vector comprising a heterologous nucleotide sequence, and
    (b) a glycosaminoglycan consisting essentially of heparan sulfate.
26. A formulation in a physiologically acceptable carrier, consisting essentially of:
    (a) a recombinant adeno-associated virus (AAV) vector comprising a heterologous nucleotide sequence, and
    (b) heparin.
27. A formulation in a physiologically acceptable carrier, consisting essentially of:
    (a) a recombinant adeno-associated virus (AAV) vector comprising a heterologous nucleotide sequence, and
    (b) heparan sulfate.
28. The formulation of claim 27 further comprising heparin.
29. The formulation of claim 1, wherein said heterologous nucleotide sequence encodes a non-translated RNA.
30. The formulation of claim 13, wherein said heterologous nucleotide sequence encodes a non-translated RNA.

* * * * *